United States Patent
Newberry

(10) Patent No.: US 10,736,580 B2
(45) Date of Patent: Aug. 11, 2020

(54) SYSTEM AND METHOD OF A BIOSENSOR FOR DETECTION OF MICROVASCULAR RESPONSES

(71) Applicant: Sanmina Corporation, San Jose, CA (US)

(72) Inventor: Robert Steven Newberry, New Hope, AL (US)

(73) Assignee: SANMINA CORPORATION, San Jose, CA (US)

(*) Notice: Subject to any disclaimer, the term of this patent is extended or adjusted under 35 U.S.C. 154(b) by 0 days.

(21) Appl. No.: 16/433,947

(22) Filed: Jun. 6, 2019

(65) Prior Publication Data
US 2019/0282179 A1    Sep. 19, 2019

Related U.S. Application Data

(60) Continuation-in-part of application No. 16/172,661, filed on Oct. 26, 2018, and a continuation-in-part of
(Continued)

(51) Int. Cl.
*A61B 5/1455* (2006.01)
*A61B 5/00* (2006.01)
(Continued)

(52) U.S. Cl.
CPC .......... *A61B 5/7275* (2013.01); *A61B 5/0002* (2013.01); *A61B 5/0022* (2013.01);
(Continued)

(58) Field of Classification Search
None
See application file for complete search history.

(56) References Cited

U.S. PATENT DOCUMENTS 4,913,150 A    4/1990  Cheung et al.
5,115,133 A    5/1992  Knudson
(Continued)

FOREIGN PATENT DOCUMENTS

CN    102609627 A    7/2012
EP    2017001250 A1    1/2017
(Continued)

OTHER PUBLICATIONS

Allen et al. "Finger microvascular responses to deep inspiratory gasp assessed and quantified using wavelet analysis", Institute of Physics and Engineering in Medicine, Physiological Measurement 34, pp. 769-779 (2013).
(Continued)

*Primary Examiner* — Eric F Winakur
*Assistant Examiner* — Marjan Fardanesh
(74) *Attorney, Agent, or Firm* — Loza & Loza, LLP; Julio M. Loza; Jessica W. Smith

(57) ABSTRACT

An optical circuit detects PPG signals reflected from skin tissue at one or more different wavelengths. A processing circuit integrated in the biosensor or in communication with the biosensor identifies an insulin release event using the a first PPG signal at a first wavelength and second PPG signal at a second wavelength. A correlation function is performed on the first and second PPG signals during the insulin release. The correlation is used to determine a relative change in diameter of vessels during the insulin release event and determine vascular health in response to the relative change.

20 Claims, 35 Drawing Sheets

Related U.S. Application Data application No. 16/270,268, filed on Feb. 7, 2019, which is a continuation of application No. 15/811,479, filed on Nov. 13, 2017, now Pat. No. 10,238,346, which is a continuation-in-part of application No. 15/490,813, filed on Apr. 18, 2017, now Pat. No. 9,980,676, which is a continuation of application No. 15/275,388, filed on Sep. 24, 2016, now Pat. No. 9,642,578, application No. 16/433,947, which is a continuation-in-part of application No. 16/183,354, filed on Nov. 7, 2018, which is a continuation of application No. 15/485,816, filed on Apr. 12, 2017, now Pat. No. 10,155,087, which is a continuation of application No. 15/276,760, filed on Sep. 26, 2016, now Pat. No. 9,636,457, application No. 16/433,947, which is a continuation-in-part of application No. 15/718,721, filed on Sep. 28, 2017, now Pat. No. 10,517,515, which is a continuation of application No. 15/622,941, filed on Jun. 14, 2017, now Pat. No. 9,788,767, application No. 16/433,947, which is a continuation-in-part of application No. 15/404,117, filed on Jan. 11, 2017, and a continuation-in-part of application No. 15/958,620, filed on Apr. 20, 2018, now Pat. No. 10,524,720, which is a continuation of application No. 15/680,991, filed on Aug. 18, 2017, now Pat. No. 9,968,289, application No. 16/433,947, which is a continuation-in-part of application No. 15/400,916, filed on Jan. 6, 2017, and a continuation-in-part of application No. 16/019,518, filed on Jun. 26, 2018, which is a division of application No. 15/867,632, filed on Jan. 10, 2018, now Pat. No. 10,039,500, application No. 16/433,947, which is a continuation-in-part of application No. 16/208,358, filed on Dec. 3, 2018, which is a continuation of application No. 15/859,147, filed on Dec. 29, 2017, now Pat. No. 10,194,871, application No. 16/433,947, which is a continuation-in-part of application No. 15/898,580, filed on Feb. 17, 2018.

(60) Provisional application No. 62/675,151, filed on May 22, 2018, provisional application No. 62/577,707, filed on Oct. 26, 2017, provisional application No. 62/613,388, filed on Jan. 3, 2018, provisional application No. 62/463,104, filed on Feb. 24, 2017.

(51) Int. Cl.
*A61B 5/145* (2006.01)
*A61B 5/01* (2006.01)
*G16H 40/63* (2018.01)
*A61B 5/024* (2006.01)
*G16H 50/30* (2018.01)

(52) U.S. Cl.
CPC ............ *A61B 5/01* (2013.01); *A61B 5/02416* (2013.01); *A61B 5/1455* (2013.01); *A61B 5/14532* (2013.01); *A61B 5/14551* (2013.01); *A61B 5/4845* (2013.01); *A61B 5/6817* (2013.01); *A61B 5/6893* (2013.01); *A61B 5/743* (2013.01); *G16H 40/63* (2018.01); *A61B 5/681* (2013.01); *A61B 5/6826* (2013.01); *A61B 5/7225* (2013.01); *A61B 2560/0223* (2013.01); *G16H 50/30* (2018.01)

(56) References Cited

U.S. PATENT DOCUMENTS

| | | |
|---|---|---|
| 5,269,310 A | 12/1993 | Jones et al. |
| 5,358,703 A | 10/1994 | Lai |
| 5,515,847 A | 5/1996 | Braig et al. |
| 5,673,692 A | 10/1997 | Schulze et al. |
| 5,823,966 A | 10/1998 | Buchert |
| 5,947,911 A | 9/1999 | Wong et al. |
| 5,983,121 A | 11/1999 | Tsuchiya |
| 6,087,087 A | 7/2000 | Yonetani et al. |
| 6,280,390 B1 | 8/2001 | Akselrod et al. |
| 6,285,896 B1 | 9/2001 | Tobler et al. |
| 6,305,804 B1 | 10/2001 | Rice et al. |
| 6,537,225 B1 | 3/2003 | Mills |
| 6,694,180 B1 | 2/2004 | Boesen |
| 6,719,705 B2 | 4/2004 | Mills |
| 6,819,950 B2 | 11/2004 | Mills |
| 6,921,367 B2 | 7/2005 | Mills |
| 6,985,763 B2 | 1/2006 | Boas et al. |
| 7,154,592 B2 | 12/2006 | Reynolds et al. |
| 7,167,736 B2 | 1/2007 | Winther |
| 7,171,251 B2 | 1/2007 | Sarussi et al. |
| 7,179,228 B2 | 2/2007 | Banet |
| 7,209,775 B2 | 4/2007 | Bae et al. |
| 7,291,497 B2 | 11/2007 | Holmes et al. |
| 7,371,562 B2 | 5/2008 | Cunningham et al. |
| 7,608,045 B2 | 10/2009 | Mills |
| 7,647,083 B2 | 1/2010 | Al-Ali et al. |
| 7,761,127 B2 | 7/2010 | Al-Ali et al. |
| 7,763,472 B2 | 7/2010 | Doctor et al. |
| 7,764,982 B2 | 7/2010 | Dalke et al. |
| 7,941,199 B2 | 5/2011 | Kiani |
| 3,224,411 A1 | 7/2012 | Al-Ali et al. |
| 8,224,411 B2 | 7/2012 | Al-Ali et al. |
| 8,255,027 B2 | 8/2012 | Al-Ali et al. |
| 8,328,420 B2 | 12/2012 | Abreu |
| 8,385,996 B2 | 2/2013 | Smith et al. |
| 8,401,605 B2 | 3/2013 | Huiku |
| 8,483,787 B2 | 7/2013 | Al-Ali et al. |
| 8,494,507 B1 | 7/2013 | Tedesco et al. |
| 8,597,274 B2 | 12/2013 | Sloan et al. |
| 8,652,040 B2 | 2/2014 | Leboeuf et al. |
| 8,676,284 B2 | 3/2014 | He |
| 8,730,047 B2 | 5/2014 | Ridder et al. |
| 8,868,149 B2 | 10/2014 | Eisen et al. |
| 8,888,701 B2 | 11/2014 | Leboeuf et al. |
| 8,906,693 B2 | 12/2014 | Schultz et al. |
| 8,923,918 B2 | 12/2014 | Kreger et al. |
| 8,961,932 B2 | 2/2015 | Silverman |
| 9,022,973 B2 | 5/2015 | Sexton et al. |
| 9,131,882 B2 | 9/2015 | Al-Ali et al. |
| 9,149,216 B2 | 10/2015 | Eisen et al. |
| 9,149,646 B2 | 10/2015 | Keswarpu et al. |
| 9,387,033 B2 | 7/2016 | Yodfat et al. |
| 9,442,092 B2 | 9/2016 | Lane |
| 9,521,970 B2 | 12/2016 | Hoppe et al. |
| 9,554,738 B1 | 1/2017 | Gulati et al. |
| 9,642,578 B2 | 5/2017 | Newberry |
| 9,668,701 B2 | 6/2017 | Maarek |
| 9,713,428 B2 | 7/2017 | Chon et al. |
| 9,739,663 B2 | 8/2017 | Halder et al. |
| 9,820,656 B2 | 11/2017 | Olivier |
| 9,839,381 B1 | 12/2017 | Weber et al. |
| 9,924,895 B2 | 3/2018 | Rawicz et al. |
| 9,949,675 B2 | 4/2018 | Miller |
| 9,999,355 B2 | 6/2018 | Kirenko |
| 10,028,682 B2 | 7/2018 | Thiele |
| D824,937 S | 8/2018 | Sparandara et al. |
| 10,099,554 B2 | 10/2018 | Steeg et al. |
| 10,130,285 B1 | 11/2018 | Singamsetty et al. |
| 10,153,796 B2 | 12/2018 | Fung et al. |
| 10,181,021 B2 | 1/2019 | Venkatraman et al. |
| 10,206,619 B1 | 2/2019 | Lee et al. |
| 10,215,698 B2 | 2/2019 | Han et al. |
| 10,227,063 B2 | 3/2019 | Abreu |
| 10,232,156 B2 | 3/2019 | Netzel et al. |
| 10,278,591 B2 | 5/2019 | Gil |

(56) References Cited

U.S. PATENT DOCUMENTS

| | | | |
|---|---|---|---|
| D850,316 S | 6/2019 | Ennis et al. | |
| 10,314,500 B2 | 6/2019 | Olivier | |
| 10,322,728 B1 | 6/2019 | Porikli et al. | |
| 10,342,495 B2 | 7/2019 | Melkoniemi et al. | |
| 10,349,847 B2 | 7/2019 | Kwon et al. | |
| 10,420,470 B2 | 9/2019 | Kwon et al. | |
| 10,420,491 B2 | 9/2019 | Rajan et al. | |
| 10,433,726 B2 | 10/2019 | Ramesh et al. | |
| 10,433,738 B2 | 10/2019 | Thomas et al. | |
| 10,433,739 B2 | 10/2019 | Weekly et al. | |
| 10,463,283 B2 | 11/2019 | Ferber et al. | |
| 2002/0049389 A1 | 4/2002 | Abreu | |
| 2002/0103454 A1* | 8/2002 | Sackner | A61H 1/001 604/19 |
| 2003/0229276 A1 | 12/2003 | Sarussi et al. | |
| 2004/0078219 A1 | 4/2004 | Kaylor et al. | |
| 2004/0100376 A1 | 5/2004 | Lye et al. | |
| 2004/0157341 A1 | 8/2004 | Reynolds et al. | |
| 2005/0101841 A9 | 5/2005 | Kaylor et al. | |
| 2005/0209516 A1 | 9/2005 | Fraden | |
| 2005/0228244 A1 | 10/2005 | Banet | |
| 2005/0228299 A1 | 10/2005 | Banet | |
| 2005/0245831 A1 | 11/2005 | Banet | |
| 2006/0009698 A1 | 1/2006 | Banet | |
| 2006/0094942 A1 | 5/2006 | Winther | |
| 2006/0287589 A1 | 12/2006 | Wobermin et al. | |
| 2007/0202605 A1 | 8/2007 | Doctor et al. | |
| 2007/0203405 A1 | 8/2007 | Shimomura | |
| 2007/0260132 A1 | 11/2007 | Sterling | |
| 2008/0146890 A1 | 6/2008 | Leboeuf et al. | |
| 2008/0165017 A1 | 7/2008 | Schwartz | |
| 2008/0208019 A1 | 8/2008 | Nitzan | |
| 2008/0241199 A1 | 10/2008 | Silverman | |
| 2009/0043178 A1 | 2/2009 | Belotserkovsky | |
| 2009/0156988 A1 | 6/2009 | Ferren et al. | |
| 2009/0187167 A1 | 7/2009 | Sexton et al. | |
| 2009/0287120 A1 | 11/2009 | Ferren et al. | |
| 2010/0049020 A1 | 2/2010 | Dalke et al. | |
| 2010/0191080 A1 | 7/2010 | Mills | |
| 2010/0274101 A1 | 10/2010 | Lin et al. | |
| 2010/0331631 A1 | 12/2010 | MacLaughlin | |
| 2011/0082355 A1 | 4/2011 | Eisen et al. | |
| 2011/0106050 A1 | 5/2011 | Yodfat et al. | |
| 2011/0137141 A1 | 6/2011 | Razoumov et al. | |
| 2011/0160697 A1 | 6/2011 | Yodfat et al. | |
| 2011/0166553 A1 | 7/2011 | Holmes et al. | |
| 2011/0224518 A1 | 9/2011 | Tindi et al. | |
| 2011/0237464 A1 | 9/2011 | Cunningham et al. | |
| 2011/0275978 A1 | 11/2011 | Hyde et al. | |
| 2012/0010683 A1 | 1/2012 | Keswarpu et al. | |
| 2012/0029363 A1 | 2/2012 | Lund | |
| 2012/0095302 A1 | 4/2012 | Adhikari | |
| 2012/0131507 A1 | 5/2012 | Sparandara et al. | |
| 2012/0136054 A1 | 5/2012 | Schultz et al. | |
| 2012/0156933 A1 | 6/2012 | Kreger et al. | |
| 2012/0203077 A1 | 8/2012 | He et al. | |
| 2012/0238844 A1 | 9/2012 | Grata et al. | |
| 2012/0330126 A1 | 12/2012 | Hoppe et al. | |
| 2013/0030259 A1 | 1/2013 | Thomsen et al. | |
| 2013/0060098 A1 | 3/2013 | Thomsen et al. | |
| 2013/0066176 A1 | 3/2013 | Addison et al. | |
| 2013/0110311 A1 | 5/2013 | Ver Steeg et al. | |
| 2013/0310669 A1 | 11/2013 | Nitzan | |
| 2014/0046160 A1 | 2/2014 | Terashima et al. | |
| 2014/0100432 A1 | 4/2014 | Golda et al. | |
| 2014/0112940 A1 | 4/2014 | Lane | |
| 2014/0194342 A1 | 7/2014 | Zhang et al. | |
| 2014/0243648 A1 | 8/2014 | Dubielczyk | |
| 2014/0253709 A1 | 9/2014 | Bresch et al. | |
| 2014/0275852 A1 | 9/2014 | Hong et al. | |
| 2014/0297313 A1 | 10/2014 | Condurso et al. | |
| 2014/0316226 A1 | 10/2014 | Ferber et al. | |
| 2015/0066238 A1 | 3/2015 | Todd et al. | |
| 2015/0088007 A1 | 3/2015 | Bardy et al. | |
| 2015/0094914 A1 | 4/2015 | Abreu | |
| 2015/0105638 A1 | 4/2015 | Eisen et al. | |
| 2015/0109617 A1 | 4/2015 | Gilbert et al. | |
| 2015/0148622 A1 | 5/2015 | Moyer et al. | |
| 2015/0148635 A1 | 5/2015 | Benaron | |
| 2015/0150453 A1 | 6/2015 | Abreu | |
| 2015/0182172 A1 | 7/2015 | Shelley et al. | |
| 2015/0229341 A1 | 8/2015 | Fung et al. | |
| 2015/0250404 A1 | 9/2015 | Maarek | |
| 2015/0282747 A1 | 10/2015 | Thiele | |
| 2015/0366471 A1 | 12/2015 | Leboeuf et al. | |
| 2016/0018257 A1 | 1/2016 | Mirov et al. | |
| 2016/0058308 A1 | 3/2016 | Robinson | |
| 2016/0058347 A1 | 3/2016 | Reichgott et al. | |
| 2016/0066863 A1 | 3/2016 | Thaveeprungsrporn et al. | |
| 2016/0100781 A1 | 4/2016 | Bechtel et al. | |
| 2016/0262707 A1 | 9/2016 | Devries | |
| 2016/0367154 A1 | 12/2016 | Gladshtein et al. | |
| 2017/0027521 A1 | 2/2017 | Geva et al. | |
| 2017/0050518 A1 | 2/2017 | Steeg et al. | |
| 2017/0071550 A1 | 3/2017 | Newberry | |
| 2017/0091436 A1 | 3/2017 | Cao et al. | |
| 2017/0095215 A1* | 4/2017 | Watson | A61B 5/7285 |
| 2017/0172477 A1 | 6/2017 | Adusumilli et al. | |
| 2017/0215811 A1 | 8/2017 | Newberry | |
| 2017/0256110 A1 | 9/2017 | Divincent et al. | |
| 2017/0347894 A1 | 12/2017 | Bhushan et al. | |
| 2017/0347899 A1 | 12/2017 | Bhushan et al. | |
| 2018/0117291 A1 | 5/2018 | Netzel et al. | |
| 2018/0140210 A1 | 5/2018 | Jelfs et al. | |
| 2018/0140237 A1 | 5/2018 | Rajan et al. | |
| 2018/0177416 A1 | 6/2018 | Church et al. | |
| 2018/0177440 A1 | 6/2018 | Jelfs et al. | |
| 2018/0200433 A1 | 7/2018 | Cirit | |
| 2018/0264242 A1 | 9/2018 | Hoffman et al. | |
| 2018/0353137 A1 | 12/2018 | Balajadia et al. | |
| 2018/0358119 A1 | 12/2018 | Bhushan et al. | |
| 2019/0046039 A1 | 2/2019 | Ramesh et al. | |
| 2019/0050622 A1 | 2/2019 | Cabibihan et al. | |
| 2019/0086331 A1 | 3/2019 | Han | |
| 2019/0099114 A1 | 4/2019 | Mouradian et al. | |
| 2019/0110745 A1 | 4/2019 | Linnes et al. | |
| 2019/0125963 A1 | 5/2019 | Mou et al. | |
| 2019/0125964 A1 | 5/2019 | Mou et al. | |
| 2019/0133471 A1 | 5/2019 | Olson et al. | |
| 2019/0192085 A1 | 6/2019 | Krishna et al. | |
| 2019/0192086 A1 | 6/2019 | Krishna et al. | |
| 2019/0251238 A1 | 8/2019 | Venkatraman et al. | |
| 2019/0358387 A1 | 11/2019 | Elbadry et al. | |

FOREIGN PATENT DOCUMENTS

| | | |
|---|---|---|
| EP | 3488776 A1 | 5/2019 |
| WO | 2004047630 A1 | 6/2004 |
| WO | 2007013054 A1 | 2/2007 |
| WO | 2008006150 A1 | 1/2008 |
| WO | 2010128852 A3 | 11/2010 |
| WO | 2010147968 A1 | 12/2010 |
| WO | 2012108895 A1 | 8/2012 |
| WO | 2013052318 A1 | 4/2013 |
| WO | 2013127564 A1 | 9/2013 |
| WO | 2014163583 A1 | 10/2014 |
| WO | 2015143197 A1 | 9/2015 |
| WO | 2015200148 A1 | 12/2015 |
| WO | 2017001249 A1 | 1/2017 |
| WO | 2018206875 A1 | 11/2018 |
| WO | 2019030700 A1 | 2/2019 |
| WO | 2019118053 A1 | 6/2019 |

OTHER PUBLICATIONS

Böhm et al. "The importance of endothelin-1 for vascular dysfunction in cardiovascular disease", Cardiovascular Research 76, pp. 8-18 (2007).

Cardillo et al. "Insulin stimulates both endothelin and nitric oxide activity in the human forearm", Circulation 822 (Aug. 24, 1999).

Chalacheva, et al. "Modeling of deep breath vasoconstriction reflex", Cont Proc. IEEE Eng. Med. Biol. Soc. 7792-7795 (Aug. 2015).

(56) References Cited

OTHER PUBLICATIONS

Davenport et al. "Endothelin", Pharmacological Reviews 68: 357-418 (Apr. 2016).
Eringa et al. "Vasoconstrictor effects of insulin in skeletal muscle arterioles are mediated by ERK1/2 activation in endothelium", Am. Journal Physiol. Heart Circ. Physiol. 287: H2043-H2048 (Apr. 1, 2004).
Karimipour et al. "Diabetic diagnose test based on PPG signal and identification system", J. Biomedical Science and Engineering, vol. 2:6, pp. 465-469 (2009).
Mather et al. "Interactions between endothelin and nitric oxide in the regulation of vascular tone in obesity and diabetes", Diabetes vol. 53, pp. 2060-2066 (Aug. 2004).
Mitchell et al. "Vasoconstrictor effects of insulin in the human microcirculation are mediated via endothelin-1-type-B-receptors", Journal of Hypertension, vol. 28:e-Supp A (Jun. 2010).

* cited by examiner

SYSTEM AND METHOD OF A BIOSENSOR FOR DETECTION OF MICROVASCULAR RESPONSES

CROSS REFERENCE TO RELATED APPLICATIONS

The present application claims priority under 35 U.S.C. § 120 as a continuation in part to U.S. patent application Ser. No. 16/172,661 entitled, "SYSTEM AND METHOD OF A BIOSENSOR FOR DETECTION OF VASODILATION," filed Oct. 26, 2018, and hereby expressly incorporated by reference herein, which claims priority under 35 U.S.C. § 119(e) to:

U.S. Provisional Application No. 62/675,151 entitled, "SYSTEM AND METHOD OF A BIOSENSOR FOR DETECTION OF VASODILATION," filed May 22, 2018, and hereby expressly incorporated by reference herein;

U.S. Provisional Application No. 62/577,707 entitled, "SYSTEM AND METHOD FOR HEALTH MONITORING OF AN ANIMAL USING A MULTI-BAND BIOSENSOR," filed Oct. 26, 2017, and hereby expressly incorporated by reference herein; and U.S. Provisional Application No. 62/613,388 entitled, "SYSTEM AND METHOD FOR INFECTION DISCRIMINATION USING PPG TECHNOLOGY," filed Jan. 3, 2018, and hereby expressly incorporated by reference herein.

The present application claims priority under 35 U.S.C. § 120 as a continuation in part to U.S. patent application Ser. No. 16/270,268 entitled, "SYSTEM AND METHOD FOR GLUCOSE MONITORING," filed Feb. 7, 2019, and hereby expressly incorporated by reference herein which claims priority under 35 U.S.C. § 120 as a continuation application to U.S. patent application Ser. No. 15/811,479 entitled, "SYSTEM AND METHOD FOR A BIOSENSOR INTEGRATED IN A VEHICLE," filed Nov. 13, 2017, now U.S. Pat. No. 10,238,346 issued Mar. 26, 2019 and hereby expressly incorporated by reference herein, which claims priority under 35 U.S.C. § 120 as a continuation in part application to U.S. patent application Ser. No. 15/490,813 entitled, "SYSTEM AND METHOD FOR HEALTH MONITORING USING A NON-INVASIVE, MULTI-BAND BIOSENSOR," filed Apr. 18, 2017, now U.S. Pat. No. 9,980,676 issued May 29, 2018 which claims priority under 35 U.S.C. § 120 as a continuation application to U.S. patent application Ser. No. 15/275,388 entitled, "SYSTEM AND METHOD FOR HEALTH MONITORING USING A NON-INVASIVE, MULTI-BAND BIOSENSOR," filed Sep. 24, 2016, now U.S. Pat. No. 9,642,578 issued May 9, 2017.

The present application claims priority under 35 U.S.C. § 120 as a continuation in part application to U.S. patent application Ser. No. 16/183,354 entitled, "SYSTEM AND METHOD FOR HEALTH MONITORING BY AN EAR PIECE," filed Nov. 7, 2018 and hereby expressly incorporated by reference herein, which claims priority under 35 U.S.C. § 120 as a continuation application to U.S. patent application Ser. No. 15/485,816 entitled, "SYSTEM AND METHOD FOR A DRUG DELIVERY AND BIOSENSOR PATCH," filed Apr. 12, 2017, now U.S. Pat. No. 10,155,087 issued Dec. 18, 2018 and hereby expressly incorporated by reference herein, which claims priority under 35 U.S.C. § 120 as a continuation application to U.S. Utility application Ser. No. 15/276,760, entitled, "SYSTEM AND METHOD FOR A DRUG DELIVERY AND BIOSENSOR PATCH," filed Sep. 26, 2016, now U.S. Pat. No. 9,636,457 issued May 2, 2017, which is hereby expressly incorporated by reference herein.

The present application claims priority under 35 U.S.C. § 120 as a continuation in part application to U.S. patent application Ser. No. 15/718,721 entitled, "SYSTEM AND METHOD FOR MONITORING NITRIC OXIDE LEVELS USING A NON-INVASIVE, MULTI-BAND BIOSENSOR," filed Sep. 28, 2017 and hereby expressly incorporated by reference herein, which claims priority as a continuation application to U.S. Utility application Ser. No. 15/622,941 entitled, "SYSTEM AND METHOD FOR MONITORING NITRIC OXIDE LEVELS USING A NON-INVASIVE, MULTI-BAND BIOSENSOR," filed Jun. 14, 2017, now U.S. Pat. No. 9,788,767 issued Oct. 17, 2017, and hereby expressly incorporated by reference herein, which claims priority under 35 U.S.C. § 119 to U.S. Provisional Application No. 62/463,104 entitled, "SYSTEM AND METHOD FOR MONITORING NITRIC OXIDE LEVELS USING A NON-INVASIVE, MULTI-BAND BIOSENSOR," filed Feb. 24, 2017, and hereby expressly incorporated by reference herein.

The present application claims priority under 35 U.S.C. § 120 as a continuation in part application to U.S. patent application Ser. No. 15/404,117 entitled, "SYSTEM AND METHOD FOR HEALTH MONITORING INCLUDING A USER DEVICE AND BIOSENSOR," filed Jan. 11, 2017 and hereby expressly incorporated by reference herein.

The present application claims priority under 35 U.S.C. § 120 as a continuation in part application to U.S. Utility application Ser. No. 15/958,620 entitled, "SYSTEM AND METHOD FOR DETECTING A HEALTH CONDITION USING AN OPTICAL SENSOR," filed Apr. 20, 2018, and hereby expressly incorporated by reference herein which claims priority under 35 U.S.C. § 120 as a continuation application to U.S. Utility application Ser. No. 15/680,991 entitled, "SYSTEM AND METHOD FOR DETECTING A SEPSIS CONDITION," filed Aug. 18, 2017, now U.S. Pat. No. 9,968,289 issued May 15, 2018 and hereby expressly incorporated by reference herein.

The present application claims priority under 35 U.S.C. § 120 as a continuation in part application to U.S. patent application Ser. No. 15/400,916 entitled, "SYSTEM AND METHOD FOR HEALTH MONITORING INCLUDING A REMOTE DEVICE," filed Jan. 6, 2017 and hereby expressly incorporated by reference herein.

The present application claims priority under 35 U.S.C. § 120 as a continuation in part to U.S. patent application Ser. No. 16/019,518 entitled, "SYSTEM AND METHOD FOR BLOOD TYPING USING PPG TECHNOLOGY," filed Jun. 26, 2018, and hereby expressly incorporated by reference herein, which claims priority under 35 U.S.C. § 120 as a divisional to U.S. patent application Ser. No. 15/867,632 entitled, "SYSTEM AND METHOD FOR BLOOD TYPING USING PPG TECHNOLOGY," filed Jan. 10, 2018, now U.S. Pat. No. 10,039,500 issued Aug. 7, 2018 and hereby expressly incorporated by reference herein.

The present application claims priority under 35 U.S.C. § 120 as a continuation in part to U.S. patent application Ser. No. 16/208,358 entitled, "VEHICULAR HEALTH MONITORING SYSTEM AND METHOD," filed Dec. 3, 2018 which claims priority as a continuation to U.S. patent application Ser. No. 15/859,147 entitled, "VEHICULAR HEALTH MONITORING SYSTEM AND METHOD," filed Dec. 29, 2017, now U.S. Pat. No. 10,194,871 issued Feb. 5, 2019 and both of which are hereby expressly incorporated by reference herein.

The present application claims priority under 35 U.S.C. § 120 as a continuation in part to U.S. patent application Ser. No. 15/898,580 entitled, "SYSTEM AND METHOD FOR OBTAINING HEALTH DATA USING A NEURAL NETWORK," filed Feb. 17, 2018, and hereby expressly incorporated by reference herein.

FIELD

This application relates to systems and methods of non-invasive health monitoring, and in particular, a system and method for detection of vascular health using an optical sensor.

BACKGROUND

A person's vitals, such as temperature, blood oxygen levels, respiration rate, relative blood pressure, etc., may need to be monitored periodically typically using one or more instruments. For example, instruments for obtaining vitals of a user include blood pressure cuffs, thermometers, $SpO_2$ measurement devices, glucose level meters, etc. The detection of substances and measurement of concentration level or indicators of various substances in a user's blood stream is important in health monitoring. Currently, detection of concentration levels of blood substances is performed by drawing blood from a blood vessel using a needle and syringe. The blood sample is then transported to a lab for analysis. This type of monitoring is invasive, non-continuous and time consuming.

One current non-invasive method is known for measuring the oxygen saturation of blood using pulse oximeters. Pulse oximeters detect oxygen saturation of hemoglobin by using, e.g., spectrophotometry to determine spectral absorbencies and determining concentration levels of oxygen based on Beer-Lambert law principles. In addition, pulse oximetry may use photoplethysmography (PPG) methods for the assessment of oxygen saturation in pulsatile arterial blood flow. The subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood, i.e. that due to arterial blood (AC components), from the constant absorbance by nonpulsatile venous or capillary blood or tissue pigments (DC components), to eliminate the effect of tissue absorbance to measure the oxygen saturation of arterial blood.

For example, when the heart pumps blood to the body and the lungs during systole, the amount of blood that reaches the capillaries in the skin surface increases, resulting in more light absorption. The blood then travels back to the heart through the venous network, leading to a decrease of blood volume in the capillaries and less light absorption. The measured PPG waveform therefore comprises a pulsatile (often called "AC") physiological waveform that reflects cardiac synchronous changes in the blood volume with each heartbeat, which is superimposed on a much larger slowly varying quasi-static ("DC") baseline. The use of PPG techniques as heretofore been used for measurement of the oxygen saturation of blood in vessels.

As such, there is a need for a non-invasive health monitoring system and method that monitors health conditions of a user non-invasively, continuously and in real time.

In particular, there is a need for an improved system and method for detection of vascular health and conditions affected by vascular health.

SUMMARY

According to a first aspect, a device includes an optical circuit configured to detect photoplethysmography (PPG) signals, wherein a first PPG signal includes a first spectral response obtained from light reflected around a first wavelength from tissue of a user and a second PPG signal includes a second spectral response obtained from light reflected around a second wavelength from the tissue of the user. The device further includes a processing device configured to identify an insulin release event using the first PPG signal and the second PPG signal, wherein the insulin release event includes insulin released into blood flow of a vessel in the tissue of the user.

According to a second aspect, a biosensor includes an optical circuit configured to detect a first PPG signal reflected around a first wavelength from skin tissue of a patient and a second PPG signal reflected around a second wavelength from the skin tissue of the patient. The biosensor further includes a processing circuit configured to identify an insulin release event using the first PPG signal or the second PPG signal. The processing circuit is further configured to determine a level of vasoconstriction during the insulin release event; compare the level of vasoconstriction to a predetermined range of vasoconstriction measured from a general population with healthy vascular systems; and determine a balance of efficacy of endothelin (ET-1) and nitric oxide (NO) during the insulin release event.

According to a third aspect, a device includes a PPG circuit configured to obtain a first PPG signal around a first wavelength reflected from skin tissue of a patient and a second PPG signal around a second wavelength reflected from the skin tissue of the patient, wherein the first wavelength has a high absorption coefficient for NO in the skin tissue of the patient and the second wavelength has a lower absorption coefficient for NO in the skin tissue of the patient. The device further includes a processing device configured to identify an insulin release event using the first and second PPG signals.

In one or more of the above aspects, the processing device is configured to identify an insulin release event using the first PPG signal and the second PPG signal by determining a change in amplitude of the first PPG signal or the second PPG signal and comparing the change in the amplitude of the first PPG signal or the second PPG signal to a predetermined range of amplitude of PPG signals during an insulin release event.

In one or more of the above aspects, the processing device is configured to identify an insulin release event using the first PPG signal and the second PPG signal by determining a period of a PPG pulse, wherein the PPG pulse includes a change in amplitude of the first PPG signal or the second PPG signal and comparing the period of the PPG pulse to a predetermined range of time periods of an insulin release event.

In one or more of the above aspects, the processing device is configured to determine an R value curve using a ratio value obtained from a first AC component of the first PPG signal and a second AC component of the second PPG signal and compare the R value curve to typical R value curves during an insulin release.

In one or more of the above aspects, the processing device is configured to determine an insulin level during the insulin release event by determining an R value curve during the insulin release event using a ratio value obtained from a first AC component of the first PPG signal and a second AC component of the second PPG signal; determining an integral area of the R value curve during the insulin release event; and determining the insulin level using the area of the R value curve and the calibration.

In one or more of the above aspects, the processing device is configured to identify a number of insulin release events during a time period and determine at least one of: a stage of digestion, an estimated time since caloric intake or a level of hunger.

In one or more of the above aspects, the processing device is configured to determine a correlation signal during the insulin release event between the first PPG signal and the second PPG signal, wherein the correlation signal includes a phase delay between the first PPG signal and the second PPG signal or a pulse shape correlation between the first PPG signal and the second PPG signal and determine a measurement of vascular health using the correlation signal.

In one or more of the above aspects, the processing device is configured to determine a level of vasoconstriction using the correlation signal during the insulin release event.

In one or more of the above aspects, the processing device is configured to compare the level of vasoconstriction to a predetermined range of vasoconstriction measured from a general population with healthy vascular systems and determine a balance of efficacy of endothelin (ET-1) and nitric oxide (NO) during the insulin release event.

In one or more of the above aspects, the processing device is configured to determine a vascular dysfunction in the user determine a ratio value obtained from a first AC component of the first PPG signal and a second AC component of the second PPG signal; access an individual calibration table between predetermined ratio values and glucose levels; and obtain a glucose level using the individual calibration and the ratio value.

DETAILED DESCRIPTION

Figure 1:
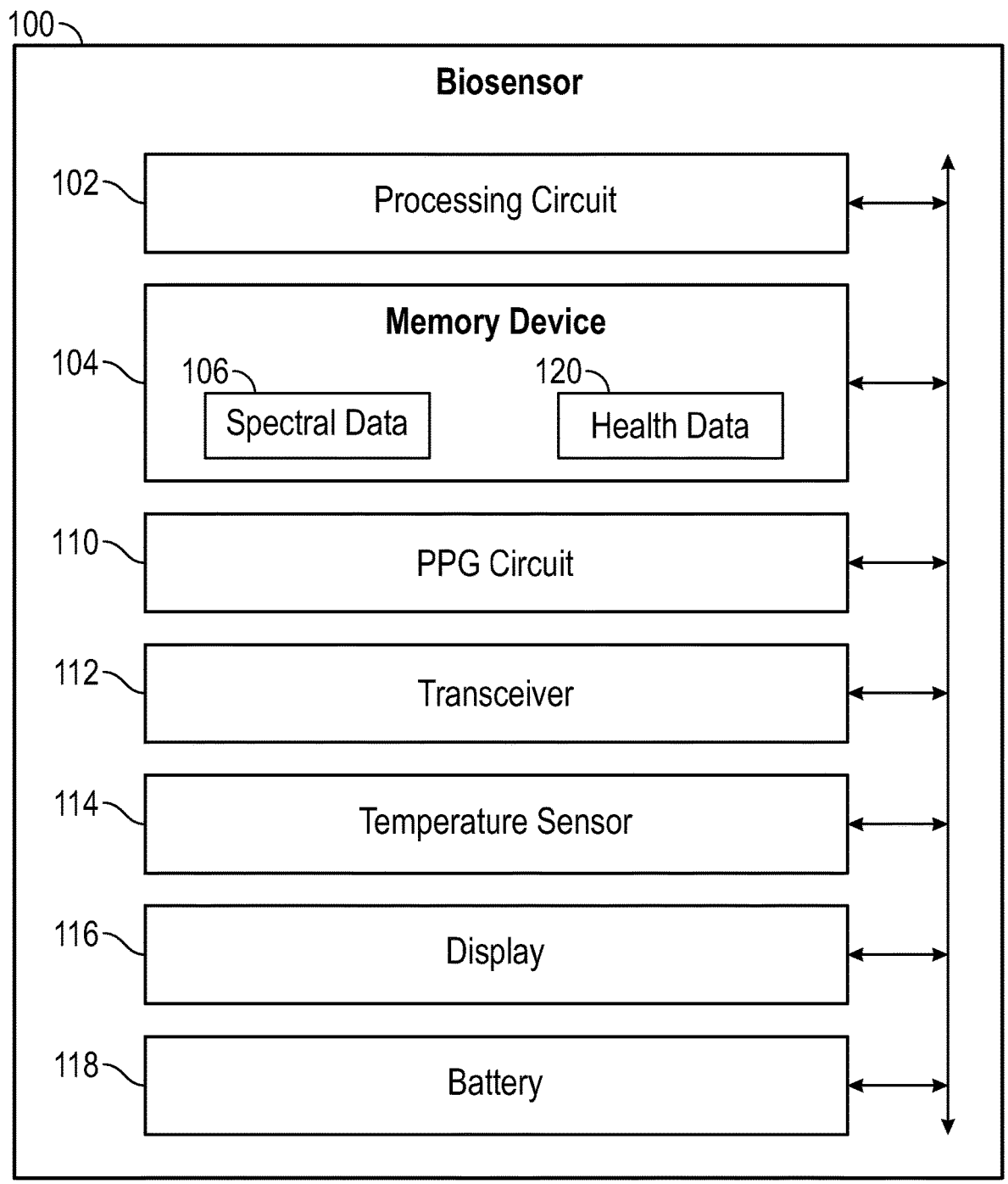
FIG. 1 illustrates a schematic block diagram of exemplary components in an embodiment of the biosensor.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview

The release of the Endothelium-derived relaxing factor (EDRF) causes the arteries to expand in diameter and change elasticity, commonly referred to as vasodilation. Flow-mediated vasodilation measurements have been performed in human studies and are of diagnostic and prognostic importance. Prior techniques for measuring vasodilation require using high-frequency ultrasound to visually inspect vessels, most commonly the brachial artery. For example, one ultrasound technique evaluates flow-mediated vasodilation (FMD), an endothelium-dependent function, in the brachial artery. This process includes applying a stimulus to provoke the endothelium to release nitric oxide (NO) with subsequent vasodilation that is then imaged using high resolution ultrasonography and quantitated as an index of vasomotor function. This process of high-resolution ultrasonography of the brachial artery to evaluate vasomotor function has limitations. It must be performed in a clinical setting by a medical clinician using expensive ultrasonography equipment.

Thus, there is a need for an improved system and method for detection of vasodilation or vasoconstriction, and vascular health.

Embodiment of the Biosensor

In an embodiment, a biosensor includes an optical sensor or photoplethysmography (PPG) circuit configured to transmit light at a plurality of wavelengths directed at skin tissue of a user or patient. The user/patient may include any animal, human or non-human. The PPG circuit detects the light reflected from the skin tissue or transmitted through the skin tissue and generates one or more spectral responses at one or more wavelengths. A processing circuit integrated in the biosensor or in communication with the biosensor processes the spectral data to obtain a user's vitals, concentrations of substances in blood flow and/or other health information.

FIG. 1 illustrates a schematic block diagram of exemplary components in an embodiment of the biosensor 100. The biosensor 100 is configured to detect oxygen saturation (SaO2 or SpO2) levels in blood flow, as well as concentration levels of one or more other substances in blood flow of a user. In addition, the biosensor 100 is configured to detect a level of vasodilation and/or a period of vasodilation using one or more measurement techniques as described in more detail herein. The biosensor 100 includes a PPG circuit 110 as described in more detail herein.

The biosensor 100 may include one or more processing circuits 102 communicatively coupled to a memory device 104. In one aspect, the memory device 104 may include one or more non-transitory processor readable memories that store instructions which when executed by the one or more processing circuits 102, causes the one or more processing circuits 102 to perform one or more functions described herein. The processing circuit 102 may be co-located with one or more of the other circuits of the biosensor 100 in a same physical circuit board or located separately in a different circuit board or encasement. The processing circuit 102 may also be communicatively coupled to a central control module or server in a remote location as described further herein. The biosensor 100 may be battery operated and include a battery 118, such as a lithium ion battery. The memory device 104 may store spectral data 106 or health data 120 obtained by the biosensor 100.

The biosensor 100 may include a temperature sensor 114 configured to detect a temperature of a user. For example, the temperature sensor 108 may include an array of sensors (e.g., 16×16 pixels) to detect a skin temperature of a user. The temperature sensor 114 may also be used to calibrate the PPG circuit 110, such as the wavelength output of LEDs or other light sources. The biosensor 100 may include a display 116 to display biosensor data or control interfaces for the biosensor 100.

The biosensor 100 further includes a transceiver 112. The transceiver 112 may include a wireless or wired transceiver configured to communicate with or with one or more devices over a LAN, MAN and/or WAN. In one aspect, the wireless transceiver may include a Bluetooth enabled (BLE) transceiver or IEEE 802.11ah, Zigbee, IEEE 802.15-11 or WLAN (such as an IEEE 802.11 standard protocol) compliant transceiver. In another aspect, the wireless transceiver may operate using RFID, short range radio frequency, infrared link, or other short range wireless communication protocol. In another aspect, the wireless transceiver may also include or alternatively include an interface for communicating over a cellular network. The transceiver 112 may also include a wired transceiver interface, e.g., a USB port or other type of wired connection, for communication with one or more other devices over a LAN, MAN and/or WAN. The transceiver 112 may include a wireless or wired transceiver configured to communicate with a vehicle or its components over a controller area network (CAN), Local Interconnect Network (LIN), Flex Ray, Media Oriented Systems Transport (MOST), (On-Board Diagnostics II), Ethernet or using another type of network or protocol. The biosensor 100 may transmit health data using the transceiver 112 over a wide area network, such as a cellular network, to a third party service provider, such as a health care provider or emergency service provider.

Embodiment—PPG Circuit

Figure 2:
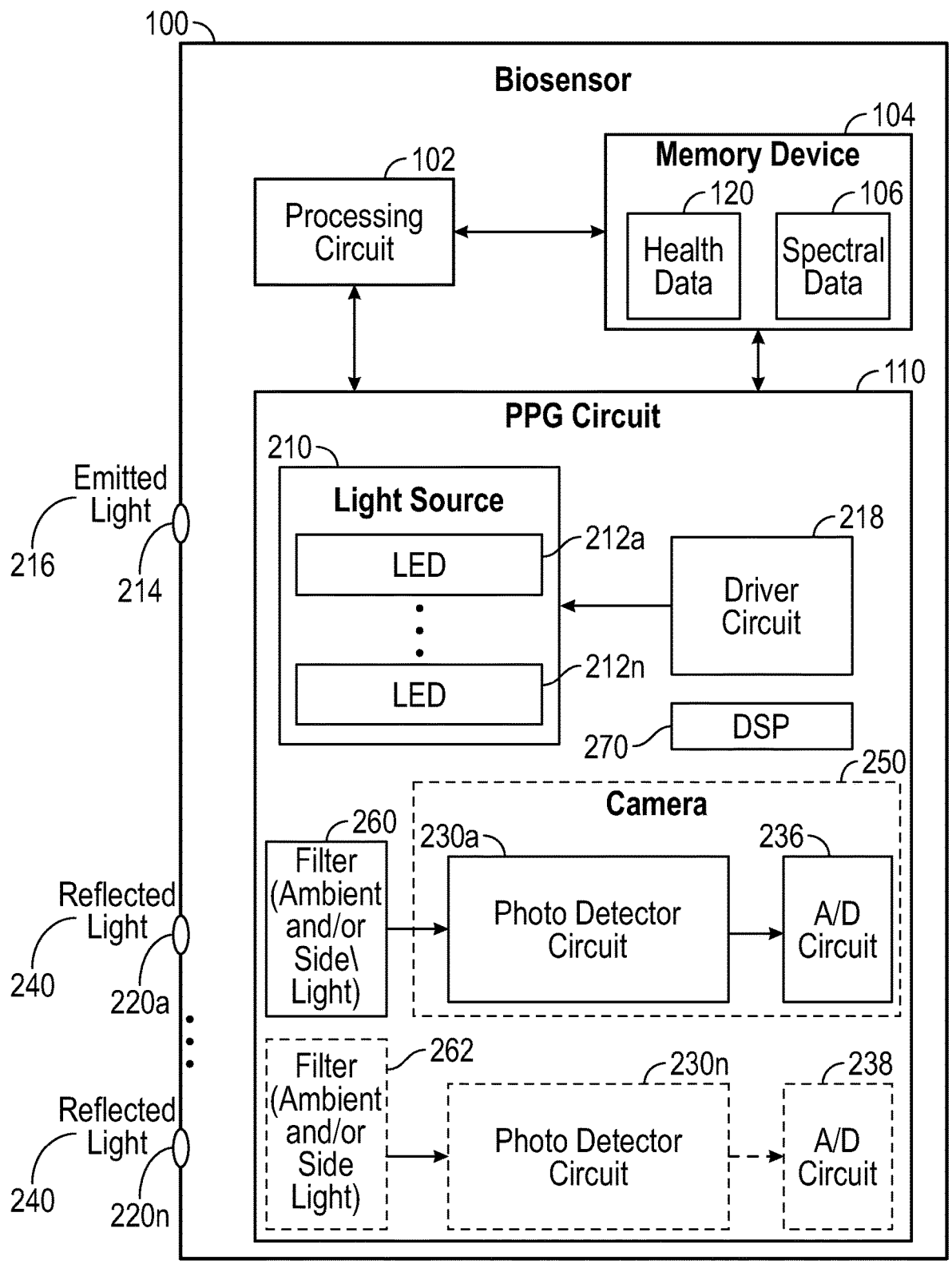
FIG. 2 illustrates a schematic block diagram of an embodiment of the PPG circuit in more detail.

FIG. 2 illustrates a schematic block diagram of an embodiment of the PPG circuit 110 in more detail. The PPG circuit 110 includes a light source 210 configured to emit a plurality of wavelengths of light across various spectrums. The plurality of LEDs 212a-n are configured to emit light in one or more spectrums, including infrared (IR) light, ultraviolet (UV) light, near IR light or visible light, in response to driver circuit 218. For example, the biosensor 100 may include a first LED 212a that emits visible light and a second LED 212b that emits infrared light and a third LED 212c that emits UV light, etc. In another embodiment, one or more of the light sources 210 may include tunable LEDs or lasers operable to emit light over one or more frequencies or ranges of frequencies or spectrums in response to driver circuit 218.

In an embodiment, the driver circuit 218 is configured to control the one or more LEDs 212a-n to generate light at one or more frequencies for predetermined periods of time. The driver circuit 218 may control the LEDs 212a-n to operate concurrently or consecutively. The driver circuit 218 is configured to control a power level, emission period and frequency of emission of the LEDs 212a-n. The driver circuit 218 may also tune a wavelength output of the LEDs 212a-n in response to a temperature or other feedback. The biosensor 100 is thus configured to emit one or more wavelengths of light in one or more spectrums that is directed at the surface or epidermal layer of the skin tissue of a user. The emitted light 216 passes through at least one aperture 214 and towards the surface or epidermal layer of the skin tissue of a user.

The PPG circuit 110 further includes one or more photodetector circuits 230a-n. The photodetector circuits 230 may be implemented as part of a camera 250. For example, a first photodetector circuit 230 may be configured to detect visible light and the second photodetector circuit 230 may be configured to detect IR light. Alternatively, a single photodetector 230 may be implemented to detect light across multiple spectrums. When multiple photodetectors 230 are implemented, the detected signals obtained from each of the photodetectors may be added or averaged. Alternatively, a detected light signal with more optimal signal to noise ration may be selected from the multiple photodetector circuits 230a-n.

The first photodetector circuit 230a and the second photodetector circuit 230n may also include a first filter 260 and a second filter 262 configured to filter ambient light and/or scattered light. For example, in some embodiments, only light reflected at an approximately perpendicular angle to the skin surface of the user is desired to pass through the filters. The first photodetector circuit 230a and the second photodetector circuit 230n are coupled to a first analog to digital (A/D) circuit 236 and a second A/D circuit 238. Alternatively, a single A/D circuit may be coupled to each of the photodetector circuits 230a-n. The A/D circuits convert the spectral responses to digital spectral data for processing by a DSP or other processing circuit.

The one or more photodetector circuits 230a-n include one or more types of spectrometers or photodiodes or other types of light detection circuits configured to detect an intensity of light as a function of wavelength over a time period to obtain a spectral response. In use, the one or more photodetector circuits 230a-n detect the intensity of reflected light 240 from skin tissue of a user that enters one or more apertures 220a-n of the biosensor 100. In another example, the one or more photodetector circuits 230a-n detect the intensity of light due to transmissive absorption (e.g., light transmitted through tissues, such as a fingertip or ear lobe). The one or more photodetector circuits 230a-n then obtain a spectral response (a PPG signal) of the reflected or transmissive light by measuring an intensity of the light at one or more wavelengths over a period of time.

In another embodiment, the light source 210 may include a broad spectrum light source, such as a white light to infrared (IR) or near IR LED, that emits light with wavelengths across multiple spectrums, e.g. from 350 nm to 2500 nm. Broad spectrum light sources with different ranges may be implemented. In an aspect, a broad spectrum light source is implemented with a range across 100 nm wavelengths to 2000 nm range of wavelengths in the visible, IR and/or UV frequencies. For example, a broadband tungsten light source for spectroscopy may be used. The spectral response of the reflected light 240 is then measured across the wavelengths in the broad spectrum, e.g. from 350 nm to 2500 nm, concurrently. In an aspect, a charge coupled device (CCD) spectrometer may be configured in the photodetector circuit 230 to measure the spectral response of the detected light over the broad spectrum.

The PPG circuit 110 may also include a digital signal processing (DSP) circuit 270 that includes signal processing of the digital spectral data. For example, the DSP circuit may determine AC or DC components from the spectral responses (PPG signals) or diastolic and systolic points or other spectral data 106. The spectral data may then be processed by the processing circuit 102 to obtain health data 120 of a user. The spectral data 106 may alternatively or in additionally be transmitted by the biosensor 100 to a central control module for processing to obtain health data 120 of a user. The spectral data 106, PPG signals, etc. may be stored in the memory device 104 of the biosensor 100.

In use, the biosensor 100 performs PPG techniques using the PPG circuit 110 to detect the concentration levels of one or more substances in blood flow. In one aspect, the biosensor 100 receives reflected light or transmissive light from skin tissue to obtain a spectral response. The spectral response includes a spectral curve that illustrates an intensity or power or energy at a frequency or wavelength in a spectral region of the detected light over a period of time. The ratio of the resonance absorption peaks from two different frequencies can be calculated and based on the Beer-Lambert law used to obtain the levels of substances in the blood flow.

For example, one or more of the embodiments of the biosensor 100 described herein is configured to detect a concentration level of one or more substances within blood flow using PPG techniques. For example, the biosensor 100 may detect nitric oxide (NO) concentration levels and correlate the NO concentration level to a blood glucose level. The biosensor 100 may also detect oxygen saturation (SaO2 or SpO2) levels in blood flow. The biosensor may also be configured to detect a liver enzyme cytochrome oxidase (P450) enzyme and correlate the P450 concentration level to a blood alcohol level.

The spectral response of a substance or substances in the arterial blood flow is determined in a controlled environment, so that an absorption coefficient $\alpha_{g1}$ can be obtained at a first light wavelength $\lambda 1$ and at a second wavelength $\lambda 2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined. For example, the concentration Cg may be obtained from the following equations:

At the first wavelength $\lambda_1, I_1 = I_{in1} * 10^{-(\alpha_{g1} C_{gw} + \alpha_{w1} C_w)*l}$ At the second wavelength $\lambda_2, I_2 = I_{in2} * 10^{-(\alpha_{g2} C_{gw} + \alpha_{w2} C_w)*l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10 \left(\frac{I1}{Iin1}\right)}{\log 10 \left(\frac{I2}{Iin2}\right)}$$

The concentration of the substance Cg may then be equal to:

$$Cg = \frac{Cgw}{Cgw + Cw} = \frac{\alpha_{w2} R - \alpha_{w1}}{(\alpha_{w2} - \alpha_{gw2}) * R - (\alpha_{w1} - \alpha_{gw1})}$$

The biosensor 100 may thus determine the concentration of various substances in arterial blood flow from the Beer-Lambert principles using the spectral responses of at least two different wavelengths.

Figure 3:
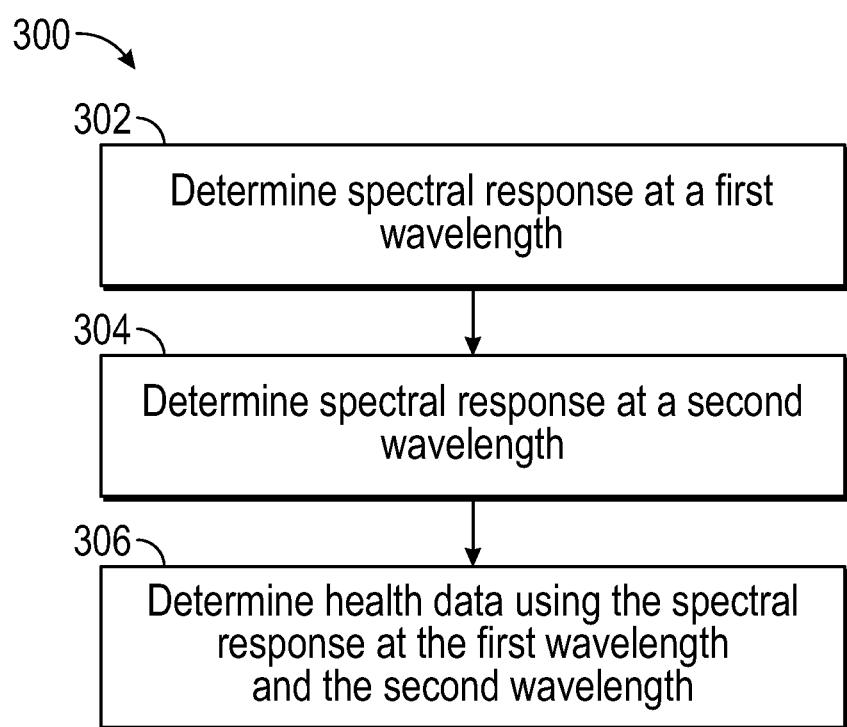
FIG. 3 illustrates a logical flow diagram of an embodiment of a method for determining concentration level of a substance in blood flow using Beer-Lambert principles.

FIG. 3 illustrates a logical flow diagram of an embodiment of a method 300 for determining concentration level of a substance in blood flow using Beer-Lambert principles. The biosensor 100 transmits light at a first predetermined wavelength and at a second predetermined wavelength. The biosensor 100 detects the light (reflected from the skin or transmitted through the skin) and determines the spectral response at the first wavelength at 302 and at the second wavelength at 304. The biosensor 100 then determines health data, such as an indicator or concentration level of substances in blood flow, using the spectral responses of the first and second wavelength at 306. In general, the first predetermined wavelength is selected that has a high absorption coefficient for the substance in blood flow while the second predetermined wavelength is selected that has a lower absorption coefficient for the substance in blood flow. Thus, it is generally desired that the spectral response for the first predetermined wavelength have a higher intensity level in response to the substance than the spectral response for the second predetermined wavelength.

In an embodiment, the biosensor 100 may detect a concentration level of nitric oxide (NO) in blood flow using a first predetermined wavelength in a range of 380-410 nm and in particular at 390 nm or 395 nm. In another aspect, the biosensor 100 may transmit light at the first predetermined wavelength in a range of approximately 1 nm to 50 nm around the first predetermined wavelength. Similarly, the biosensor 100 may transmit light at the second predetermined wavelength in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted by NO may spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated at 302 and 304. The biosensor 100 analyzes the first and second spectral responses to detect an indicator or concentration level of NO in the arterial blood flow at 306. In another embodiment, using absorption coefficients for both Nitric Oxide and Hemoglobin, the concentration of Nitric Oxide can be obtained in arterial blood. A calibration table using human subjects may then correlate amounts of glucose (mG/DL) in relation to R values (NoHb) 404/940 nm.

In another example, the biosensor 100 may also detect vitals, such as heart rate, respiration rate and pulse pressure. The biosensor 100 may also determine a level of vasodilation and a period of vasodilation as described in more detail herein. Because blood flow to the skin can be modulated by multiple other physiological systems, the biosensor 100 may also be used to monitor arterial health, such as hypovolemia or other circulatory conditions.

Photoplethysmography (PPG) is used to measure time-dependent volumetric properties of blood in blood vessels due to the cardiac cycle. For example, the heartbeat affects the volume of blood flow and the concentration or absorption levels of substances being measured in the arterial blood flow. Over a cardiac cycle, pulsating arterial blood changes the volume of blood flow in a blood vessel. Incident light $I_O$ is directed at a tissue site and a certain amount of light is reflected or transmitted and a certain amount of light is absorbed. At a peak of blood flow or volume in a cardiac cycle, the reflected/transmitted light $I_L$ is at a minimum due to absorption by the increased blood volume, e.g., due to the pulsating blood in the vessel. At a minimum of blood volume during the cardiac cycle, the transmitted/reflected light $I_H$ 416 is at a maximum due to lack of absorption from the pulsating blood.

The biosensor 100 is configured to filter the reflected/transmitted light $I_L$ of the pulsating blood from the transmitted/reflected light $I_H$. This filtering isolates the light due to reflection/transmission of the pulsating blood from the light due to reflection/transmission from non-pulsating blood, vessel walls, surrounding tissue, etc. The biosensor 100 may then measure the concentration levels of one or more substances from the reflected/transmitted light $I_L$ 814 in the pulsating blood.

For example, incident light $I_O$ is directed at a tissue site at one or more wavelengths. The reflected/transmitted light I is detected by a photodetector or sensor array in a camera. At a peak of blood flow or volume, the reflected light $I_L$ 414 is at a minimum due to absorption by the pulsating blood, non-pulsating blood, other tissue, etc. At a minimum of blood flow or volume during the cardiac cycle, the Incident or reflected light $I_H$ 416 is at a maximum due to lack of absorption from the pulsating blood volume. Since the light I is reflected or traverses through a different volume of blood at the two measurement times, the measurement provided by a PPG sensor is said to be a 'volumetric measurement' descriptive of the differential volumes of blood present at a certain location within the user's vessels at different times during the cardiac cycle. These principles described herein may be applied to venous blood flow and arterial blood flow.

In general, the relative magnitudes of the AC and DC contributions to the reflected/transmitted light signal I may be determined. In general, AC contribution of the reflected light signal I is due to the pulsating blood flow. A difference function may thus be computed to determine the relative magnitudes of the AC and DC components of the reflected light I to determine the magnitude of the reflected light due to the pulsating blood flow. The described techniques herein for determining the relative magnitudes of the AC and DC contributions is not intended as limiting. It will be appreciated that other methods may be employed to isolate or otherwise determine the relative magnitude of the light $I_L$ due to pulsating blood flow (arterial and/or venous).

In one aspect, the spectral response obtained at each wavelength may be aligned based on the systolic 402 and diastolic 404 points in their respective spectral responses. This alignment is useful to associate each spectral response with a particular stage or phase of the pulse-induced local pressure wave within the blood vessel (which roughly mimics the cardiac cycle 406 and thus include systolic and diastolic stages and sub-stages thereof). This temporal alignment helps to determine the absorption measurements acquired near a systolic point in time of the cardiac cycle and near the diastolic point in time of the cardiac cycle 406 associated with the local pressure wave within the user's blood vessels. This measured local pulse timing information may be useful for properly interpreting the absorption measurements in order to determine the relative contributions of the AC and DC components measured by the biosensor 100. So, for one or more wavelengths, the systolic points 402 and diastolic points 404 in the spectral response are determined. These systolic points 402 and diastolic pointsv 404 for the one or more wavelengths may then be aligned as a method to discern concurrent responses across the one or more wavelengths.

Figure 4:
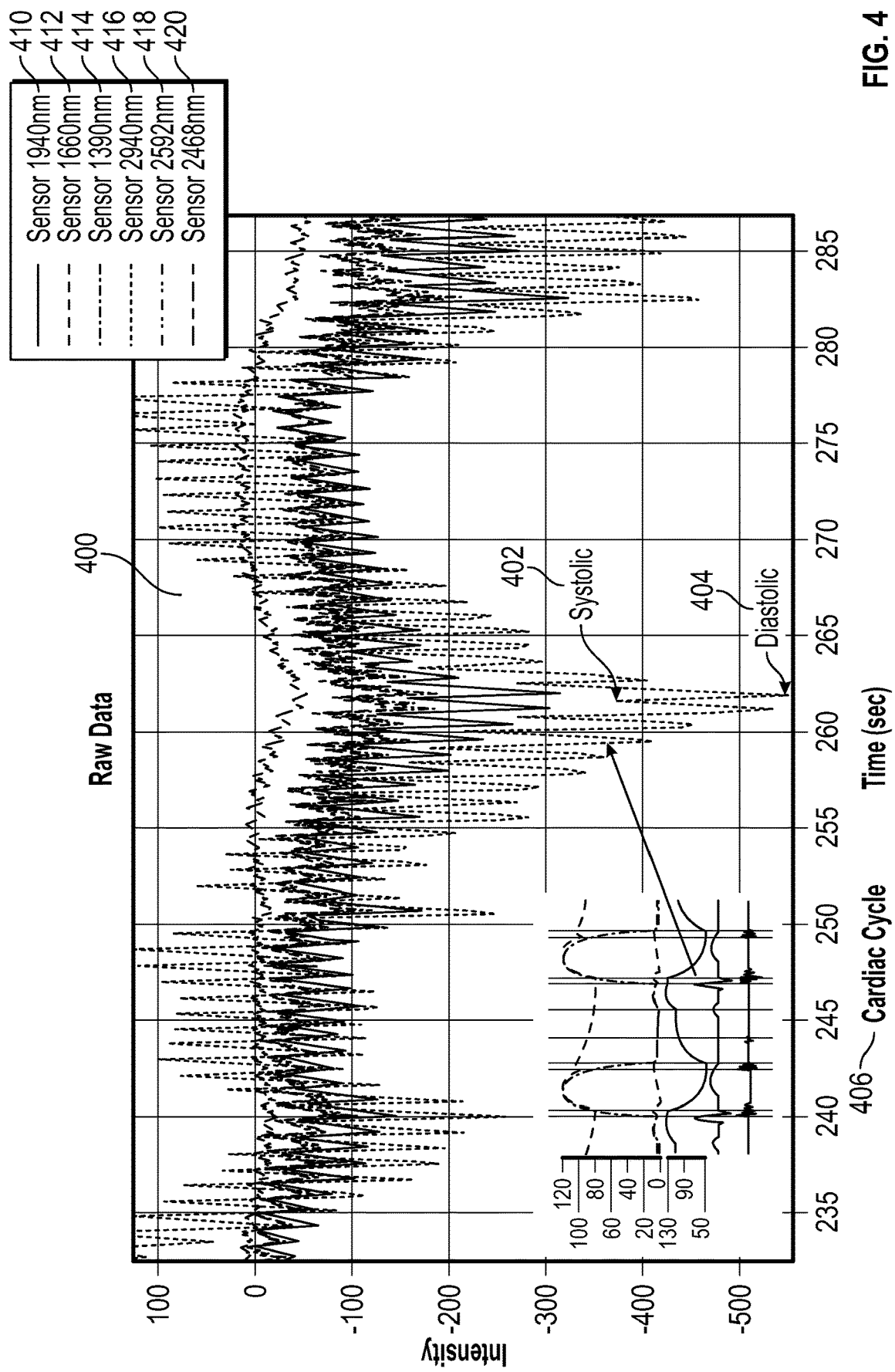
FIG. 4 illustrates the spectral response obtained at the plurality of wavelengths with the systolic points and diastolic points aligned over a cardiac cycle.

In another embodiment, the systolic points 402 and diastolic points 404 in the absorbance measurements are temporally correlated to the pulse-driven pressure wave within the blood vessels—which may differ from the cardiac cycle. In another embodiment, the biosensor 100 may concurrently measure the intensity reflected at each the plurality of wavelengths. Since the measurements are concurrent, no alignment of the spectral responses of the plurality of wavelengths may be necessary. FIG. 4 illustrates the spectral response obtained at the plurality of wavelengths with the systolic points 402 and diastolic points 404 aligned over a cardiac cycle 406.

Figure 5:
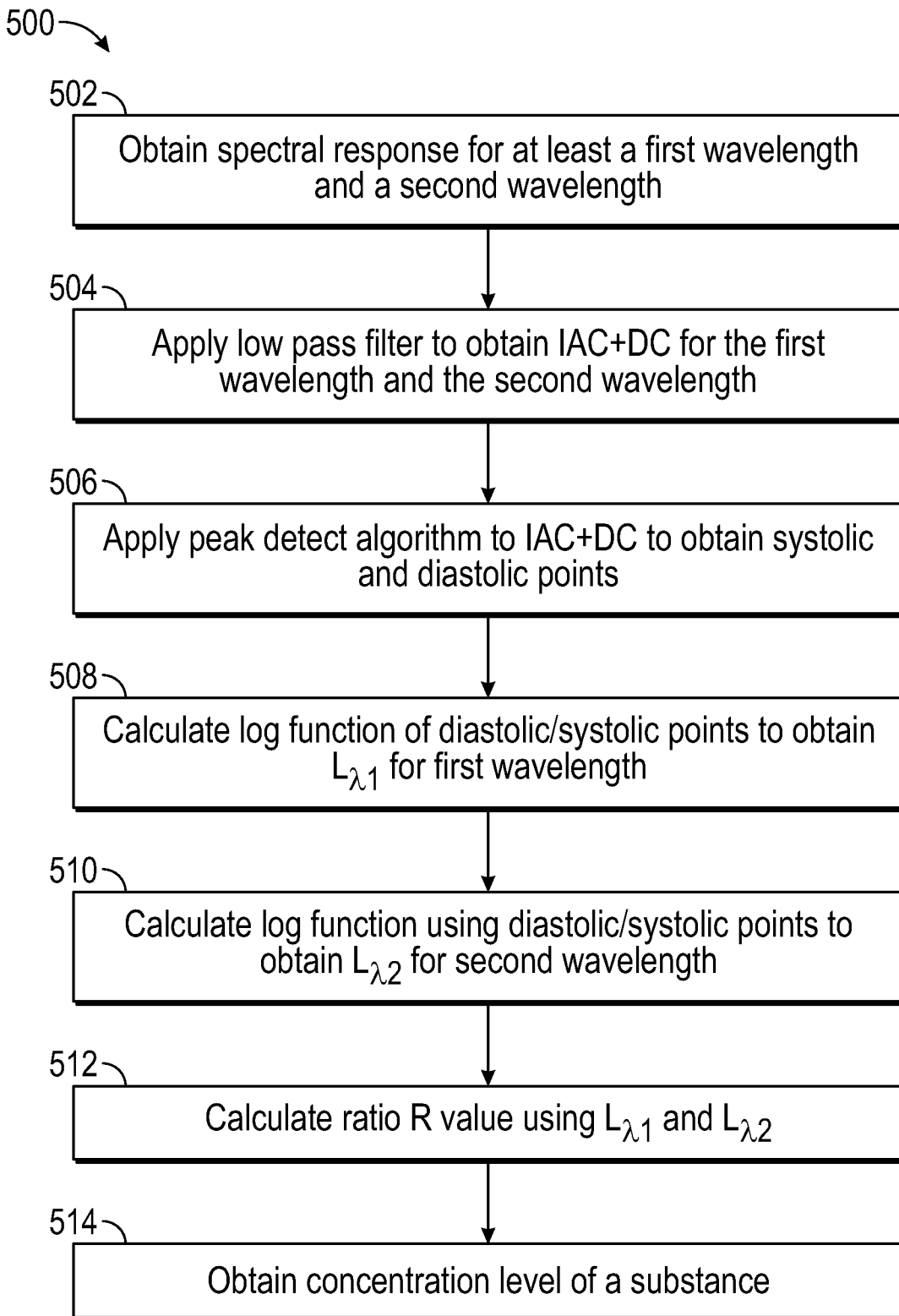
FIG. 5 illustrates a logical flow diagram of an embodiment of a method of the biosensor.

FIG. 5 illustrates a logical flow diagram of an embodiment of a method 500 of the biosensor 100. In one aspect, the biosensor 100 emits and detects light at a plurality of predetermined frequencies or wavelengths, such as approximately 940 nm, 660 nm, 390 nm, 592 nm, and 468 nm or in ranges thereof. The light is pulsed for a predetermined period of time (such as 100 usec or 200 Hz) sequentially or simultaneously at each predetermined wavelength. In another aspect, light may be pulsed in a wavelength range of 1 nm to 50 nm around each of the predetermined wavelengths. For example, for the predetermined wavelength 390 nm, the biosensor 100 may transmit light directed at skin tissue of the user in a range of 360 nm to 410 nm including the predetermined wavelength 390 nm. For the predetermined wavelength of 940 nm, the biosensor 100 may transmit light directed at the skin tissue of the user in a range of 920 nm to 975 nm. In another embodiment, the light is pulsed simultaneously at least at each of the predetermined wavelengths (and in a range around the wavelengths).

The spectral responses are obtained around the plurality of wavelengths, including at least a first wavelength and a second wavelength at 502. The spectral responses may be measured over a predetermined period (such as 300 usec.) or at least over 2-3 cardiac cycles. This measurement process is repeated continuously, e.g., pulsing the light at 10-100 Hz and obtaining spectral responses over a desired measurement period, e.g. from 1-2 seconds to 1-2 minutes or from 2-3 hours to continuously over days or weeks. The spectral data obtained by the PPG circuit 110, such as the digital or analog spectral responses, may be processed locally by the biosensor 100 or transmitted to a central control module for processing.

The systolic and diastolic points of the spectral response are then determined. Because the human pulse is typically on the order of magnitude of one 1 Hz, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period. The spectral responses are obtained over one or more cardiac cycles and systolic and diastolic points of the spectral responses are determined. Preferably, the spectral response is obtained over at least three cardiac cycles in order to obtain a heart rate.

A low pass filter (such as a 5 Hz low pass filter) is applied to the spectral response signal at 504. The relative contributions of the AC and DC components are obtained $I_{AC+DC}$ and $I_{AC}$. A peak detection algorithm is applied to determine the systolic and diastolic points at 506. If not detected concurrently, the systolic and diastolic points of the spectral response for each of the wavelengths may be aligned or may be aligned with systolic and diastolic points of a pressure pulse waveform or cardiac cycle.

Beer Lambert equations are then applied as described herein. For example, the $L_\lambda$ values are then calculated for the first wavelength $\lambda_1$ at 508 and the second wavelength $\lambda_2$ at 510, wherein the $L_\lambda$ values for a wavelength equals:

$$L_\lambda = \text{Log}10\left(\frac{IAC + DC}{IDC}\right)$$

wherein $I_{AC+DC}$ is the intensity of the detected light with AC and DC components and $I_{DC}$ is the intensity of the detected light with the AC component filtered by the low pass filter. The value $L_\lambda$ isolates the spectral response due to pulsating arterial blood flow, e.g. the AC component of the spectral response.

A ratio R of the $L_\lambda$ values at two wavelengths may then be determined at 512. For example, the ratio R may be obtained from the following:

$$\text{Ratio } R = \frac{L\lambda 1}{L\lambda 2}$$

The spectral responses may be measured and the $L_\lambda$ values and Ratio R determined continuously, e.g. every 1-2 seconds, and the obtained $L_\lambda$ values and/or Ratio R averaged over a predetermined time period, such as over 1-2 minutes. The concentration level of a substance may then be obtained from the R value and a calibration database at 514. The biosensor 100 may continuously monitor a user over 2-3 hours or continuously over days or weeks.

In one embodiment, the $R_{390,940}$ value with $L_{\lambda 1=390\,nm}$ and $L_2=_{940}$ may be non-invasively and quickly and easily obtained using the biosensor 100 to determine a concentration level of nitric oxide NO in blood flow of a user. In particular, in unexpected results, it is believed that the nitric oxide NO levels in the blood flow is being measured at least in part by the biosensor 100 at wavelengths in the range of 380-410 and in particular at $\lambda_1=390$ nm. Thus, the biosensor 100 measurements to determine the $L_{390\,nm}$ values are the first time NO concentration levels in arterial blood flow have been measured directly in vivo. These and other aspects of the biosensor 100 are described in more detail herein with clinical trial results.

Figure 6:
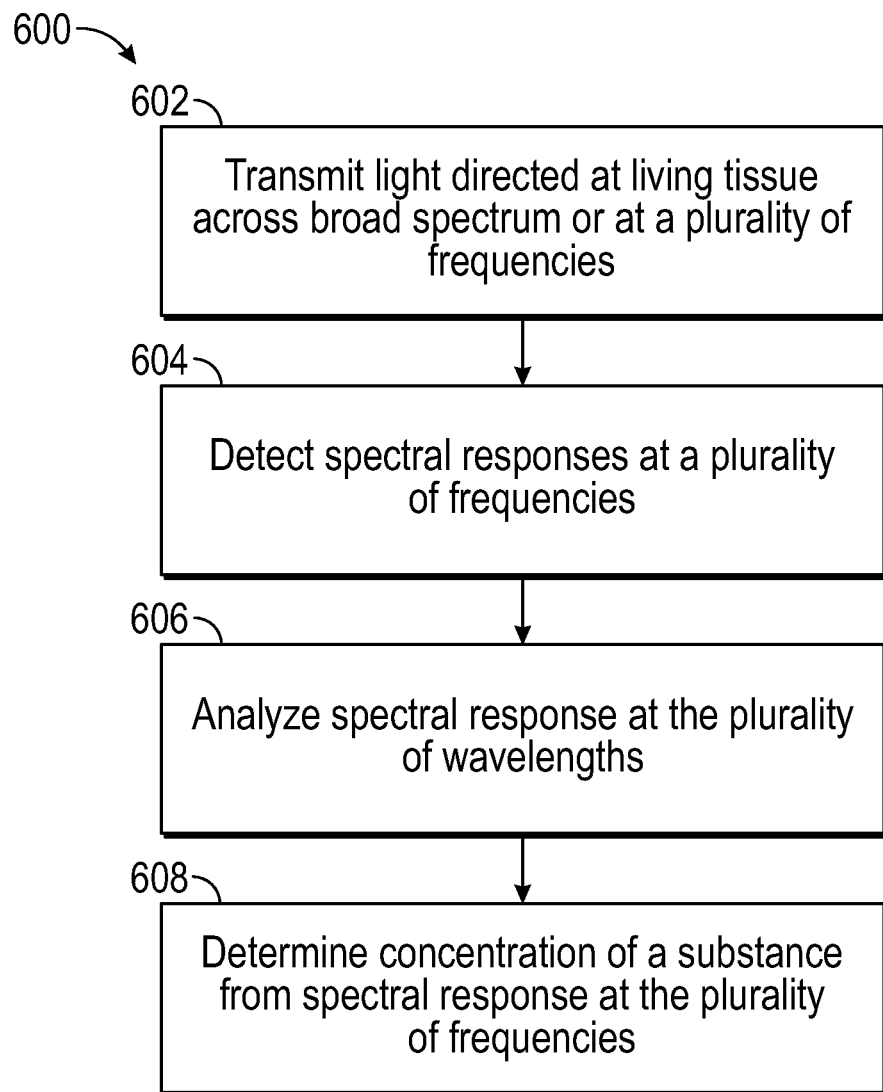
FIG. 6 illustrates a logical flow diagram of an exemplary method to determine levels of a substance in blood flow using the PPG signals at a plurality of wavelengths.

Embodiment—Determination of Concentration Level of a Substance Using PPG Signals at a Plurality of Wavelengths FIG. 6 illustrates a logical flow diagram of an exemplary method 600 to determine levels of a substance in blood flow using the PPG signals at a plurality of wavelengths. The absorption coefficient of a substance may be sufficiently higher at a plurality of wavelengths, e.g. due to isoforms or derivative compounds. For example, the increased intensity of light at a plurality of wavelengths may be due to reflectance by isoforms or other compounds in the arterial blood flow. Another method for determining the concentration levels may then be used by measuring the spectral responses and determining L and R values at a plurality of different wavelengths of light. In this example then, the concentration level of the substance is determined using spectral responses at multiple wavelengths. An example for calculating the concentration of a substance over multiple wavelengths may be performed using a linear function, such as is illustrated herein below.

$$LN(I_{1-n}) = \Sigma_{i=0}^{n} \mu i * Ci$$

wherein, $I_{1-n}$=intensity of light at wavelengths $\lambda_{1-n}$ $\mu_n$=absorption coefficient of substance 1, 2, ... n at wavelengths $\mu_{1-n}$ $C_n$=Concentration level of substance 1, 2, ... n When the absorption coefficients $\mu_{1-n}$ of a substance, its isoforms or other compounds including the substance are known at the wavelengths $\lambda_{1-n}$, then the concentration level C of the substances may be determined from the spectral responses at the wavelengths $\lambda_{1-n}$ (and e.g., including a range of 1 nm to 50 nm around each of the wavelengths). The concentration level of the substance may be isolated from the isoforms or other compounds by compensating for the concentration of the compounds. Thus, using the spectral responses at multiple frequencies provides a more robust determination of the concentration level of a substance.

In use, the biosensor 100 transmits light directed at skin tissue at a plurality of wavelengths or over a broad spectrum at 602. The spectral response of light from the skin tissue is detected at 604, and the spectral responses are analyzed at a plurality of wavelengths (and in one aspect including a range of +/−10 to 50 nm around each of the wavelengths) at 606. Then, the concentration level C of the substance may be determined using the spectral responses at the plurality of wavelengths at 608. The concentration level of the substance may be isolated from isoforms or other compounds by compensating for the concentration of the compounds. For example, using absorption coefficients for Nitric Oxide and Hemoglobin, the concentration of Nitric Oxide can be obtained in arterial blood. A calibration table using human subjects may then to correlate amounts of glucose (mG/DL) in relation to R values (NoHb) 404/940 nm.

Figure 7:
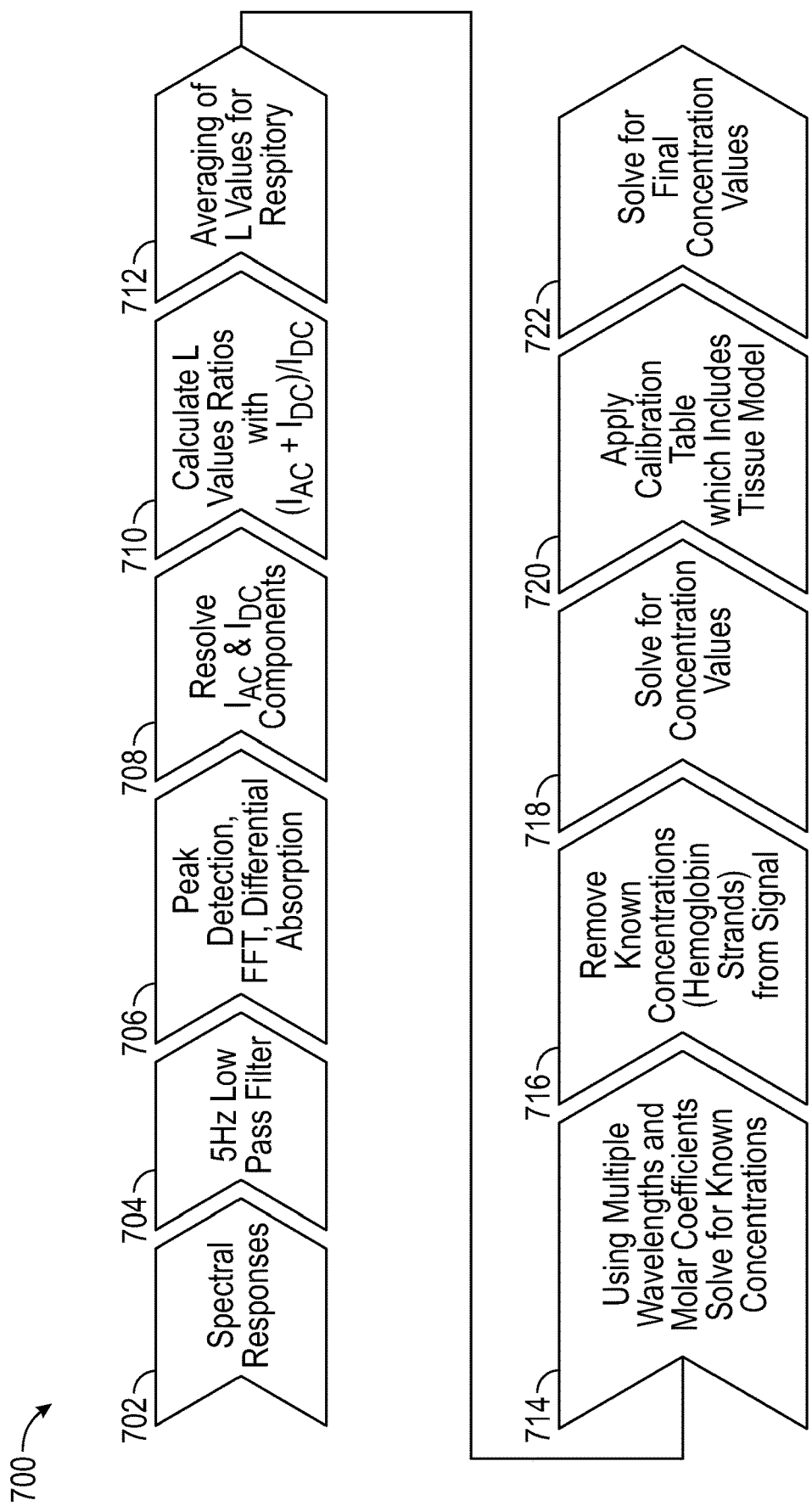
FIG. 7 illustrates a logical flow diagram of an exemplary method to determine levels of a substance using the spectral responses at a plurality of wavelengths in more detail.

FIG. 7 illustrates a logical flow diagram of an exemplary method 700 to determine levels of a substance using the spectral responses at a plurality of wavelengths in more detail. The spectral responses are obtained at 702. The spectral response signals include AC and DC components $T_{AC+DC}$. A low pass filter (such as a 5 Hz low pass filter) is applied to each of the spectral response signals $I_{AC+DC}$ to isolate the DC component of each of the spectral response signals $I_{DC}$ at 704. The AC fluctuation is due to the pulsatile expansion of the vessels due to the volume increase in pulsating blood. In order to measure the AC fluctuation, measurements are taken at different times and a peak detection algorithm is used to determine the diastolic point and the systolic point of the spectral responses at 706. A Fast Fourier transform (FFT) algorithm may also be used to isolate the DC component $I_{DC}$ and AC component of each spectral response signal at 706. A differential absorption technique may also be used as described in more detail herein. The $I_{DC}$ component is thus isolated from the spectral signal at 708.

The $I_{AC+DC}$ and $I_{DC}$ components are then used to compute the L values at 710. For example, a logarithmic function may be applied to the ratio of $I_{AC+DC}$ and $I_{DC}$ to obtain an L value for each of the wavelengths $L_{\lambda 1-n}$. Since the respiratory cycle affects the PPG signals, the L values may be averaged over a respiratory cycle and/or over another predetermined time period (such as over a 1-2 minute time period) or over a plurality of cardiac cycles at 712.

In an embodiment, isoforms of a substance may be attached in the blood stream to one or more types of hemoglobin compounds. The concentration level of the hemoglobin compounds may then need to be accounted for to isolate the concentration level of the substance from the hemoglobin compounds. For example, nitric oxide (NO) is found in the blood stream in a gaseous form and also attached to hemoglobin compounds. Thus, the spectral responses obtained around 390 nm (+/−20 nm) may include a concentration level of the hemoglobin compounds as well as nitric oxide. The hemoglobin compound concentration levels must thus be compensated for to isolate the nitric oxide concentration levels. Multiple wavelengths and absorption coefficients for hemoglobin are used to determine a concentration of the hemoglobin compounds at 714. Other methods may also be used to obtain a concentration level of hemoglobin in the blood flow as well. The concentration of the hemoglobin compounds is then adjusted from the measurements at 716. The concentration values of the substance may then be obtained at 718. For example, the R values are then determined at 718.

To determine a concentration level of the substance, a calibration table or database is used that associates the obtained R value to a concentration level of the substance at 720. The calibration database correlates the R value with a concentration level. The calibration database may be generated for a specific user or may be generated from clinical data of a large sample population. For example, it is determined that the R values should correlate to similar NO concentration levels across a large sample population. Thus, the calibration database may be generated from testing of a large sample of a general population to associate R values and NO concentration levels.

In addition, the R values may vary depending on various factors, such as underlying skin tissue. For example, the R values may vary for spectral responses obtained from an abdominal area versus measurements from a wrist or finger due to the varying tissue characteristics. The calibration database may thus provide different correlations between the R values and concentration levels of a substance depending on the underlying skin tissue characteristics. The concentration level of the substance in blood flow is then obtained using the calibration table at 722. The concentration level may be expressed as mmol/liter, as a saturation level percentage, as a relative level on a scale, etc.

Embodiment—Determination of Concentration Levels of a Substance Using Shifts in Absorbance Peaks In another embodiment, a concentration level of a substance may be obtained from measuring a characteristic shift in an absorbance peak of hemoglobin. For example, the absorbance peak for methemoglobin shifts from around 433 nm to 406 nm in the presence of NO. The advantage of the measurement of NO by monitoring methemoglobin production includes the wide availability of spectrophotometers, avoidance of sample acidification, and the relative stability of methemoglobin. Furthermore, as the reduced hemoglobin is present from the beginning of an experiment, NO synthesis can be measured continuously, removing the uncertainty as to when to sample for NO.

The biosensor 100 may detect nitric oxide in vivo using PPG techniques by measuring the shift in the absorbance spectra curve of reduced hemoglobin in tissue and/or arterial blood flow. The absorbance spectra curve shifts with a peak from around 430 nm to a peak around 411 nm depending on the production of methemoglobin. The greater the degree of the shift of the peak of the curve, the higher the production of methemoglobin and NO concentration level. Correlations may be determined between the degree of the measured shift in the absorbance spectra curve of reduced hemoglobin to a concentration level of NO. The correlations may be determined from a large sample population or for a particular user and stored in a calibration database. The biosensor 100 may thus obtain an NO concentration level by measuring the shift of the absorbance spectra curve of reduced hemoglobin. A similar method of determining shifts in absorbance spectra may be implemented to determine a blood concentration level of other substances.

The biosensor 100 may obtain an NO concentration level by measuring the shift of the absorbance spectra curve of deoxygenated hemoglobin and/or by measuring the shift of the absorbance spectra curve of oxygenated hemoglobin in vivo. The biosensor 100 may then access a calibration database that correlates the measured shift in the absorbance spectra curve of deoxygenated hemoglobin to an NO concentration level. Similarly, the biosensor may access a calibration database that correlates the measured shift in the absorbance spectra curve of oxygenated hemoglobin to an NO concentration level.

Figure 8:
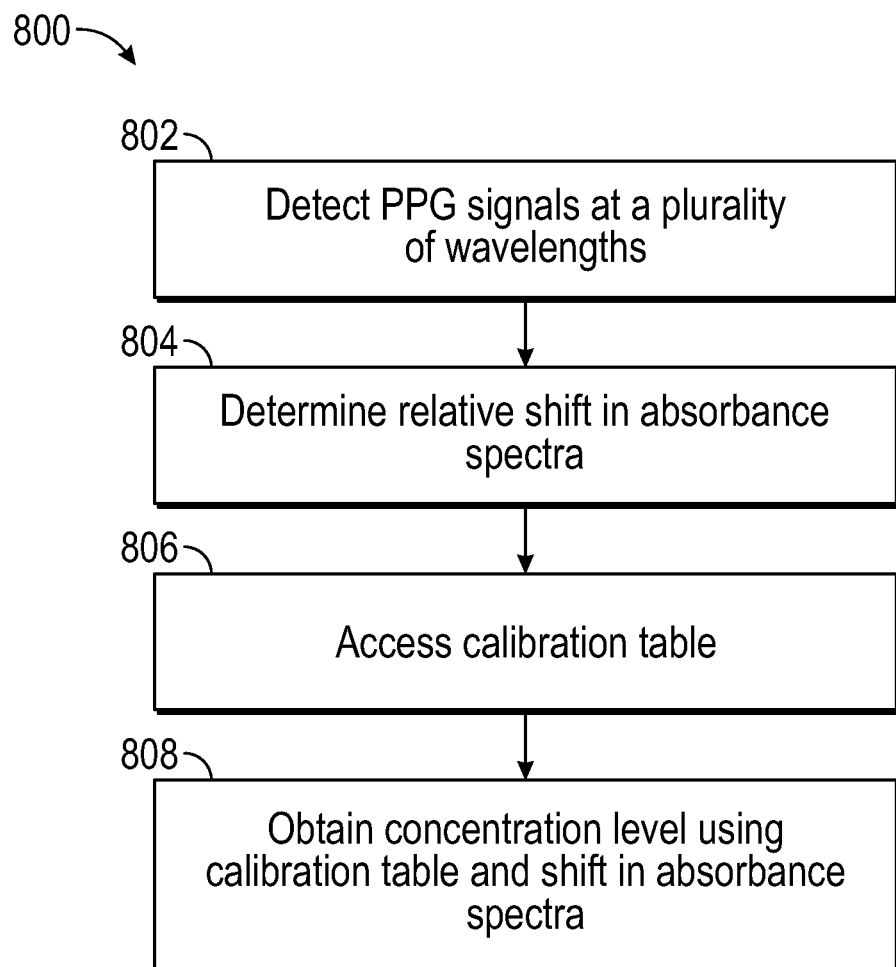
FIG. 8 illustrates a logical flow diagram of an exemplary embodiment of a method for measuring a concentration level of a substance in vivo using shifts in absorbance spectra.

FIG. 8 illustrates a logical flow diagram of an exemplary embodiment of a method 800 for measuring a concentration level of a substance in vivo using shifts in absorbance spectra. The biosensor 100 may obtain a concentration of the substance by measuring shifts in absorbance spectra of one or more substances that interact with the substance. For example, the one or more substances may include oxygenated and deoxygenated hemoglobin (HB). The PPG circuit 110 detects PPG signals at a plurality of wavelengths with a high absorption coefficient of the one or more substances that interact with the substance at 802. The biosensor 100 determines the relative shift in the absorbance spectra for the substance at 804. For example, the biosensor 100 may measure the absorbance spectra curve of deoxygenated HB and determine its relative shift or peak between the range of approximately 430 nm and 405 nm. In another example, the biosensor 100 may measure the absorbance spectra curve of oxygenated HB and determine its relative shift or peak between 421 nm and 393 nm.

The biosensor 100 accesses a calibration database that correlates the relative shift in the absorbance spectra of the substance with a concentration level of the substance at 806. The biosensor 100 may thus obtain a concentration level of the substance in blood flow using a calibration database and the measured relative shift in absorbance spectra at 808.

The various methods thus include one or more of: Peak & Valley (e.g., peak detection), FFT, and differential absorption. Each of the methods require different amounts of computational time which affects overall embedded computing time for each signal, and therefore can be optimized and selectively validated with empirical data through large clinical sample studies. The biosensor 100 may use a plurality of these methods to determine a plurality of values for the concentration level of the substance. The biosensor 100 may determine a final concentration value using the plurality of values. For example, the biosensor 100 may average the values, obtain a mean of the values, etc.

The biosensor 100 may be configured for measurement on a fingertip or palm, wrist, an arm, forehead, chest, abdominal area, ear lobe, or other area of the skin or body or living tissue. The characteristics of underlying tissue vary depending on the area of the body, e.g. the underlying tissue of an abdominal area has different characteristics than the underlying tissue at a wrist. The operation of the biosensor 100 may need to be adjusted in response to its positioning due to such varying characteristics of the underlying tissue. The PPG circuit 110 may adjust a power of the LEDs or a frequency or wavelength of the LEDs based on the underlying tissue. The biosensor 100 may adjust processing of the data. For example, an absorption coefficient may be adjusted when determining a concentration level of a substance based on Beer-Lambert principles due to the characteristics of the underlying tissue.

In addition, the calibrations utilized by the biosensor 100 may vary depending on the positioning of the biosensor. For example, the calibration database may include different table or other correlations between R values and concentration level of a substance depending on position of the biosensor. Due to the different density of tissue and vessels, the R value obtained from measurements over an abdominal area may be different than measurements over a wrist or forehead or fingertip. The calibration database may thus include different correlations of the R value and concentration level depending on the underlying tissue. Other adjustments may also be implemented in the biosensor 100 depending on predetermined or measured characteristics of the underlying tissue of the body part.

Embodiment—Respiration Rate, Heart Rate and Pulse Pressure

Figure 9:
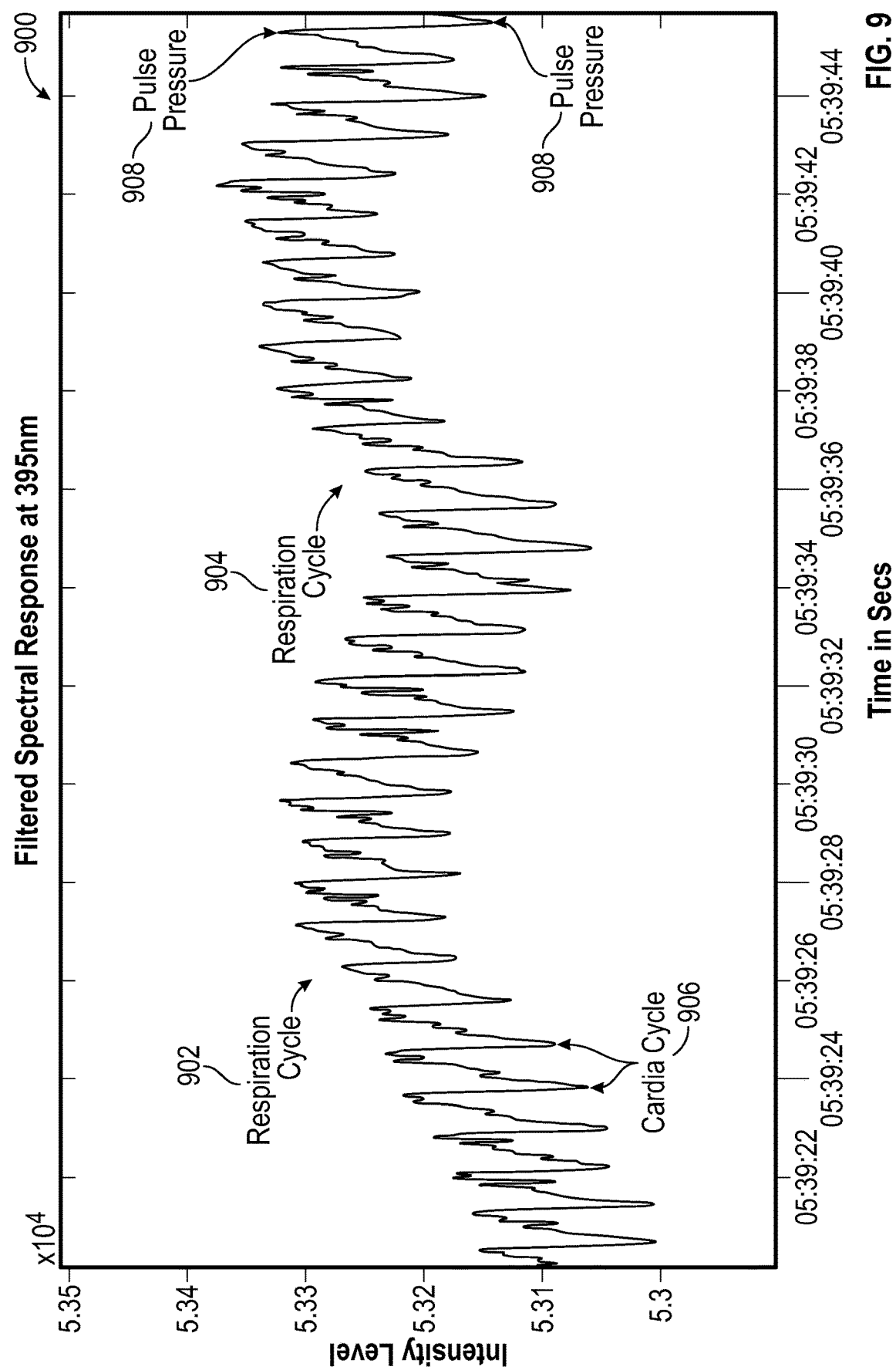
FIG. 9 illustrates a schematic drawing of an exemplary embodiment of a spectral response obtained using an embodiment of the biosensor.

FIG. 9 illustrates a schematic drawing of an exemplary embodiment of a PPG Signal 900 obtained using an embodiment of the biosensor 100 from a user. The PPG Signal 900 was obtained at a wavelength of around 395 nm and is illustrated for a time period of about 40 seconds. The PPG Signal 900 was filtered using digital signal processing techniques to eliminate noise and background interference to obtain the filtered PPG Signal 900. A first respiration cycle 902 and a second respiration cycle 904 may be obtained by measuring a low frequency component or fluctuation of the filtered PPG Signal 900. From this low frequency component, the biosensor 100 may obtain a respiratory rate of a user from the PPG Signal 900.

A heart rate may be determined from the spectral response. For example, the biosensor 100 may determine the time between diastolic points or between systolic points to determine a time period of a cardiac cycle 906. In another embodiment, to estimate the heart rate, the frequency spectrum of the PPG signal is obtained using a FFT algorithm over a predetermined period (hamming window). The pulse rate is estimated as the frequency that corresponds to the highest power in the estimated frequency spectrum. The frequency spectrum may be averaged over a time period, such as a 5-10 second window.

A pulse pressure 908 may be determined from the PPG signal 900. The pulse pressure 908 corresponds to an amplitude of the PPG signal 900 or a peak to peak value. The amplitude of the PPG signal 900 may be averaged over a time period to determine a pulse pressure 908.

Thus, a PPG signal may be used to determine heart rate, respiration rate and pulse rate. A light source in the UV range provides a PPG signal with a lower signal to noise ratio for determining heart rate and respiration rate in some tissue while a light source in the IR range provides a PPG signal with a lower signal to noise ratio in other types of tissue. The infrared range (IR) range may include wavelengths from 650 nm to 1350 nm.

Figure 10:
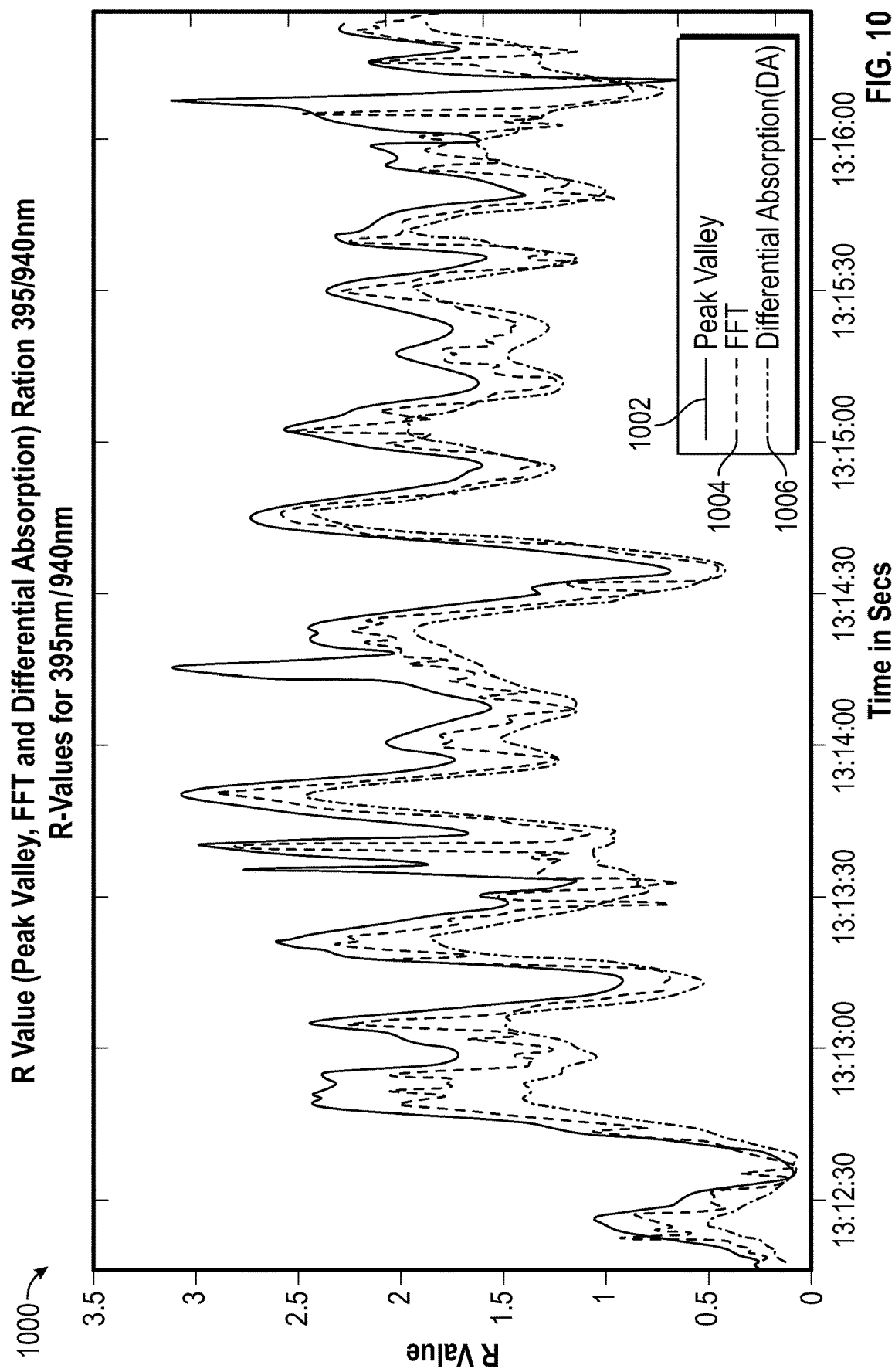
FIG. 10 illustrates a schematic drawing of an exemplary embodiment of results of R values determined using a plurality of methods.

FIG. 10 illustrates a schematic drawing of an exemplary embodiment of results of R values 1000 determined using a plurality of methods. The R values 1000 corresponding to the wavelengths of 395 nm/940 nm is determined using three methods. The R Peak Valley curve 1002 is determined using the Ratio $$R = \frac{L395}{L940}$$

as described hereinabove. The R FFT curve 1004 is obtained using FFT techniques to determine the $I_{CC}$ values and $I_{AC}$ component values of the spectral responses to determine the Ratio $$R = \frac{L395}{L940}.$$

The R differential absorption curve 1006 is determined using the shift in absorbance spectra as described in more detail in U.S. Utility application Ser. No. 15/275,388 entitled, "SYSTEM AND METHOD FOR HEALTH MONITORING USING A NON-INVASIVE, MULTI-BAND BIOSENSOR," filed Sep. 24, 2016, now U.S. Pat. No. 9,642,578 issued May 9, 2017, and hereby expressly incorporated by reference herein.

As seen in FIG. 10, the determination of the R values using the three methods provides similar results, especially when averaged over a period of time. A mean or average of the R values 1002, 1004 and 1006 may be calculated to obtain a final R value or one of the methods may be preferred depending on the positioning of the biosensor or underlying tissue characteristics.

Figure 11A:
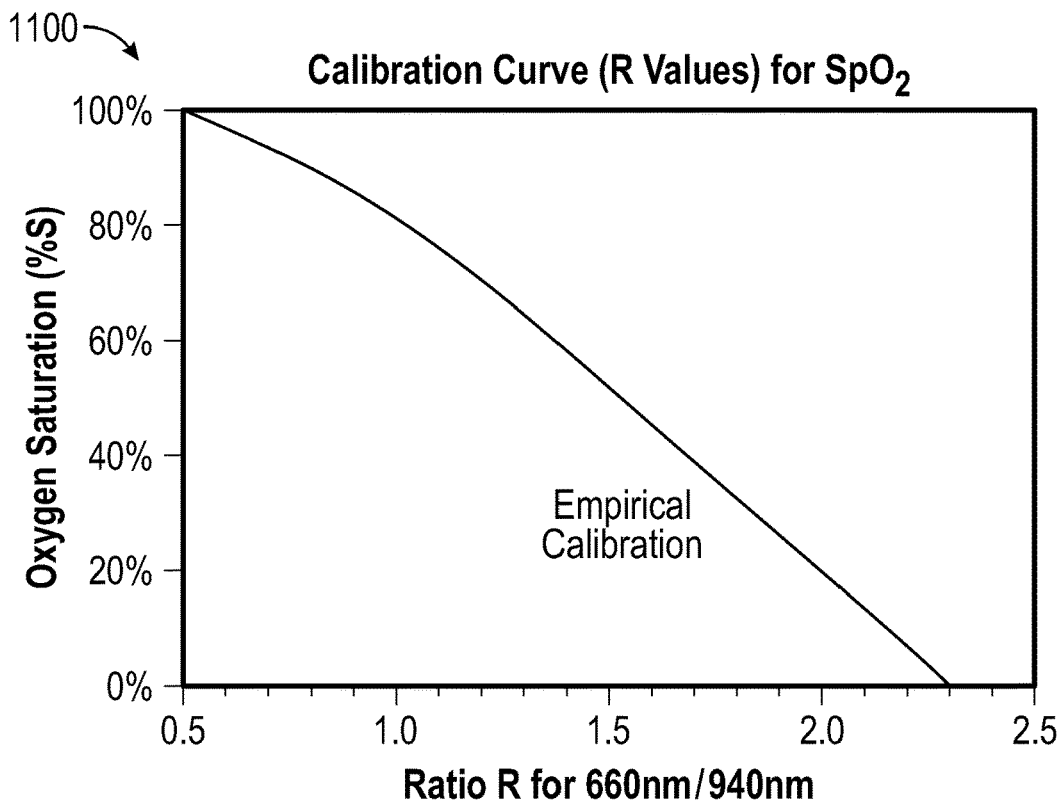
FIG. 11A illustrates a schematic drawing of an exemplary embodiment of an empirical calibration curve for correlating oxygen saturation levels ($SpO_2$) with R values.

FIG. 11A illustrates a schematic drawing of an exemplary embodiment of an empirical calibration curve 1100 for correlating oxygen saturation levels (SpO$_2$) with R values. The calibration curve 1100 may be included as part of the calibration database for the biosensor 100. For example, the R values may be obtained for $L_{660\ nm}/L_{940\ nm}$. In one embodiment, the biosensor 100 may use a light source in the 660 nm wavelength or in a range of +/−50 nm to determine SpO$_2$ levels, e.g. rather than a light source in the IR wavelength range. The 660 nm wavelength has been determined in unexpected results to have good results in measuring oxygenated hemoglobin, especially in skin tissue with fatty deposits, such as around the abdominal area.

Figure 11B:
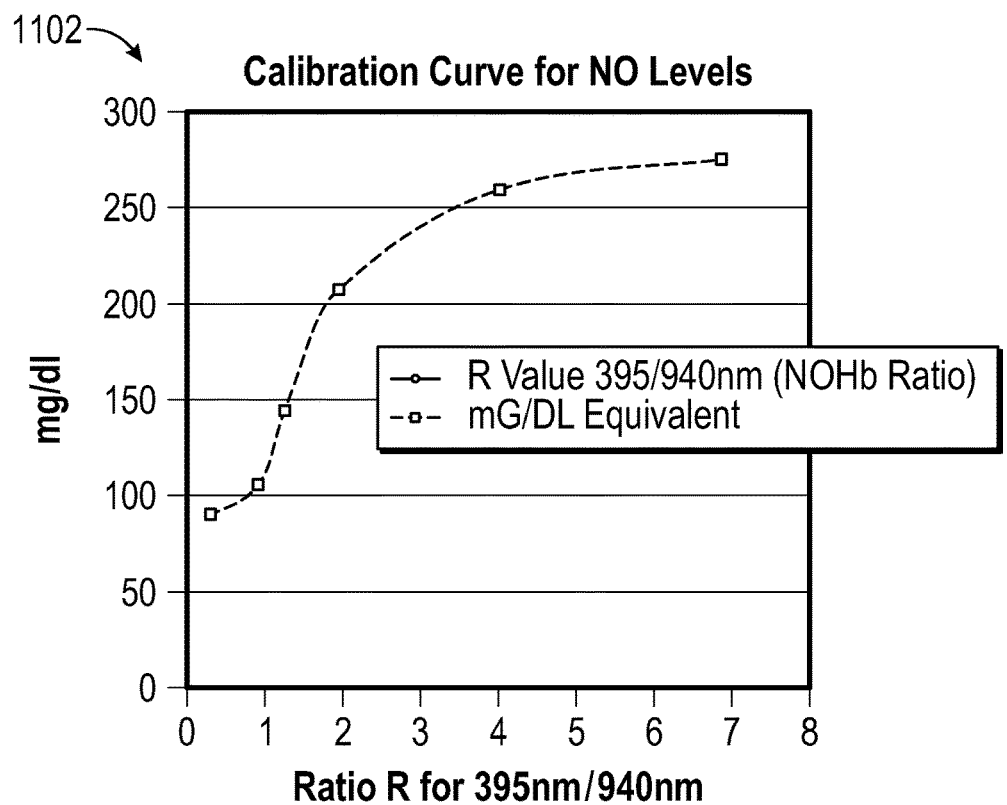
FIG. 11B illustrates a schematic drawing of an exemplary embodiment of an empirical calibration curve for correlating NO levels with R values.

FIG. 11B illustrates a schematic drawing of an exemplary embodiment of an empirical calibration curve 1102 for correlating NO levels (mg/dl) with R values. The calibration curve 1102 may be included as part of the calibration database for the biosensor 100. For example, the R values may be obtained in clinical trials from measurements of $L_{395\ nm}/L_{940\ nm}$ and the NO levels of a general sample population. The NO levels may be measured using one or more other techniques for verification to generate such a calibration curve 1102. This embodiment of the calibration curve 1102 is based on limited clinical data and is for example only. Additional or alternative calibration curves 1212 may also be derived from measurements of a general population of users at one or more different positions of the biosensor 100. For example, a first calibration curve may be obtained at a forehead, another for an abdominal area, another for a fingertip, another for a palm, etc.

From the clinical trials, the L values obtained at wavelengths around 390 nm (e.g. 380-410) are measuring nitric level (NO) levels in the arterial blood flow. The R value for L390/L940 nm may thus be used to obtain NO levels in the pulsating blood flow. From the clinical trials, it seems that the NO levels are reflected in the R values obtained from L390 nm/L940 nm and wavelengths around 390 nm such as L395 nm/L940 nm. The NO levels may thus be obtained from the R values and a calibration database that correlates the R value with known concentration levels of NO.

In other embodiments, rather than Lλ1=390 nm, the L value may be measured at wavelengths in a range from 410 nm to 380 nm, e.g., as seen in the graphs wherein Lλ1=395 nm is used to obtain a concentration level of NO. In addition, Lλ2 may be obtained at any wavelength at approximately 660 nm or above. Thus, R obtained at approximately Lλ1=380 nm-400 nm and Lλ2>660 nm may also be obtained to determine concentration levels of NO.

In an embodiment, the concentration level of NO may be correlated to a diabetic risk or to blood glucose levels using a calibration database. For example, the R value is averaged over a short period of time (e.g., around less than 2-3 minutes) and then correlated with a level of glucose.

Embodiment—Detection of a Risk of Sepsis or an Infection Based on NO Levels

In an embodiment, the biosensor 100 may detect a risk of sepsis using NO concentration levels. In this embodiment, an R value derived from $L_{395}$ and $L_{940}$ is used to determine a NO measurement though other parameters may be obtained, such as $R_{390/940}$ or $L_{390}$. In the clinical trials herein, the $R_{395/940}$ value for a person without a sepsis condition was in a range of 0.1-8. In addition, it was determined that the $R_{395/940}$ value of 30 or higher is indicative of a patient with a sepsis condition and that the $R_{395/940}$ value of 8-30 was indicative of a risk of sepsis in the patient. In general, the $R_{395/940}$ value of 2-3 times a baseline of the $R_{395/940}$ value was indicative of a risk of sepsis in the patient. These ranges are based on preliminary clinical data and may vary. In addition, a position of the biosensor, pre-existing conditions of a patient or other factor may alter the numerical values of the ranges of the $R_{395/940}$ values described herein.

The R values are determined by using a wavelength in the UV range with high absorption coefficient for NO, e.g. in a range of 380 nm-410 nm. These R values have a large dynamic range from 0.1 to 300 and above. The percentage variance of R values in these measurements is from 0% to over 3,000%. The R values obtained by the biosensor 100 are thus more sensitive and may provide an earlier detection of septic conditions than blood tests for serum lactate or measurements based on MetHb.

For example, an optical measurement of MetHb in blood vessels is in a range of 0.8-2. This range has a difference of 1.1 to 1.2 between a normal value and a value indicating a septic risk. So, these measurements based on MetHb have less than a 1% percentage variance. In addition, during a septic condition, MetHb may become saturated due to the large amount of NO in the blood vessels. So, an optical measurement of MetHb alone or other hemoglobin species alone is not able to measure these excess saturated NO levels. The R values determined by measuring NO level directly using a wavelength in the UV range are thus more sensitive, accurate, have a greater dynamic range and variance, and provide an earlier detection of septic conditions.

A baseline NO measurement in blood vessels of a healthy general population is obtained. For example, the biosensor 100 may obtain R values or other NO measurements using the biosensor 100. For example, the biosensor 100 may measure an L395 value or determine SpNO % based on an R value for a general population over a period of time, such as hours or days. These NO measurements are then averaged to determine a baseline NO measurement. The NO measurement in blood vessels is then obtained for a general population with a diagnosis of sepsis. For example, the biosensor 100 may obtain R values or other NO measurements (such as an L395 value or SpNO %) for patients diagnosed with sepsis using traditional blood tests, such as serum lactate blood tests. The biosensor 100 may monitor the patients throughout the diagnosis and treatment stages. The NO measurements are then averaged to determine a range of values that indicate a septic condition.

Predetermined thresholds may then be obtained from the NO measurements. For example, a threshold value indicative of a non-septic condition may be obtained. A threshold value for a septic condition may also be obtained. The biosensor 100 is then configured with the predetermined thresholds for the NO measurement.

The predetermined thresholds may be adjusted based on an individual patient's pre-existing conditions. For example, a patient with diabetes may have lower R values. A baseline NO value for a patient may also be determined based on monitoring of the patient during periods without infections. The predetermined thresholds stored in the bio sensor 100 may then be adjusted based on any individual monitoring and/or pre-existing conditions.

In addition, the predetermined thresholds may be determined and adjusted based on positioning of the biosensor 100. For example, different R values or other NO measurements may be obtained depending on the characteristics of the underlying tissue, such as tissue with high fatty deposits or with dense arterial blood flow. The thresholds and other configurations of the biosensor 100 may thus be adjusted depending on the underlying skin tissue, such as a forehead, chest, arm, leg, finger, abdomen, etc.

Embodiment—Detection of Other Conditions Based on NO Levels

In another embodiment, post-traumatic stress disorder (PTSD) may result in higher than normal NO levels. There are several reports that increased oxidative stress may be a factor in the evolution of some enduring neurological and psychiatric disorders and PTSD. Stress, a risk factor for developing PTSD, evokes a sustained increase in nitric oxide synthase (NOS) activity that can generate excessive amounts of nitric oxide. Oxidation of nitric oxide produces peroxynitrite that is very toxic to nerve cells, and elevated levels of peroxynitrite and its precursor nitric oxide have been observed in patients with PTSD. An article by Kedar N. Prasad and Stephen C. Bondy, entitled, "Common biochemical defects linkage between post-traumatic stress disorders, mild traumatic brain injury (TBI) and penetrating TBI," Brain Research, Volume 1599, Pages 103-114, Mar. 2, 2015, and incorporated by reference herein, describes the elevation of nitric oxide NO that may indicate PTSD. The biosensor 100 may thus operate in one or more modes to detect or provide a warning of abnormal NO levels indicative of PTSD.

In another embodiment, concussions, mild traumatic brain injury (TBI) and penetrating TBI, may also result in abnormal NO levels. The article by James H. Silver, entitled, "Inorganic Nitrite as a Potential Therapy or Biomarker for Concussion," J. Neurol Neurophysiol, Volume 7, Issue 2 (April 2016), and incorporated by reference herein, describes an abnormal pattern of nitric oxide NO levels after a concussion. For example, it has been observed that a rapid increase in nitric oxide occurs within minutes following head injury, followed by a decline to below baseline within hours. The biosensor 100 may monitor NO levels after a head trauma and detect this sudden increase and then reduction below baseline in NO levels. In use, a baseline level of NO may be determined for a user during normal conditions. After a potential head injury, the user is then monitored by the biosensor 100 for changes from this baseline level of NO. This process may be performed, e.g., for sideline evaluation of potentially concussed athletes. Thus, the biosensor 100 may operate in one or more modes to monitor NO levels and provide a warning of abnormal NO levels that may indicate a concussion or TBI.

In one or more modes of operation, the biosensor 100 may thus be configured to detect one or more of these other substances in addition to or alternatively from NO levels in blood flow.

Figure 12:
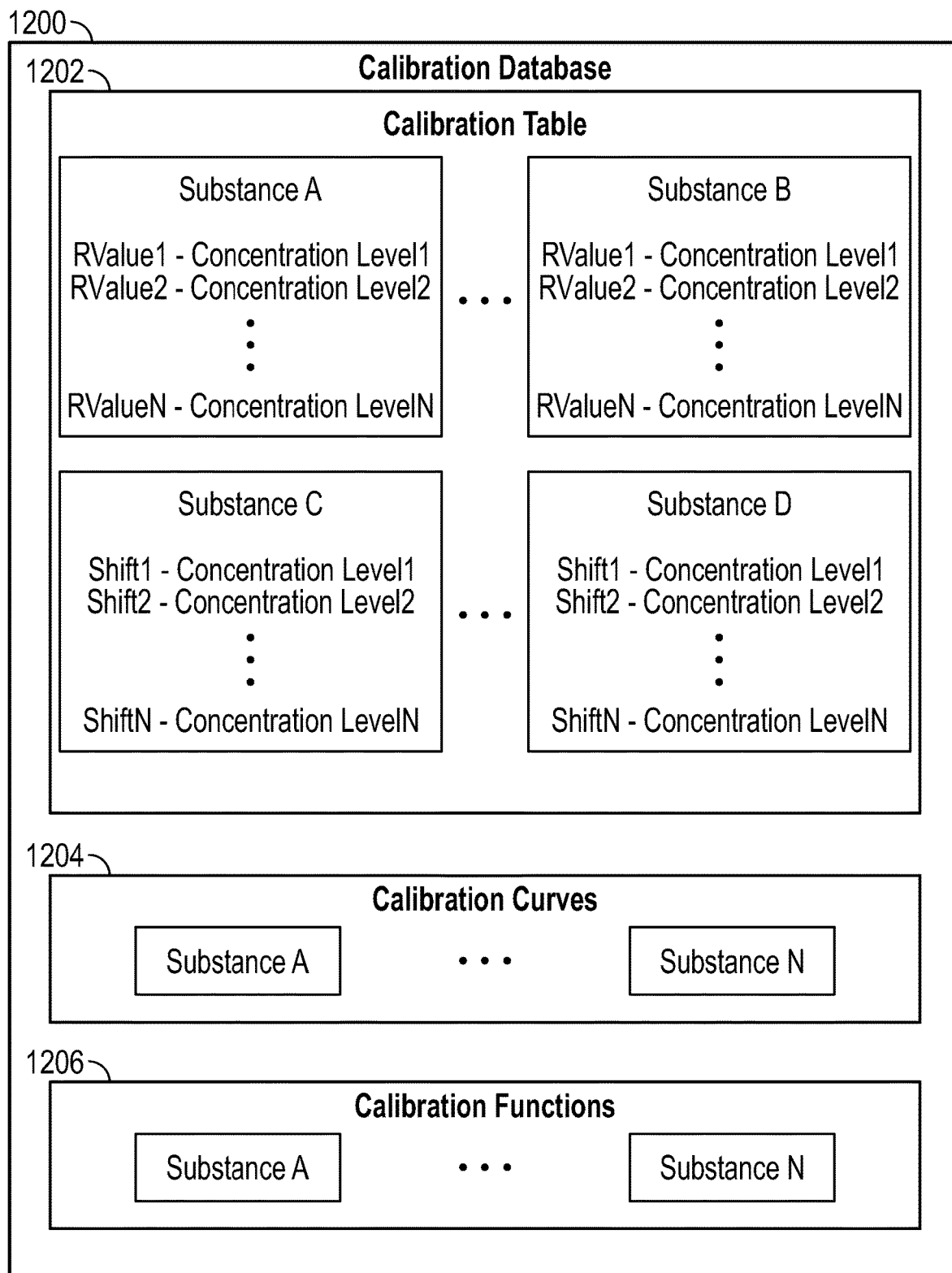
FIG. 12 illustrates a schematic block diagram of an embodiment of a calibration database.

FIG. 12 illustrates a schematic block diagram of an embodiment of a calibration database 1200. The calibration database 1200 includes one or more calibration tables 1202, calibration curves 1204 or calibration functions 1206 for correlating obtained values to concentration levels of one or more substances A-N. The concentration level of the substances may be expressed in the calibration tables 1202 as units of mmol/liter, as a saturation level percentage (SpNO %), as a relative level on a scale (e.g., 0-10), etc.

The calibration database 1200 may also include one or more calibration tables for one or more underlying skin tissue types. In one aspect, the calibration database 1200 may correlate an R value to a concentration level of a substance for a plurality of underlying skin tissue types.

In another aspect, a set of calibration tables 1202 may correlate an absorption spectra shift to a concentration level of one or more substances A-N. For example, a first table may correlate a degree of absorption spectra shift of oxygenated hemoglobin to NO concentration levels. The degree of shift may be for the peak of the absorbance spectra curve of oxygenated hemoglobin from around 421 nm. In another example, the set of table 1202 may correlate a degree of absorption spectra shift of deoxygenated hemoglobin to NO concentration levels. The degree of shift may be for the peak of the absorbance spectra curve of deoxygenated hemoglobin from around 430 nm.

The calibration database 1200 may also include a set of calibration curves 1204 for a plurality of substances A-N. The calibration curves may correlate L values or R values or degree of shifts of spectral data to concentration levels of the substances A-N.

The calibration database 1200 may also include calibration functions 1206. The calibration functions 1206 may be derived (e.g., using regressive functions) from the correlation data from the calibration curves 1204 or the calibration tables 1202. The calibration functions 1206 may correlate L values or R values or degree of shifts in spectral data to concentration levels of the substances A-N for one or more underlying skin tissue types.

Embodiment—Neural Network

One or more types of artificial neural networks (a.k.a. machine learning algorithms) may be implemented herein to determine health data from PPG signals. For example, neural networks may be used to obtain a concentration level of NO or glucose or other health data from input data derived from PPG signals. Neural network models can be viewed as simple mathematical models defining a function $f$ wherein $f:X \rightarrow Y$ or a distribution over X or both X and Y. Types of neural network engines or APIs currently available include, e.g. TensorFlow™, Keras™, Microsoft® CNTK™, Caffe™, Theano™ and Lasagne™.

Sometimes the various machine learning techniques are intimately associated with a particular learning rule. The function $f$ may be a definition of a class of functions (where members of the class are obtained by varying parameters, connection weights, thresholds, etc.). The neural network learns by adjusting its parameters, weights and thresholds iteratively to yield desired output. The training is performed using defined set of rules also known as the learning algorithm. Machine learning techniques include ridge linear regression, a multilayer perceptron neural network, support vector machines and random forests. For example, a gradient descent training algorithm is used in case of supervised training model. In case, the actual output is different from target output, the difference or error is determined. The gradient descent algorithm changes the weights of the network in such a manner to minimize this error. Other learning algorithms include back propagation, least mean square (LMS) algorithm, etc. A set of examples or a training set is used for learning by the neural network. The training set is used to identify the parameters [e.g., weights] of the network.

Figure 13:
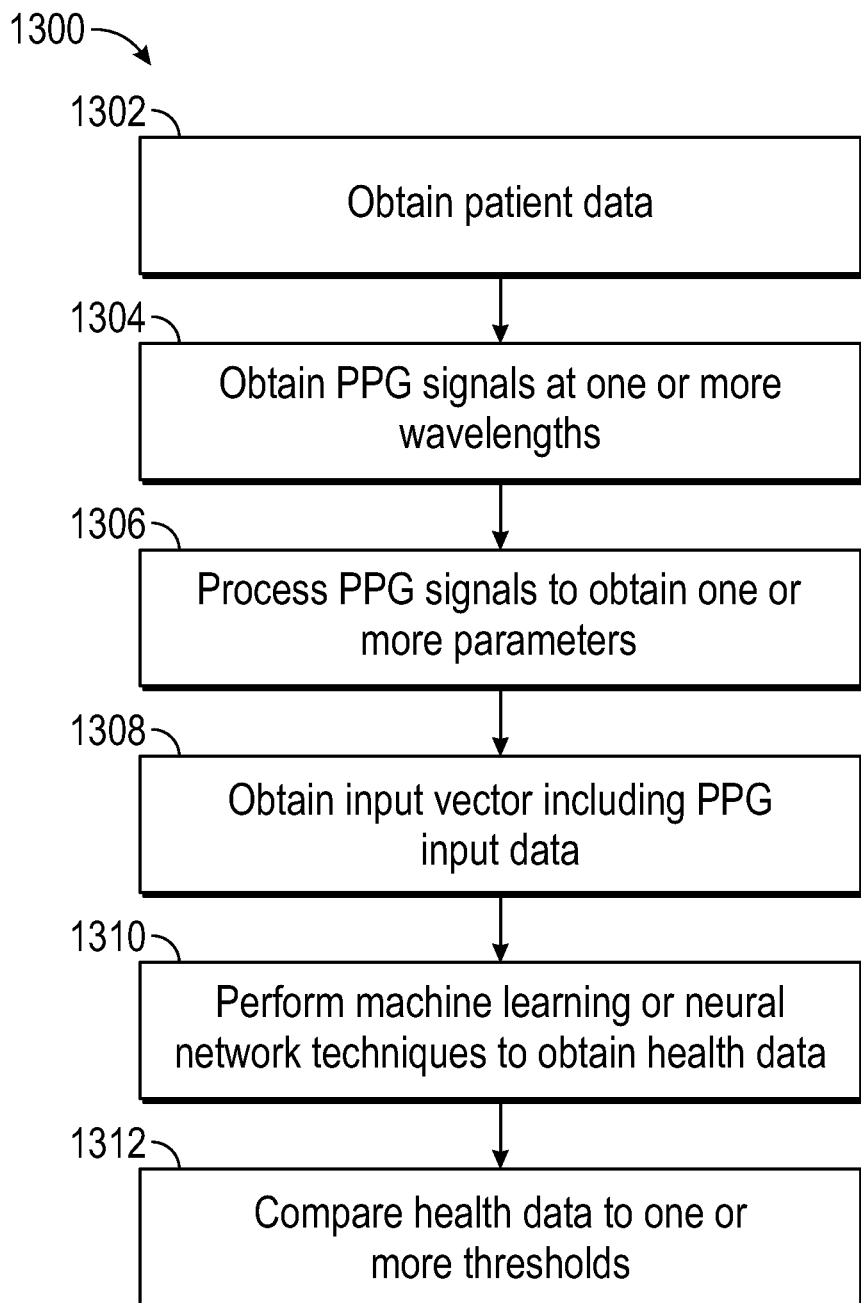
FIG. 13 illustrates a logical flow diagram of an embodiment of a method for using a machine learning neural network technique for detection of health data.

FIG. 13 illustrates a logical flow diagram of an embodiment of a method 1300 for using a machine learning neural network technique for detection of health data. In an embodiment, patient data is obtained at 1302. The patient data may include one or more of: age, weight, body mass index, temperature, blood pressure, pre-existing medical conditions, trauma events, mental conditions, injuries, demographic data, physical examinations, laboratory tests, diagnosis, treatment procedures, prescriptions, radiology examinations, historic pathology, medical history, surgeries, etc. PPG signals at one or more wavelengths are obtained at 1304.

Various parameters of the PPG signals may be determined or measured at 1306 These parameters include the diastolic and systolic points, transfer functions, timing differences between wavelengths, the L values, R values, pulse shape (measured by autoregression coefficients and moving averages), characteristic features of the shape of the PPG waveform, the average distance between pulses, variance, instant energy information, energy variance, etc. Other parameters may be extracted by representing the PPG signal as a stochastic auto-regressive moving average (ARMA). Parameters also may be extracted by modeling the energy of the PPG signal using the Teager-Kaiser operator, calculating the heart rate and cardiac synchrony of the PPG signal, and determining the zero crossings of the PPG signal. These and other parameters may be obtained using a PPG signal. The PPG input data may include the PPG signals, and/or one or more parameters derived from the PPG signals.

An input vector is obtained at 1308. The input vector includes the PPG input data, such as the PPG signals at one or more wavelengths and/or one or more parameters generated from the PPG signals at the one or more wavelengths. Since the PPG signal is of variable duration, a fixed dimension vector for a measurement of the PPG signal may be obtained. The input vector may also include patient data.

The input vector is processed by a processing device executing a neural network (aka machine learning algorithm). The processing device executes the machine learning algorithm or neural network techniques using the input vector to determine health data at 1310. The health data includes one or more of heart rate, period of vasodilation, level of vasodilation, respiration rate, blood pressure, oxygen saturation level, NO level, liver enzyme level, Glucose level, Blood alcohol level, blood type, sepsis risk factor, infection risk factor, cancer, virus detection, creatinine level or electrolyte level. The health data may also include blood viscosity, blood pressure, arterial stiffness, vascular health, cardiovascular risk, atherosclerosis, etc. The health data may be generated as an output fixed length vector.

The obtained health data may be compared to expected ranges or thresholds in a calibration table at 1312. Alarms or warnings may be issued based on the comparison.

Embodiment—Measurement of Vasodilation Using PPG Signals

Vasodilation is the widening of blood vessels. It results from relaxation of smooth muscle cells within the vessel walls, in particular in the large veins, large arteries, and smaller arterioles. The process is the opposite of vasoconstriction, which is the narrowing of blood vessels due to constriction of the smooth muscle cells within the vessels walls. The vascular endothelium is crucially involved in the fundamental regulation of blood flow matching demand and supply of tissue. After transient ischemia, arterial inflow increases. As a response to increased shear forces during reactive hyperemia, healthy arteries dilate via release of NO or other endothelium-derived vasoactive substances. This endothelium-dependent flow-mediated vasodilation (FMD) is impaired in atherosclerosis.

The capacity of blood vessels to respond to physical and chemical stimuli in the lumen confers the ability to self-regulate tone and to adjust blood flow and distribution in response to changes in the local environment. Many blood vessels respond to an increase in flow, or more precisely shear stress, by dilating. This phenomenon is designated flow-mediated vasodilation (FMD). A principal mediator of FMD is endothelium-derived NO—an example of an EDRF.

Although the precise mechanism by which vasodilation occurs during reactive hyperemia in FMD measurement has not been fully elucidated, nitric oxide (NO) has been proposed as a principal mediator of FMD. The NO, produced as a result of an increase of endothelial NO synthase activity induced by shear stress, diffuses into the tunica media, leading to relaxation of smooth muscle cells and subsequent vasodilation. The assessment of endothelial function by FMD, therefore, presupposes a normal structural condition. Impaired endothelium-independent vasodilation is thought to be associated with structural vascular alterations and alterations in smooth muscle cells, e.g. as a result of atherosclerosis.

As the presence of endothelial dysfunction is closely associated with cardiovascular risk and outcome, the measurement of FMD in the brachial artery has become a standard method for the assessment of endothelial function in patients and to evaluate therapeutic interventions targeting atherosclerosis. For example, in healthy humans, the relative increase in brachial artery diameter during vasodilation is typically in the 5% to 10% range.

The current measurement of FMD in the brachial artery requires using high-frequency ultrasound to visually inspect the brachial artery. For example, one process includes applying a stimulus to provoke the endothelium to release nitric oxide (NO) with subsequent vasodilation that is then imaged and quantitated as an index of vasomotor function. This process of high-resolution ultrasonography of the brachial artery to evaluate FMD has limitations. It must be performed in a clinical setting by a medical clinician using expensive ultrasonography equipment.

Thus, there is a need for an improved system and method for detection of vasodilation and conditions affected by vasodilation and conditions that affect vasodilation. The systems and methods used to describe detection of a level of vasodilation and periods of vasodilation may be used to determine vasoconstriction.

In various embodiments described herein, vasodilation or vasoconstriction and characteristics thereof may be measured using PPG signals obtained by the biosensor. The effects of vasodilation may be observed in PPG signals in one or more of a plurality of wavelengths across different spectrums, such as IR, visible and UV. For example, PPG signals across the spectrum may vary in shape, intensity level and timing due to vasodilation. In one example, the effect of vasodilation is observed from phase differences between PPG signals of different wavelengths, especially between wavelengths in different spectrums. Vasodilation also causes subtle skin movement which may be observed in PPG signals, especially in lower frequency components of PPG signals (e.g. frequencies that do not reflect the pulsatile blow flow). Using one or more characteristics of the PPG signals, a level of vasodilation may be obtained. The level of vasodilation may be measured as a percentage change in the size of vessels, such as percentage increase in a baseline diameter or planar area, or in a range such as 1-10, or in other manners.

In addition, an arterial stiffness or elasticity index may be obtained using the PPG signals. The PPG signals may predict vascular health, such as atherosclerosis. For example, a timing or period to change from a state of vasodilation to normal width may be obtained using phase differences between different wavelengths. The rate of change may indicate vascular stiffness and a prediction of vascular health.

In another embodiment, the level of vasodilation may be used to calibrate measurement of oxygen saturation SpO2 or other measurements of concentration of substances in blood flow. For example, measurements of oxygen saturation levels may be in error during periods of vasodilation. These measurements of oxygen saturation during vasodilation may be identified and flagged and/or the measurements may be calibrated in response to a level of vasodilation.

The biosensor described herein obtains PPG signals and measures a relative level of vasodilation of vessels and a period of vasodilation. For example, the PPG signal measures the pressure wave of blood flow through vessels. Vasodilation changes the propagation properties of blood flow through vessels, and thus the PPG signal changes. The changes in PPG signals due to the changing propagation properties is reflected in a transfer function generated from the PPG signals, e.g. time differences and wave shape differences between PPG signals. The transfer function may be measured to determine a level of vasodilation in real time.

Figure 14:
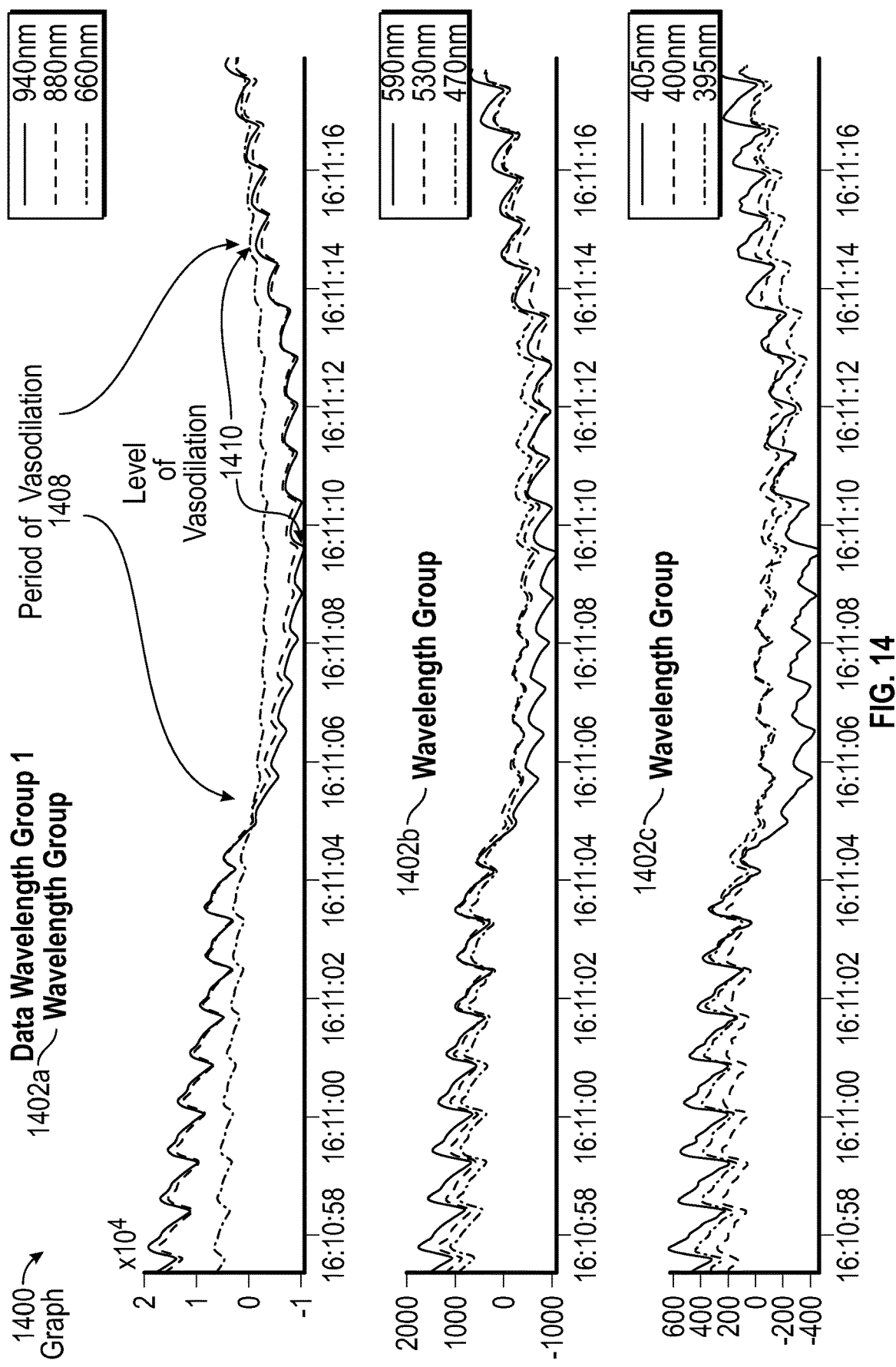
FIG. 14 illustrates a schematic diagram of a graph of PPG signals during a period of vasodilation in vessels.

FIG. 14 illustrates a schematic diagram of a graph 1400 of PPG signals during a period of vasodilation in vessels. At "rest", a body responds to caloric intake and vasodilation occurs normally as the body processes food, insulin is dispensed, and arteries expand due to Nitric Oxide (NO) causing the outer muscle of the arteries to expand temporarily. This vasodilation is reflected in the PPG signal, and highly visible in the signal to noise ratio.

The biosensor 100 obtained a PPG signal during vasodilation after caloric intake around a wavelength at 940 nm, a wavelength at 880 nm and a wavelength at 660 nm as shown in the PPG Signals for Wavelength Group 1402a. The biosensor 100 also obtained the spectral response for a wavelength at 590 nm, a wavelength at 530 nm and a wavelength at 470 nm as shown in the PPG Signals for Wavelength Group 1402b. The biosensor 100 further obtained the spectral response for a wavelength at 405 nm, a wavelength at 400 nm and a wavelength at 395 nm as shown in the PPG Signals for Wavelength Group 1402c.

As shown in the graphs, the PPG signals reflect a period of vasodilation 1408. The vasodilation 1304a-c is reflected in the PPG signals during a time period between approximately 16.11.04 secs through approximately 16.11.17 secs. In particular, a lower frequency component of the PPG signals changes during the period of vasodilation 1408. This lower frequency component of the PPG signals includes the lower frequencies not affected by the pulsating blood flow (pressure wave) due to the cardiac cycle.

During vasodilation, the arteries and other vessels widen changing the absorption properties of the vascular tissue. These changes in absorption properties are due, e.g., by the increase in blood in the vascular tissue and the compression of surrounding tissue due to the widening vessels. The PPG signals across wavelengths in the IR, visible and UV spectrums are affected by the changing absorption properties of the vascular tissue due to vasodilation.

The level of vasodilation 1410 may be obtained from the PPG signals. For example, the change in low frequency from the PPG signal may be correlated to a level of vasodilation. The level of vasodilation may be expressed as a percentage change of the diameter or planar area of the vessel or percentage increase in blood flow during the period of vasodilation. The level of vasodilation may alternatively be measured in a range such as 1-10, or in other manners.

The duration of the vasodilation may also be obtained from the PPG signals. The beginning of vasodilation and end of vasodilation may be identified from the PPG signals. For example, the vasodilation begins at approximately 16.11.04 secs and ends at approximately 16.11.17 secs in Graph 1400 and so indicates a period of vasodilation of 13 seconds.

Figure 15:
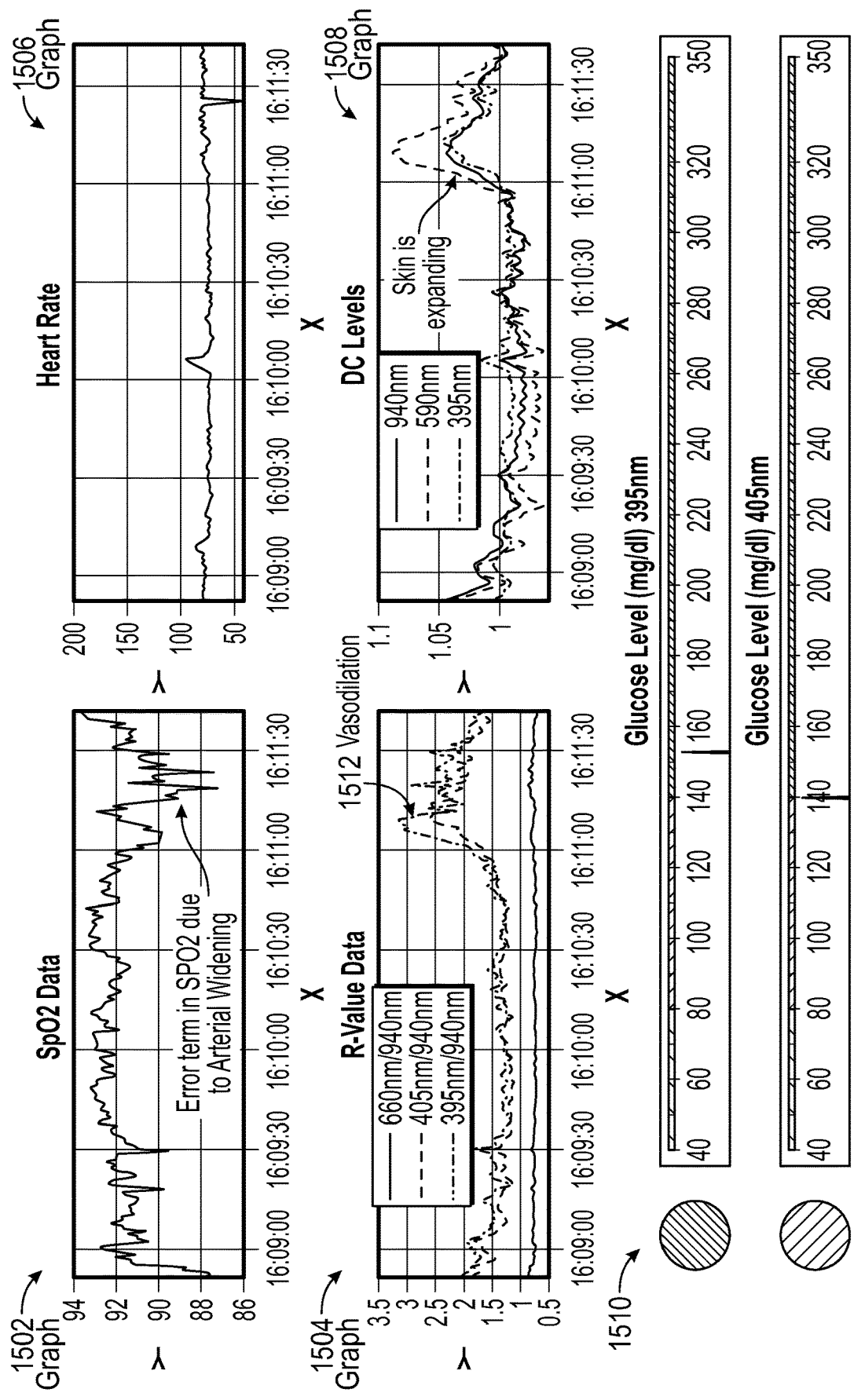
FIG. 15 illustrates a schematic diagram of a series of graphs illustrating the effects of vasodilation in PPG signals.

FIG. 15 illustrates a schematic diagram of a series of graphs illustrating the effects of vasodilation using the PPG signals shown in FIG. 14. The first graph 1502 illustrates R660/940 values that may be used to obtain a measurement of oxygen saturation SpO2. The vasodilation period 1512, seen at approximately 16.11.04 secs through approximately 16.11.17 secs, affects the R values and thus the SpO2 measurements. Other measurements based on R values or relative amplitudes of PPG signals are also affected by vasodilation. In an embodiment, an error value or calibration may be determined for measurements of oxygen saturation SpO2 during a period of vasodilation. The error value or calibration may depend on the level of vasodilation or change in R values due to the vasodilation.

The second graph 1504 illustrates R values at R660/940, R405/940 and R395/940. The vasodilation period 1512, seen at approximately 16.11.04 secs through approximately 16.11.17 secs, affects the R values, especially R values using PPG signals in the UV or near UV range. The R values may be affected during the vasodilation period since the ratio of the amplitude of different wavelengths is used to obtain the R values. This may cause errors in the measurement of blood component levels. The R values and/or measurements of blood component levels may be compensated due to the effect of vasodilation to correct errors during periods of vasodilation.

For example, during the expansion of vessels during a vasodilation period (e.g., due to NO or other EDRF), it may not be practical to measure the SpO2 amounts due to the error term present in the 940 & 660 nm PPG signals. This effect of vasodilation is likely being observed by current SpO2 meters. Errors in the measurement of SpO2 may be caused by undetected periods of vasodilation in current SpO2 meters. Vasodilation may also cause errors in determinations of other blood components using PPG signals. The measurement of the respiratory cycle in a PPG signal is also affected during vasodilation.

The duration of the vasodilation effect may depend on the individual, the amount of the food ingested and the arterial rigidity. For example, the vessels of diabetic subjects are likely to expand less and have much less change in amplitude of PPG signals during vasodilation due to inelasticity of the arteries due to arterial rigidity and endothelial dysfunction.

The graph 1506 illustrates the higher frequencies of the PPG signal at 660 nm that may be used to measure the heart rate remains relatively unaffected during the period of vasodilation.

The graph 1508 illustrates the lower frequencies of PPG signals at 940 nm, 590 nm and 395 nm (e.g., the frequencies not affected by pulsatile blood flow). The characteristics of the lower frequencies of the PPG signals change during the vasodilation period. The absorption properties of the vascular tissue vary due to changes in volume of blood. In addition, the widening of the vessels compresses the surrounding tissue. And the epidermis, the upper layer of the skin, may expand in response to the widening vessels during vasodilation. The PPG signals are thus affected by this change in absorption properties of the tissue, as seen in graph 1508.

The graph 1508 also illustrates that the PPG signals in different spectrums exhibit a time or phase delay. For example, the PPG signal at 940 nm in the IR range, the PPG signal at 590 nm in the visible range, and the PPG signal at 395 nm in the UV range have timing differences. This time delay is due in part to the different penetration depths of the wavelengths. Preferably, to determine this time delay, PPG signals in an infrared range (IR) range from 650 nm to 1350 nm and PPG signals outside the IR range are compared to determine the time or phase delay.

The graph 1510 illustrates an elevated glucose level during the vasodilation period of about 140-152 mg/dl. At "rest", a body responds to caloric intake and vasodilation occurs normally as the body processes food, insulin is dispensed, and arteries expand due to Nitric Oxide (NO) causing the outer muscle of the arteries to expand temporarily. This caloric intake also elevates the glucose level temporarily. As shown in the graphs, the SPO2 measurement is affected during the vasodilation period.

Vasodilation or vasoconstriction may also change the color or hue of the skin tissue due to expansion or contraction of the vessels. This increase or decrease of blood flow may change the hue of the skin. By monitoring the hue of the skin, the biosensor 100 may detect vasodilation or other changes in blood circulation in the tissue. For example, a PPG signal in a visible light range such as at a yellow (590 nm-560 nm) or Red (564 nm-580 nm) or Blue (490 nm-450 nm) wavelength may be used to detect a change in hue of the skin.

Furthermore, the PPG signals in different spectrums exhibit phase differences or timing differences that correspond to the expansion and constriction of the arteries during vasodilation or vasoconstriction. The phase differences are due in part to the different penetration depths of the wavelengths. At a same input power, light at higher wavelengths (IR light) penetrates vascular tissue deeper than light at lower wavelengths (UV light). The optical properties of the tissue are affected by many factors, including but not limited to, skin-tone, tissue hydration, and tissue chemistry. In a sensor configuration where the light from the light source is backscattered to a sensor on the same surface, the optical signal at the sensor includes a sum of all light backscattered that makes it to the focal surface after interacting with the tissue. With the optical power being the same across all wavelengths, some of the light backscattered from the IR light penetrates deeper into the tissue than the UV light does. This means that the different wavelengths of light probe different depths of tissue.

When the heart beats, the arteries swell as fluid is pushed out of the heart. The leading edge of the swelling or pressure wave moves like a "bulge" through the arterial system. This system can be thought of as an elastically dampened hydraulic system. The pressure wave or bulge in the pulsatile blood flow moves from the lower tissue to the upper tissue. Thus, the deeper penetrating wavelengths (such as IR light) detect a pressure wave first followed by the lesser penetrating wavelengths (such as visible then UV light). The time delay in the "bulge" or pressure wave moving from the lower tissue into the upper tissue thus creates a time delay in a pressure waveform seen in the PPG signals at different wavelengths. For example, as seen in FIG. 15, a waveform in the UV range has a time delay compared to a waveform in the IR range and a waveform in the visible range (390 nm to 700 nm). This time delay in the different wavelengths is thus due to the depth of penetration into the skin of each wavelength.

Vasodilation changes the propagation of the pressure wave starting in the deeper, larger arteries and then moving to the shallower, smaller ones. In an embodiment described herein, this change in propagation of the pressure wave can be measured in the change in transfer function from a wavelength that penetrates the tissue deeply (e.g. in the IR range) to a wavelength that penetrates tissue much less deeply (e.g. in the visible or UV range). This means that by measuring the change in shape and time delay of PPG signals of two or more wavelengths with different penetration depths (e.g., wherein at least one is in the near-IR window and one is not), information about vasodilation may be determined. Also, because the transfer function between the two depths of penetration is affected by blood pressure, blood viscosity, tissue absorption, and, in general, cardiovascular health, these other parameters can be characterized as well. Features or parameters of the PPG signal that can be examined include, but are not limited to, the time delay between the systolic points and diastolic points in different wavelengths and the difference in dicrotic notch suppression between wavelengths.

Figure 16:
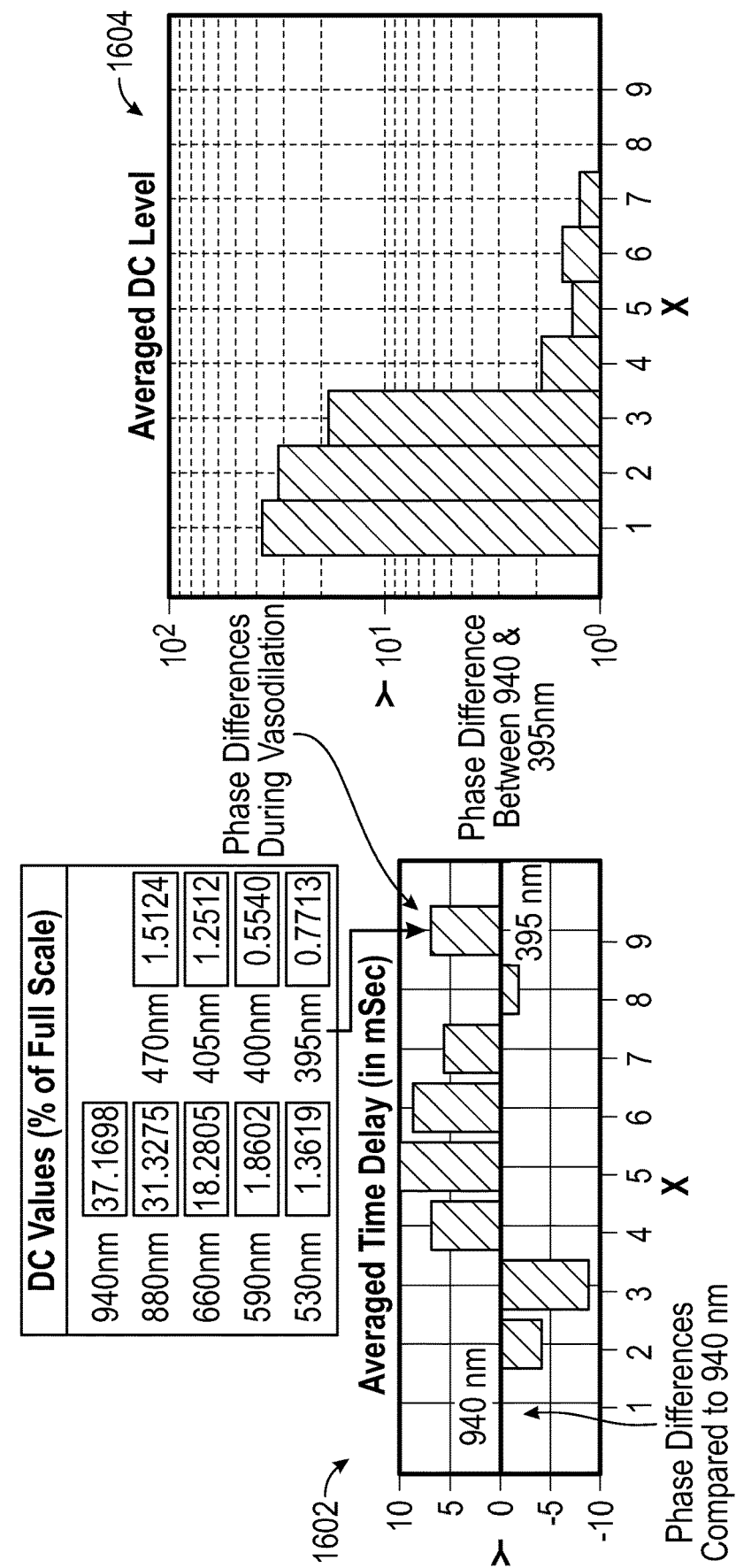
FIG. 16 illustrates a schematic diagram illustrating phase differences and average low frequency levels during vasodilation of PPG signals of various wavelengths.

FIG. 16 illustrates a schematic diagram 1600 illustrating phase differences and average low frequency levels during vasodilation using the PPG signals of various wavelengths from FIG. 14. The Graph 1602 illustrates the average phase difference between a PPG signal at 940 nm and PPG signals of various wavelengths during the period of vasodilation. The first time difference is 0 between 940 and itself. The last shown time difference is between 395 nm and 940 nm. The phase difference or the timing difference between PPG signals in graph 1602 illustrates a negative to positive timing which corresponds to the constrictions and expansion of the arteries during vasodilation. The phase delay between the PPG signals at different wavelengths is thus seen during a period of vasodilation.

The second graph 1604 illustrates the average "DC values" in PPG signals of various wavelengths during the period of vasodilation. The "DC values" include DC components and/or low frequency components not generally affected by the pulsatile blood flow. The graph 1604 illustrates that the average DC values $I_{DC}$ are above a baseline normal during the period of vasodilation. The average DC values increase due to vasodilation, tissue characteristics of contracting or expanding muscles and is proportional to the force applied to the muscle. So, the DC value (low frequencies not generally affected by the pulsatile blood flow) can be used to determine a force applied during the movement.

Detection of Vascular Health

The endothelium lines the walls of vessels and helps to regulate vascular function. In the vasculature, insulin is released in response to ingestion or hunger. The insulin activates two distinct signaling path-ways in the endothelium that result in secretion of nitric oxide (NO) and endothelin (ET-1), respectively.

Figure 17B:
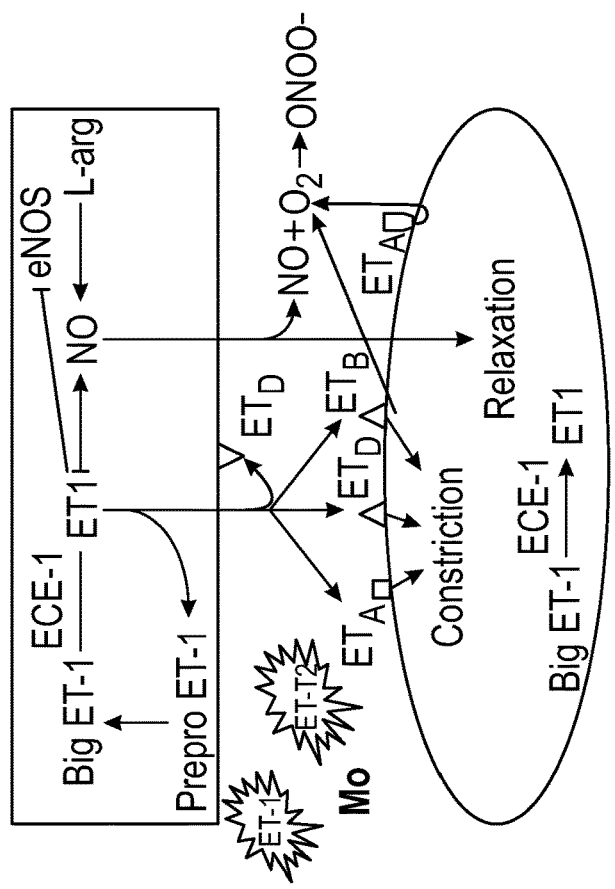
FIG. 17B illustrates a schematic block diagram of an arterial wall with vascular dysfunction.
Figure 17A:
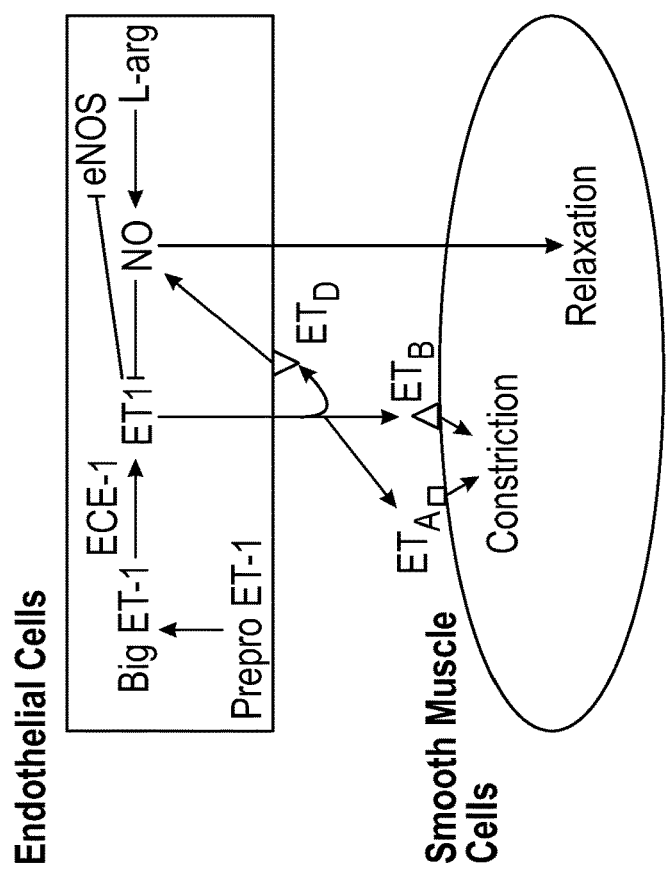
FIG. 17A illustrates a schematic block diagram of an arterial wall under healthy conditions.

FIG. 17A illustrates a schematic block diagram of an arterial wall under healthy conditions 1702. Smooth muscle cells respond to NO as a vasodilator and endothelin (ET-1) as a vasoconstrictor. ET-1 incites constriction in the smooth muscle cells by binding to $ET_A$ and $ET_B$ receptors. In the vasculature, the $ET_A$ receptor is mainly located on vascular smooth muscle cells and mediates vasoconstriction. The $ET_B$ receptor is primarily located on endothelial cells but may also be present on vascular smooth muscle cells. Stimulation of the endothelial $ET_B$ receptor results in release of NO and prostacyclin which causes vasodilatation, whereas stimulation of the vascular smooth muscle cell $ET_B$ receptor results in vasoconstriction. Thus, the net effect produced by ET-1 is determined on the receptor localization and the balance between $ET_A$ and $ET_B$ receptors.

Endothelial cells also mediate rapid responses to neural signals for blood vessel dilation, by releasing NO to make smooth muscles relax in the vessel wall. Production of NO counteracts or mediates the constricting effects of ET-1 in response to insulin in vasculatures. Insulin stimulates NO production in endothelial cells by subsequently activating the intracellular enzymes 1-phosphatidylinositol 3-kinase (PI3-ki-nase) and Akt, which activates endothelial NO synthase. NO, stimulated by higher insulin doses, is thought to be the underlying agent in insulin-mediated, endothelium-dependent vasodilation. In healthy arteries, smaller levels of ET-1 are produced in comparison to NO levels, and so the bioavailability of NO is preserved.

FIG. 17B is a schematic block diagram of an arterial wall with vascular dysfunction. In vascular dysfunction, there is an increased expression of ET-1 in smooth muscle cells and macrophages. There is also an increased expression of $ET_B$ receptors on smooth muscle cells mediating vasoconstriction. In addition, ET-1 may decrease endothelial NO synthase (eNOS) expression, thereby reducing NO production. Both the $ET_A$ and the $ET_B$ receptors on smooth muscle cells may mediate formation of superoxide ($O_2$) in endothelial dysfunction. Superoxide will decrease the biological activity of NO by forming peroxynitrate (ONOO—). This increases the effect of ET-1 and decreases the effect of NO on smooth muscle cells. Clinical evidence in obesity and diabetes suggest Endothelial dysfunction as a failure to vasodilate adequately after application of an endothelium-dependent vasodilator but also excess vasoconstrictor tone. Thus, ET-1 contributes to endothelial dysfunction both directly, through its vasoconstrictor effects, and indirectly, through inhibitory effects on NO production.

Collectively, the balance of these effects in endothelial dysfunction is shifted towards more vasoconstriction, inflammation and oxidative stress. This pathogenic role of the altered expression and biological actions of ET-1 in vascular dysfunction may lead to the development of cardiovascular disease, atherosclerosis and hypertension. For example, dysfunction of the vascular endothelium is an early finding in the development of cardiovascular disease and is closely related to clinical events in patients with atherosclerosis and hypertension.

Determination of ET-1 and NO Balance

As discussed above, in the vascular system, insulin stimulates both ET-1 and NO activity. An imbalance between the efficacy of these substances may be involved in the pathophysiology of heart disease, hypertension and atherosclerosis. Thus, a device and method to determine the balance of these substances in vivo would be important in determining insulin-resistance and vascular health.

Figure 18:
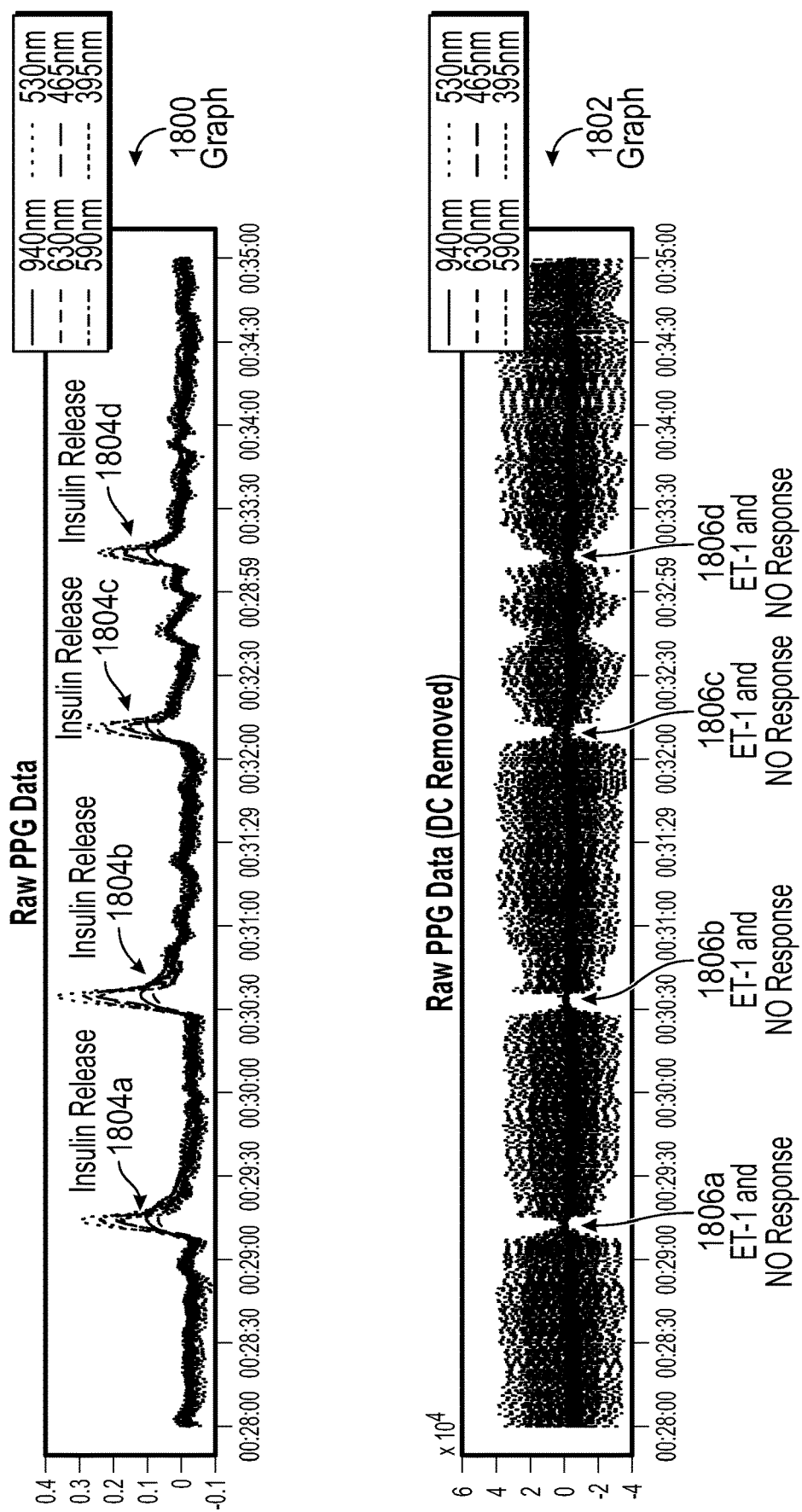
FIG. 18 illustrates a schematic diagram of PPG signals obtained during periods of insulin release in vessels.

FIG. 18 illustrates a schematic diagram of PPG signals obtained during periods of insulin release events in vessels. At "rest", a body responds to caloric intake by releasing insulin into the blood stream. This insulin release stimulates ET-1 and NO activity.

In the example of Graph 1800, the biosensor 100 obtained PPG signals over a seven minute period between 28 mins and 35 mins around a plurality of wavelengths at 940 nm, 630 nm, 590 nm, 530 nm, 465 nm and 395 nm. The PPG signals reflect "pulses" in response to discrete release of insulin in the bloodstream. The PPG signals reflect the insulin release events at a first pulse 1804a around 29.15 mins, a second pulse 1804b around 30.35 mins, a third pulse 1804c around 32.10 mins, and a fourth pulse 1804d around 33 mins. Vascular strain occurs during release of localized insulin (insulin release events) as part of the glucose regulation processes. This vascular strain impairs the PPG signals temporarily during the interaction of the ET-1 and NO agents released during the insulin release events.

Graph 1802 illustrates the PPG signals due to pulsatile blood flow $I_{AC}$. The $I_{DC}$ signal has been filtered from the PPG signals in this example. The $I_{AC}$ signal reflects the ET-1 and NO response in the vessels due to the insulin release events at a first pulse around 29.15 mins, a second pulse around 30.35 mins, a third pulse around 32.10 mins, and a fourth pulse around 33 mins. The smooth muscle cells of arterial walls tighten during chemical reactions of each insulin pulse. This temporary stiffing of the arterial structure causes a dampening effect on the PPG signals during the insulin release event. The 630 nm & 940 nm optical wavelengths are probing at deeper arterial/venous tissue structures wherein the smooth muscle walls are thicker and exhibit a higher stiffness factor under chemical induced strain such as an insulin release. The blood flow of the outer tissues (microvacuoles) include less smooth muscle tissue thickness and therefore respond with a more pronounced PPG signal pulse at 395 nm, 465 nm, 530 nm and 590 nm. Thus, the PPG pulses at these wavelengths are less pronounced.

Due to the higher level of insulin release, the ET-1 and NO response at the first pulse 1806a and the second pulse 1806b have a greater constricting effect on the vessels. The vasoconstriction decreases in the third and fourth pulses due to the decrease in insulin release at ET-1 and NO responses 1806c and 1806d. In addition, the NO levels may also have accumulated to further mediate the effects of ET-1. Thus, the vasoconstriction is lessened in response to the later insulin release events 1804c and 1804d.

The vasoconstriction in response to insulin release is thus affected by the balance of ET-1 and NO as well as vascular disease such as atherosclerosis. By measuring the relative vasoconstriction or change in arterial diameter in response to insulin release, vascular health may be assessed using the biosensor 100.

Figure 19:
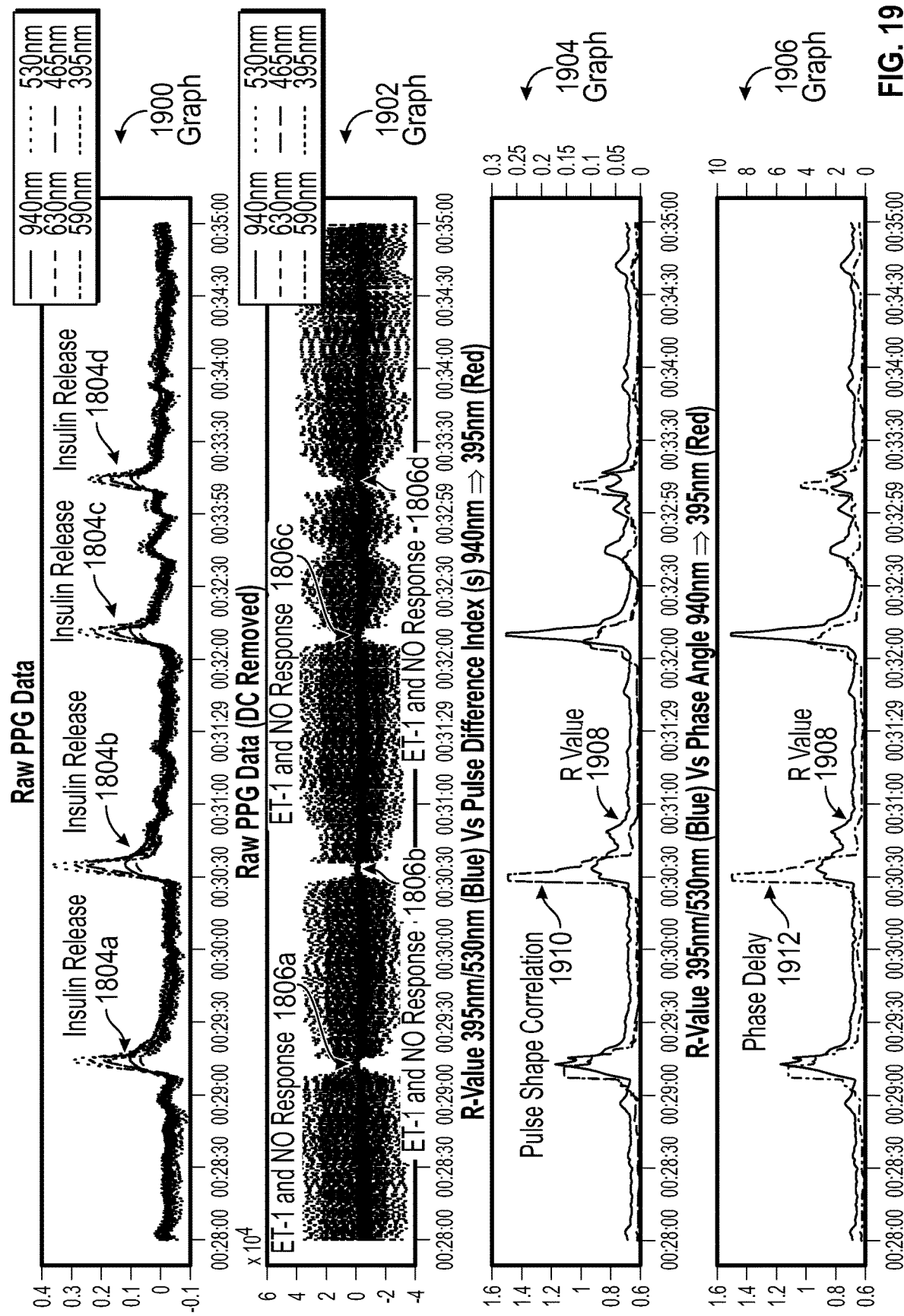
FIG. 19 illustrates a schematic diagram of graphs comparing phase offset and pulse shape waveform in a plurality of PPG signals during insulin release in vivo.

FIG. 19 illustrates a schematic diagram of graphs comparing phase delay and pulse shape correlation in a plurality of PPG signals during insulin release in vivo. As shown in Graph 1800, in the example of Graph 1900, the biosensor 100 obtained PPG signals over a seven minute period between 28 mins and 35 mins around a plurality of wavelengths at 940 nm, 630 nm, 590 nm, 530 nm, 465 nm and 395 nm. The PPG signals reflect "pulses" in response to discrete release of insulin in the bloodstream. Graph 1902 illustrates the PPG signals due to pulsatile blood flow $I_{AC}$ with low frequency signals $I_{DC}$ filtered therefrom.

In Graph 1904 and 1906, the R value 1908 of 395 nm/530 nm is illustrated. In addition, a correlation is computed between the PPG waveform at 940 nm and the PPG waveform at 395 nm to obtain a Pulse Shape Correlation 1910 and a Phase Delay 1912. The PPG signals are processed using, e.g., a cross correlation function or a Hilbert transformation or another algorithm that determines similarities in pulse shape and temporal relationship between PPG signals. For example, the time delay between the two signals can also be calculated at each time instant from the phase shift of their wavelet transforms.

The Pulse Shape Correlation 1910 and Phase Delay 1912 include effects of outer and inner tissue layers of vessels on the PPG signal. When the muscle cells constrict during vasoconstriction, the optical properties are altered. In addition, the change in NO level affects the PPG signal around 395 nm.

In healthy persons, arterial walls are more flexible and thus have a greater relative change in diameter in response to insulin. The Pulse Shape Correlation 1910 and Phase Delay 1912 signals reflect a greater change in signal levels in response to insulin. The R value pulses are correspondingly more pronounced. The phase timing is inversely proportional to the arterial diameters.

In patients having endothelium dysfunction, the arteries exhibit stiffness with a decreased relative change in diameter. Endothelium dysfunction may be found in patients with diseases such as atherosclerosis, hypertension and diabetes. The Pulse Shape Correlation 1910 and Phase Delay 1912 respond with a decreased relative amplitude change during an insulin release event. The Pulse Shape Correlation 1910 and Phase Delay 1912 may thus be used to determine vascular health.

In an embodiment, the phase delay 1912, pulse shape correlation 1910 and R value 1908 may be used to determine whether ET-1 or NO is more dominant in response to insulin. For example, the average or mean range of one or more of these measurements in a healthy population is measured. Then, an individual measurement is compared to the average or mean range of one or more of phase delay 1912, pulse shape correlation 1910 and R value 1908. The comparison may be used to obtain whether an imbalance is present between the effects of ET-1 and NO. An imbalance in the effects of the two substances has an increased vasoconstrictor effect on vessels due to an increase in ET-1 activity.

In addition, this change in propagation of the pressure wave can be measured in the change in transfer function from a wavelength that penetrates the tissue deeply (e.g. in the IR range) to a wavelength that penetrates tissue much less deeply (e.g. in the visible or UV range). This means that by measuring the change in pulse shape and phase delay of the PPG signals at two or more wavelengths with different penetration depths (e.g., wherein at least one is in the near-IR window and one is not), information about vasoconstriction may be determined.

Biosensor Detection of Vascular Health

Figure 20:
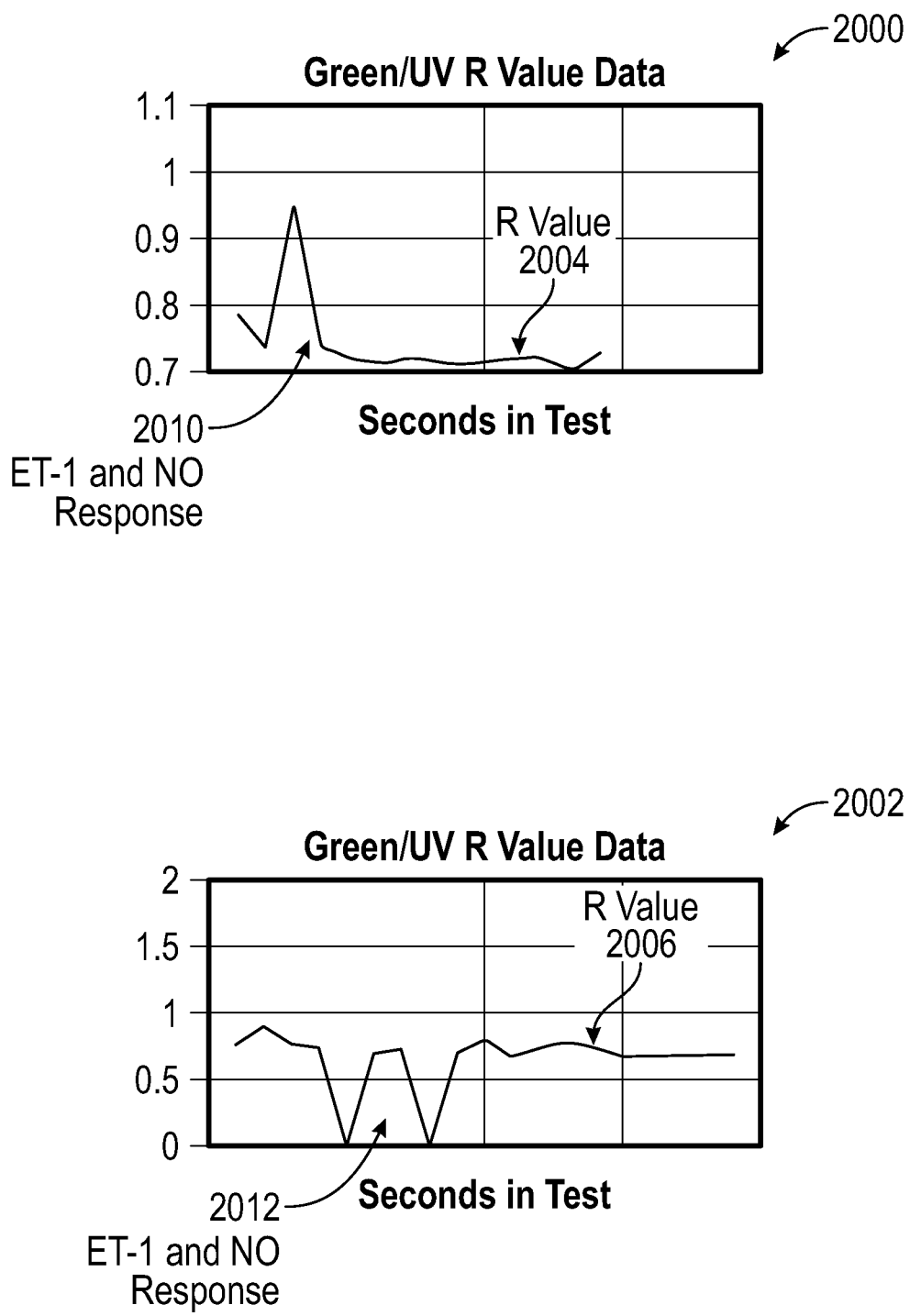
FIG. 20 illustrates a schematic block diagram of an insulin response of a young healthy male and a middle-aged male.

FIG. 20 illustrates a schematic block diagram of an insulin response of a young healthy male and a middle-aged male. The Graph 2000 illustrates an R value 2004 of 395 nm/530 nm during an insulin response in a middle-aged male patient obtained using the biosensor 100. In the ET-1 and NO response 2010, the R values 2004 shows a subdued response due to an increased arterial stiffness and/or ET-1 prominence. The ET-1/NO response 2010 is more typical of vasoconstriction.

The Graph 2002 illustrates an R value 2006 of 395 nm/530 nm during an insulin response in a young male patient. In the ET-1 and NO response 2012, the R values 2006 have a relatively greater range due to a healthy vascular system. The ET-1/NO response 2012 is more typical of vasodilation. Thus, by comparing the R value data of healthy persons in a general population with an individual's measurement, the presence of an increased arterial stiffness and/or ET-1 prominence may be determined.

Figure 21:
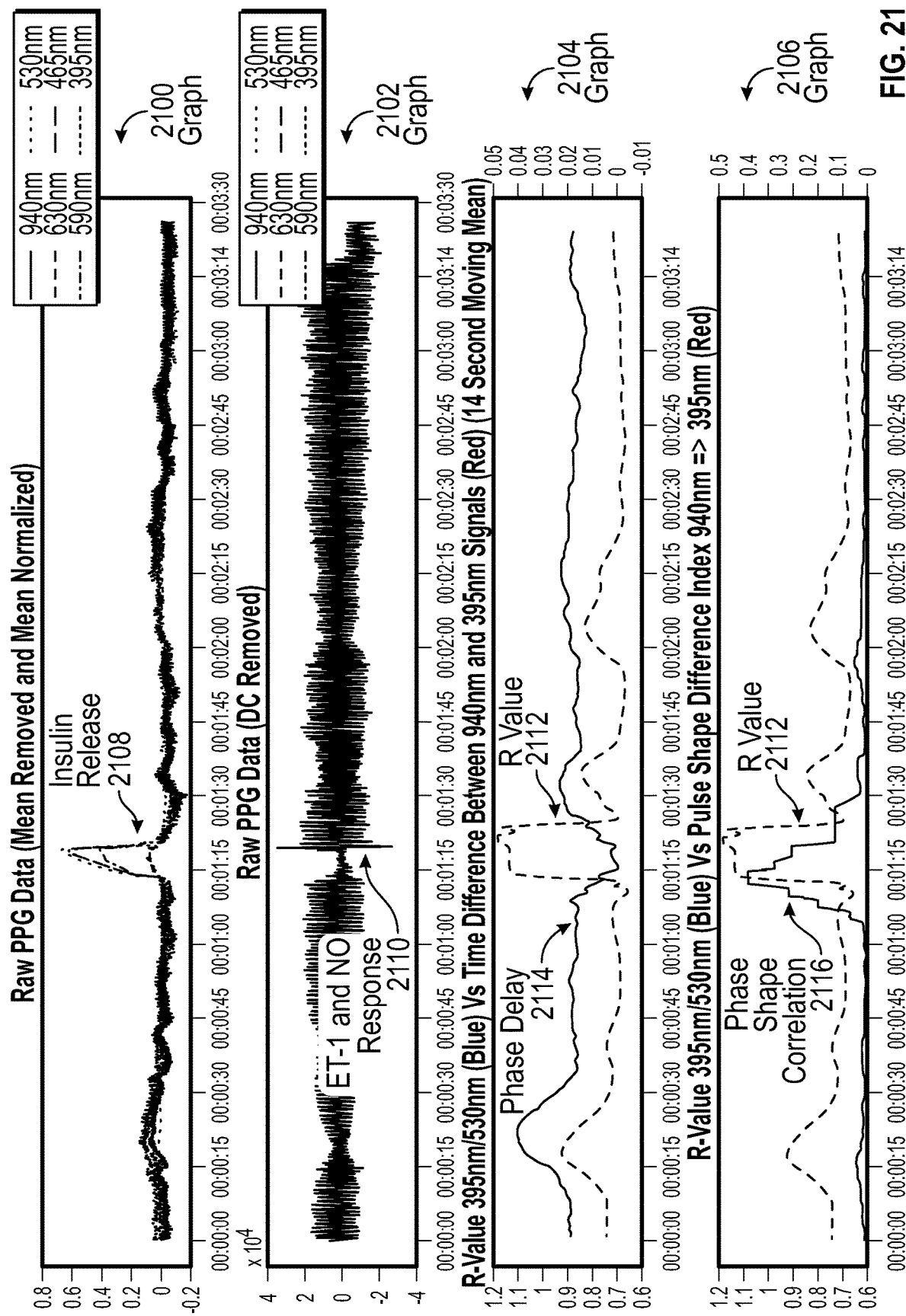
FIG. 21 illustrates a schematic diagram of graphs comparing phase offset and pulse shape waveform in a plurality of PPG signals during insulin release in an adolescent male.

FIG. 21 illustrates a schematic diagram of graphs comparing phase offset and pulse shape waveform in a plurality of PPG signals during insulin release in an adolescent male. In the example of Graph 2100, the biosensor 100 obtained PPG signals over an approximately three minute period around a plurality of wavelengths at 940 nm, 630 nm, 590 nm, 530 nm, 465 nm and 395 nm. The PPG signals reflect a discrete insulin release event 2108 in the bloodstream. The insulin release 2108 includes a marked PPG pulse in a first wavelength having a high absorption coefficient for NO, (e.g. 395 nm) wherein the amplitude of the pulse is at least greater than twice expected from a heart rate pulse.

Graph 2102 illustrates the PPG signals due to pulsatile blood flow $I_{AC}$. The $I_{AC}$ signal reflects an ET-1 and NO response 2110. The $I_{AC}$ signal has at least a 50% decrease in amplitude during the insulin release event 2108. One reason for the decrease in amplitude includes the constriction of the smooth muscle cells in vessels that affects the absorption properties of the tissue.

In Graph 2104 and 2106, the R value 2112 of 395 nm/530 nm is illustrated. In addition, a correlation between the PPG waveform at 940 nm and the PPG waveform at 395 nm is also illustrated. The correlation includes a Phase Delay 2114 and a Pulse Shape Correlation 2116. The PPG signals are processed using a cross correlation function or a Hilbert transformation or another algorithm that determines similarities in pulse shape and temporal relationship between the PPG signals. For example, the time delay between the two signals can also be calculated at each time instant from the phase shift of their wavelet transforms.

The Phase Delay 2114 and a Pulse Shape Correlation 2116 includes effects of outer and inner tissue layers of vessels on the PPG signal, e.g. muscle cells during vasoconstriction. The Phase Delay 2114 and a Pulse Shape Correlation 2116 may be mapped to a vessel diameter or level of vasoconstriction/vasodilation.

Figure 22:
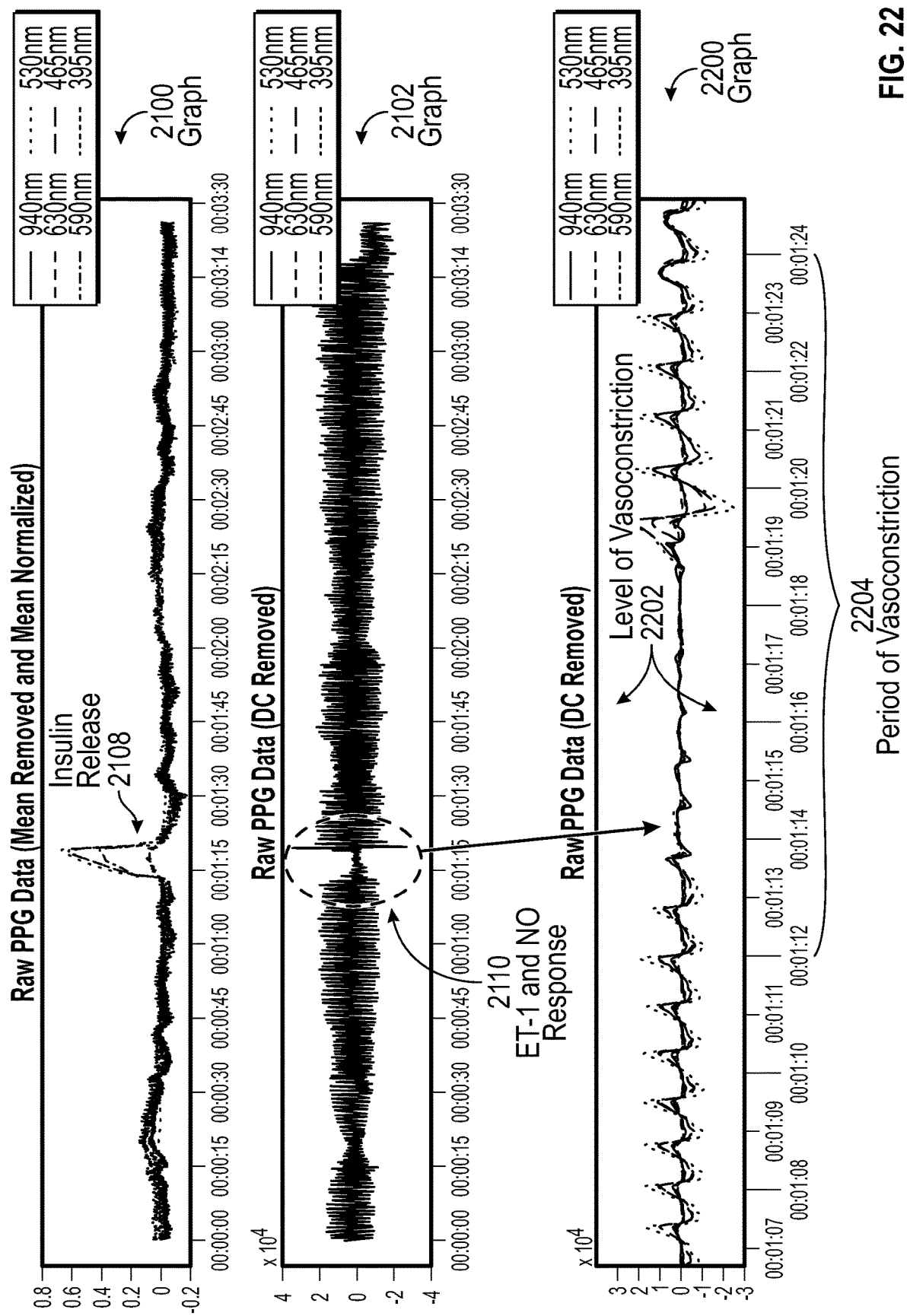
FIG. 22 illustrates a schematic diagram of an insulin response in the adolescent male in greater detail.

FIG. 22 illustrates a schematic diagram of an insulin response in the adolescent male in greater detail. Graph 2200 illustrates the PPG signals due to pulsatile blood flow $I_{AC}$ during the period of insulin release 2108. The ET-1 and NO response 2110 includes a decrease in amplitude of the $I_{AC}$ signal due to vasoconstriction. The constricting shallow muscle cells affect the optical properties of the PPG signals during this interval.

The period of vasoconstriction 2204 may be determined based on the amplitude changes of the PPG signals. At the beginning of the period of vasoconstriction 2204, the amplitudes of the $I_{AC}$ signal begin to decrease and then to slowly increase until the amplitudes of the $I_{AC}$ signal return to average at the end of the period of vasoconstriction 2204. The period of vasoconstriction 2304 is approximately between 21 sec and 31 sec. in this example.

A level of vasoconstriction 2202 may be determined, e.g., from an average peak to peak amplitude of the PPG signals prior to or after the period of vasoconstriction and the lowest peak to peak amplitude of the PPG signals during the period of vasoconstriction. The level of vasoconstriction may be measured in other manners, such as average peak value to lowest peak value during the period of vasoconstriction.

Figure 23:
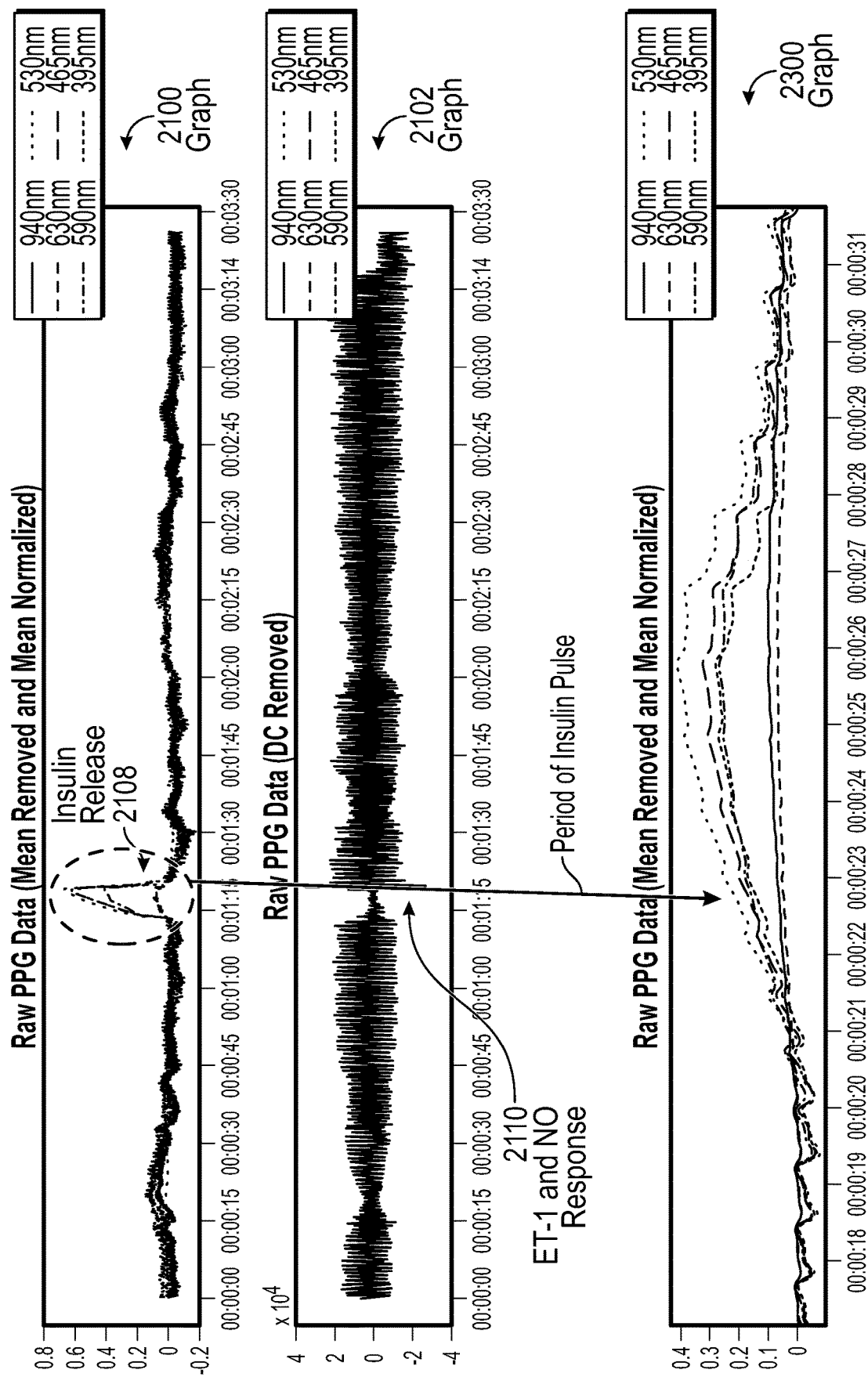
FIG. 23 illustrates a schematic diagram of an insulin response in the adolescent male in greater detail.

FIG. 23 illustrates a schematic diagram of an insulin response in the adolescent. Graph 2300 illustrates the PPG signals during the insulin release event 2108 in greater detail. The Graph 2300 illustrates that the insulin release generates a constricting response in the vessels over an approximately 10 second interval during the period of vasoconstriction 2204.

Figure 24:
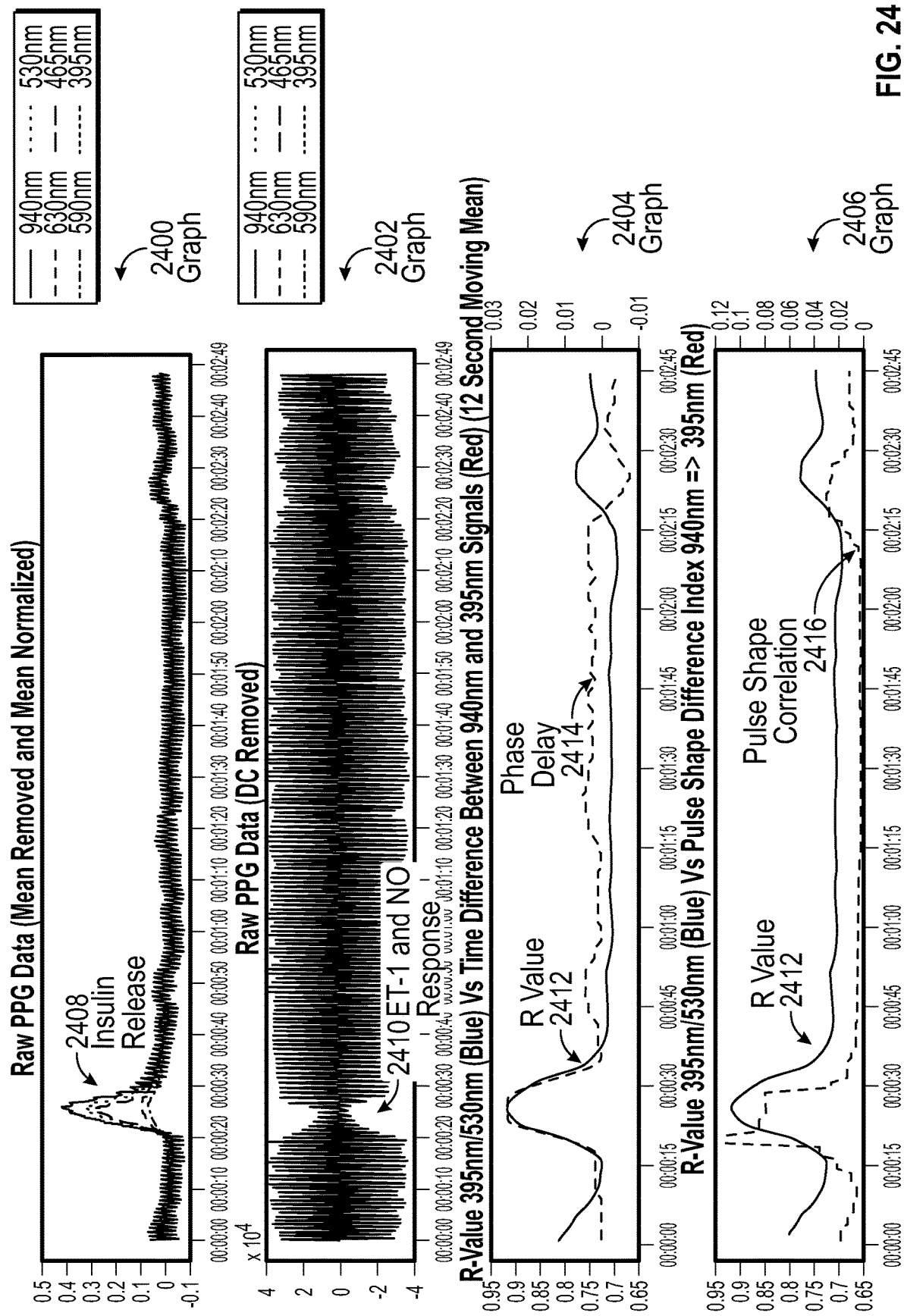
FIG. 24 illustrates a schematic diagram of graphs comparing phase offset and pulse shape waveform in a plurality of PPG signals during insulin release in a middle-aged male.

FIG. 24 illustrates a schematic diagram of graphs comparing phase offset and pulse shape waveform in a plurality of PPG signals during an insulin release event in a middle-aged male. In the example of Graph 2400, the biosensor 100 obtained PPG signals over a 2:49 minute period around a plurality of wavelengths at 940 nm, 630 nm, 590 nm, 530 nm, 465 nm and 395 nm. The PPG signals reflect a pulse in response to a discrete insulin release 2408 in the bloodstream. The insulin release 2108 includes a marked PPG pulse in a first wavelength having a high absorption coefficient for NO, wherein the amplitude of the pulse is at least greater than twice expected from a heart rate pulse.

Graph 2402 illustrates the PPG signals due to pulsatile blood flow $I_{AC}$. The $I_{AC}$ signal reflects an ET-1 and NO response 2410 in the vessels due to the insulin release 2408. The $I_{AC}$ signal has at least a 50% decrease in amplitude during the insulin release event 2408.

In Graph 2404 and 2406, the R value 2412 of 395 nm/530 nm is illustrated. In addition, a correlation between the PPG waveform at 940 nm and the PPG waveform at 395 nm is illustrated as Phase Delay 2414 and Pulse Shape Correlation 2416. The PPG signals are processed using a cross correlation function or a Hilbert transformation or another algorithm that determine similarities in pulse shape and temporal relationship between PPG signals. For example, the time delay between the two signals can also be calculated at each time instant from the phase shift of their wavelet transforms.

The Phase Delay 2414 and a Pulse Shape Correlation 2416 includes effects of outer and inner tissue layers of vessels on the PPG signal, e.g. muscle cells during vasoconstriction. The Phase Delay 2414 and a Pulse Shape Correlation 2416 may be mapped to a vessel diameter or level of vasoconstriction/vasodilation.

Figure 25:
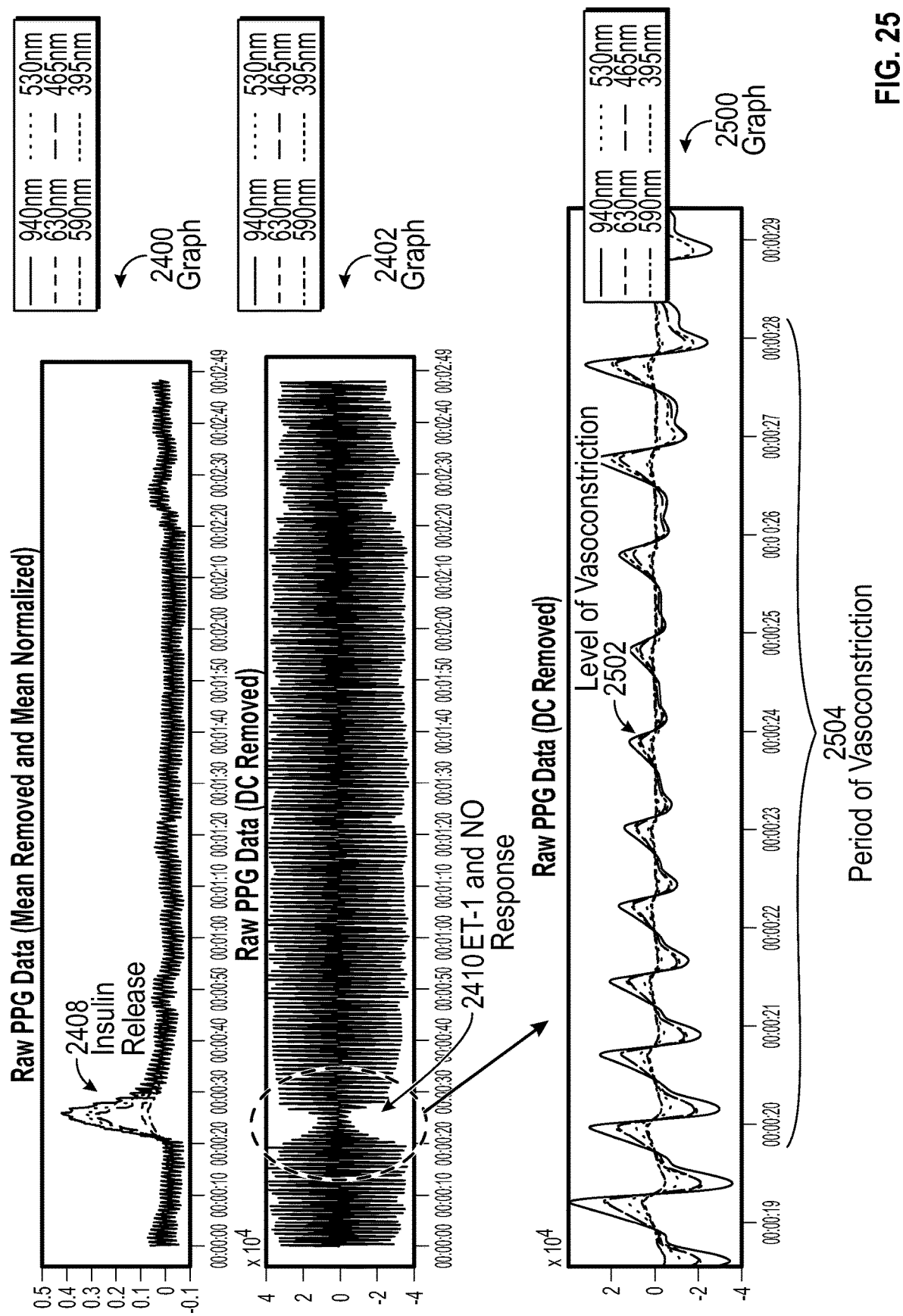
FIG. 25 illustrates a schematic diagram of an insulin response in a middle-aged male in greater detail.

FIG. 25 illustrates a schematic diagram of an insulin response in a middle aged male in greater detail. From FIG. 24, graph 2402 illustrates the PPG signals due to pulsatile blood flow $I_{AC}$ during the period of insulin release 2408. The Graph 2500 illustrates that the ET-1 and NO response 2410 from graph 2402 in greater detail. Graph 2500 reflects the decrease in amplitude of the $I_{AC}$ signal due to vasoconstriction. When smooth muscles cells tighten causing vasoconstriction, the $I_{AC}$ signal amplitude decreases in magnitude. The constricting shallow muscle cells affect the optical properties of the PPG signals during this interval.

The period of vasoconstriction in this example is from about 20 seconds to at least 28 seconds, e.g. the period of vasoconstriction 2504. A level of vasoconstriction 2502 may be determined, e.g., from an average peak to peak amplitude of the PPG signals prior to or after the period of vasoconstriction and the lowest peak to peak amplitude of the PPG signals during the period of vasoconstriction. The level of vasoconstriction may be measured in other manners, such as average peak value to lowest peak value during the period of vasoconstriction.

Figure 26:
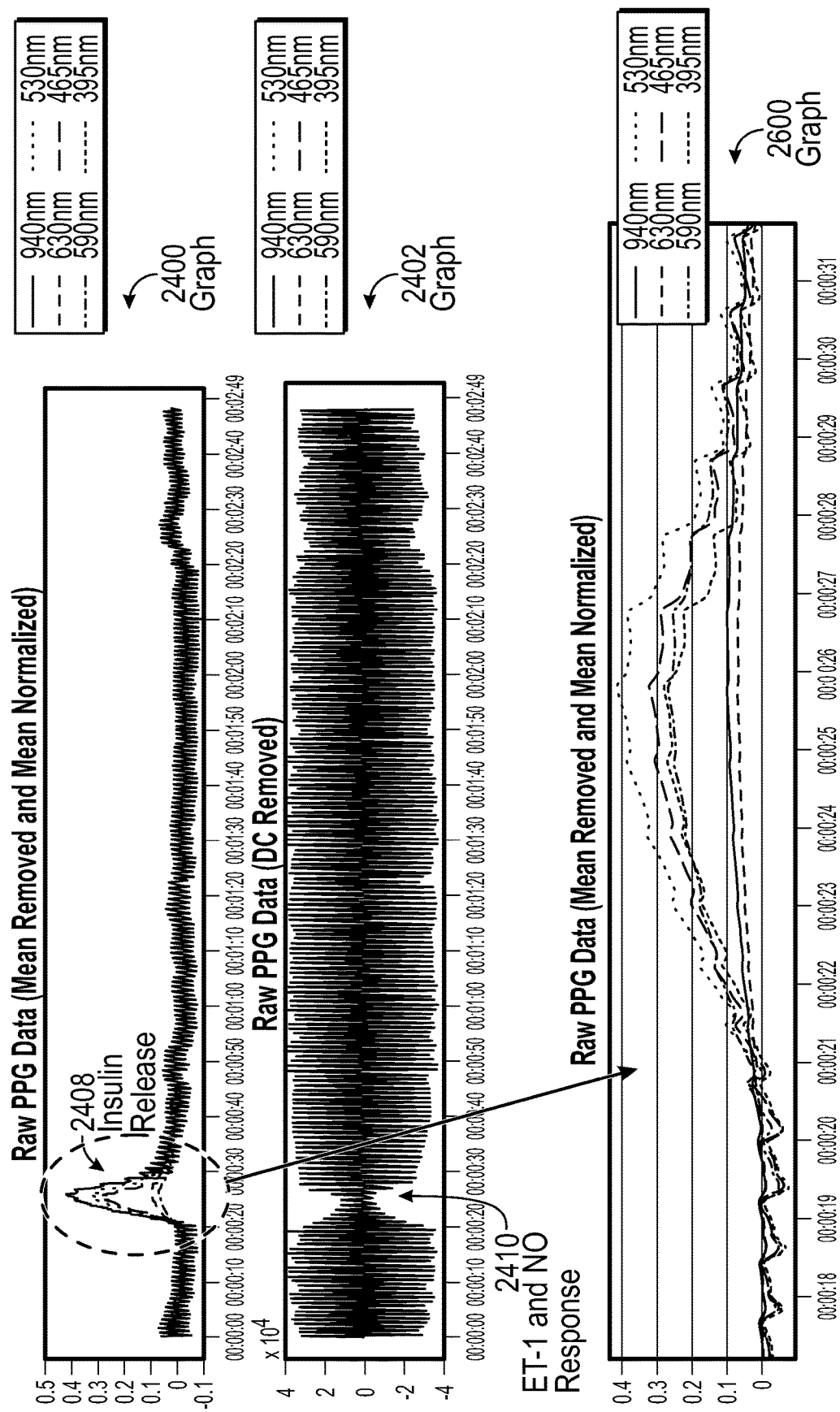
FIG. 26 illustrates a schematic diagram of an insulin response in a middle-aged male in greater detail.

FIG. 26 illustrates a schematic diagram of an insulin response in a middle aged male in greater detail. Graph 2600 illustrates the PPG signals during the period of insulin release 2408. The Graph 2600 illustrates that the insulin release generates a constricting response in the vessels during the period of vasoconstriction. The constricting shallow muscle cells affect the optical properties of the PPG signals during this interval.

Comparing the PPG signals detected during the insulin release between the adolescent male and the middle aged male, the PPG signals indicate that the vasoconstriction is relatively less in the middle aged male. The decrease in vasoconstriction is expected due to age related arterial stiffness and arteriosclerosis. This age-related difference in vasoconstriction can be due to decreased elastic production from fibrinogen, associated with ageing, or hypertension or pathological conditions such as atherosclerosis. The smooth muscle cells of the adolescent male may also be stronger, and the elastic lamina that surrounds the lumen of the artery may be more resilient and flexible at that age. This demonstrates that a level of vasoconstriction may be determined from the PPG signals and compared to healthy values (such as in the adolescent male) to determine vascular health.

Figure 27:
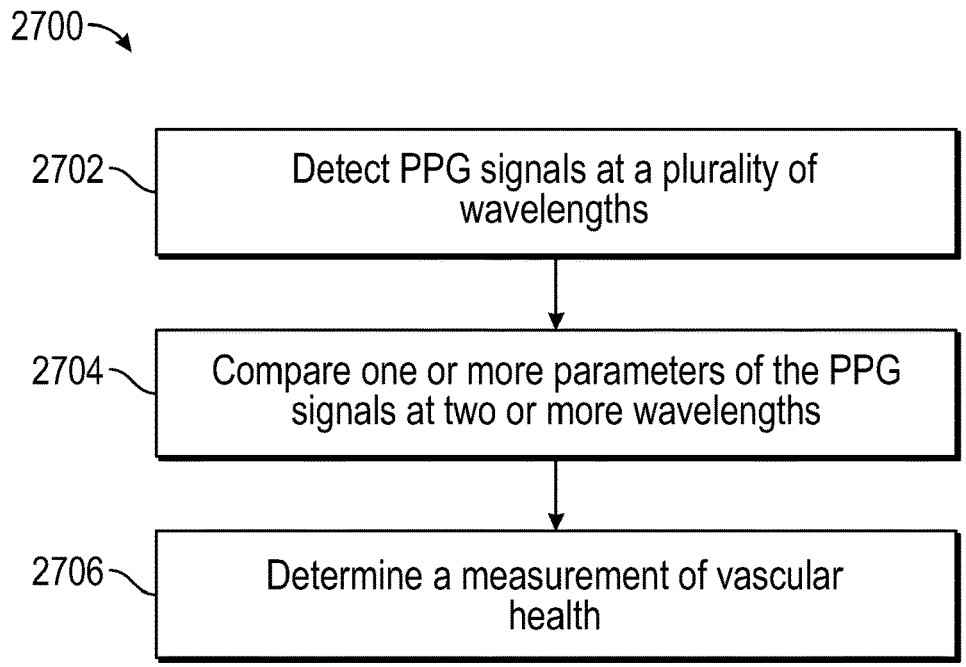
FIG. 27 illustrates a schematic flow diagram of an embodiment of a method for determining vascular health using the biosensor.

FIG. 27 illustrates a schematic flow diagram of an embodiment of a method 2700 for determining vascular health using the biosensor 100. The biosensor 100 detects PPG signals at a plurality of wavelengths reflected from skin tissue at 2702. Preferably, the first wavelength has a high absorption coefficient for NO and is approximately 395 nm or in a range from 380 to 410 and a lower depth of penetration into the tissue. The second wavelength has a lower absorption coefficient for NO and is approximately in a range from 510 nm to 550 nm or is in an IR range such as 940 nm and has a greater depth of penetration into the tissue.

The PPG signals are measured over a period of time that preferably includes one or more insulin release events, such as after ingestion, wherein insulin is released into the blood stream. The insulin release is reflected by a marked PPG pulse in the first wavelength having a high absorption coefficient for NO. The pulse has a 5-10 second duration, wherein the amplitude of the pulse is at least greater than twice expected from a heart rate pulse. The pulses due to insulin release also have a much lower frequency than a heart rate. The insulin release event may thus be identified in the PPG signals using one or more of these characteristics.

One or more parameters derived using the PPG signals during the insulin release event is determined and compared at 2704. For example, a cross correlation function may determine a phase offset between the PPG signals and/or pulse shape correlations during the insulin release event. The PPG signals may also be processed using other cross correlation functions or a Hilbert transformation or another algorithm that determine similarities in pulse shape and temporal relationship between PPG signals.

A measurement of vascular health is obtained using the one or more parameters at 2706. For example, a measurement of vasoconstriction or vasodilation may be obtained, such as a vessel diameter or percentage of change in diameter. The relative efficacy of ET-1 and NO may be estimated based on the measurement of diameter change and level of insulin release. A level of arterial stiffness may be determined using the measurement of the diameter change and level of insulin release and comparing to such measurements in a general sampling of healthy persons without vascular dysfunction.

Figure 28:
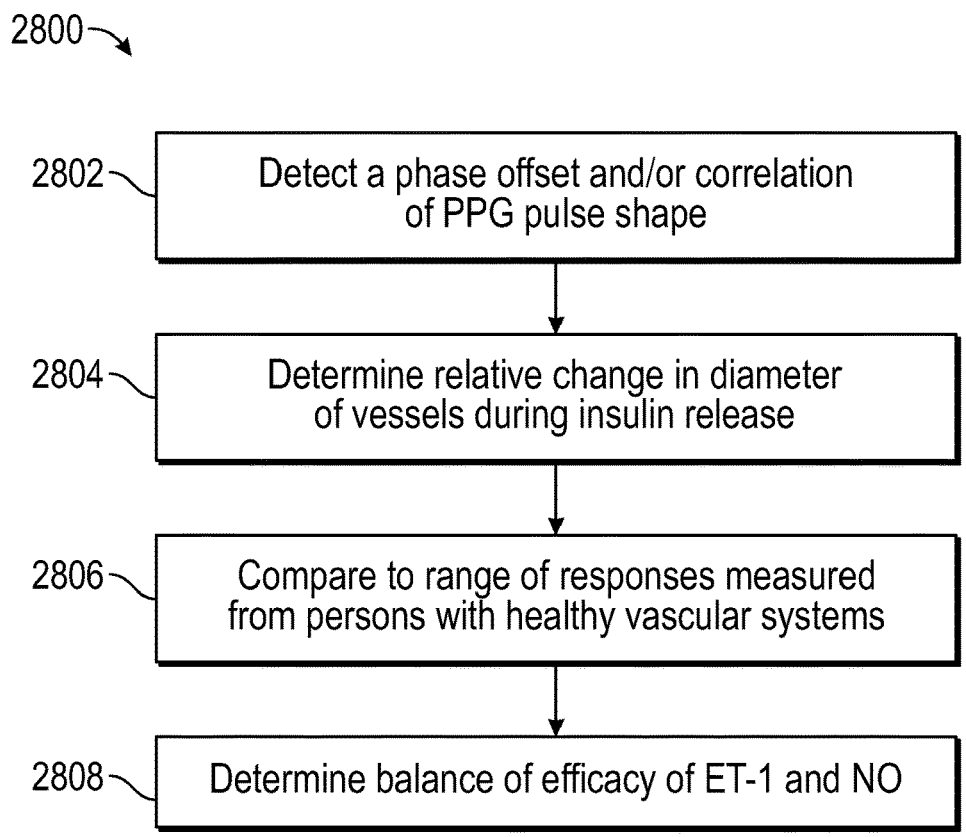
FIG. 28 illustrates a schematic flow diagram of an embodiment of a method for determining an efficacy balance of ET-1 and NO in smooth muscle cells of vessels.

FIG. 28 illustrates a schematic flow diagram of an embodiment of a method 2800 for determining an efficacy balance of ET-1 and NO in smooth muscle cells of vessels. The vasoconstriction or vasodilation in response to insulin release is affected by the balance of ET-1 and NO as well as vascular disease such as atherosclerosis. By measuring the relative vasoconstriction or change in arterial diameter in response to insulin release, the relative efficacy and balance of ET-1 and NO may be assessed using the biosensor 100.

The phase offset and/or correlation of pulse shape of two or more PPG signals is determined over the period of time including the insulin release at 2802. For example, the first wavelength has a high absorption coefficient for NO and a lower penetration depth into tissue, and the second wavelength has a lower absorption coefficient for NO and a higher penetration depth into tissue. A cross correlation function may be used to determine the phase offset and/or pulse shape correlations or a Hilbert transformation or another algorithm that determine similarities in pulse shape and temporal relationship between PPG signals.

An imbalance in the effects of the two substances has an increased vasoconstrictor effect on vessels due to an increase in ET-1 activity and suppression of NO efficacy. The change in diameter of vessels during insulin release may be determined at 2804 and compared to a healthy individual of similar age with no vascular dysfunction at 2804. Increased relative levels of vasoconstriction may be indicative of increased ET-1 activity due to an imbalance of ET-1 and NO efficacy caused by insulin-resistance disease such as diabetes.

The phase delay may also provide an indication of the balance of ET-1 and NO in response to insulin. For example, the R value is compared to systolic peaks of the phase delay to determine a relative level of vasoconstriction or change in diameter of vessels. The phase offset between two or more of the PPG signals in different spectrums, or having different depths of penetration of tissue, is measured. The phase offset may be used to determine presence of vasodilation/vasoconstriction in the tissue. For example, in normal tissue, the PPG signals exhibit only a slight difference in phase or timing when nominal vasodilation is occurring in the tissue. When the PPG signals have a greater difference in phase or timing, this indicates that blood flow in the tissue near the surface is decreased, e.g. due to vasoconstriction, due to low blood circulation level or an imbalance of NO and ET-1 or arterial stiffness. When blood flow is increased to the tissue, the PPG signals at UV and IR wavelengths exhibit a lower variance in pulse shape and a higher correlation value. This decrease in the difference in the pulse shape of the PPG signals at the different wavelengths indicates an increase of blood flow, e.g. due to vasodilation.

The phase offset and pulse shape correlation may be mapped to a level of vasodilation/vasoconstriction, e.g. using a calibration table or function. The level of vasodilation/vasoconstriction and a period of vasodilation/vasoconstriction may thus be determined using the phase differences and pulse shape correlations between the PPG signals at the different wavelengths. The above described parameters of the PPG signals may also be used to determine a period of vasoconstriction using similar methods.

In another aspect, R values are determined using the PPG signals at least two wavelengths, such as $R_{660\ nm/940\ nm}$ or $R_{405/940}$ or $R_{395\ nm/940\ nm}$. The level of vasodilation or period of vasodilation may be determined using changes in amplitude of one or more R values.

The level of vasoconstriction/vasodilation may be compared to an insulin level to determine the balance of the effects of ET-1 and NO at 2808. For example, the level of vasoconstriction/vasodilation for a known insulin level or during an average insulin release event may be determined in individuals with healthy vascular function. A calibration table or function may store a mapping of a range of vasoconstriction/vasodilation and/or an average period of vasoconstriction/vasodilation for one or more levels of insulin release by testing a general population of healthy individuals. The level of vasodilation may be represented as a measurement of one or more of: a percentage of change in arterial width, diameter or planar area or a change in blood flow or volume, etc. These comparisons may thus indicate a balance of efficacy between ET-1 and NO at 2808.

In addition, arterial stiffness may decrease a relative level of vasodilation compared to an average or normal range. The rate of change of the width of the artery at a beginning or end of vasodilation may be used as an indicator of arterial stiffness. A reduction in elasticity of arteries may decrease the rate of change in the width of the artery and thus the rate of change in the level of vasodilation. These comparisons of the rate of change of the width of vessels may also be used to indicate a measurement of arterial stiffness. These determinations may also factor in the determination of whether the cause of reduced vasoconstriction/vasodilation is due to an imbalance of ET-1 and NO or due to arterial stiffness during an insulin release event.

Measurement of Insulin Levels

Figure 29:
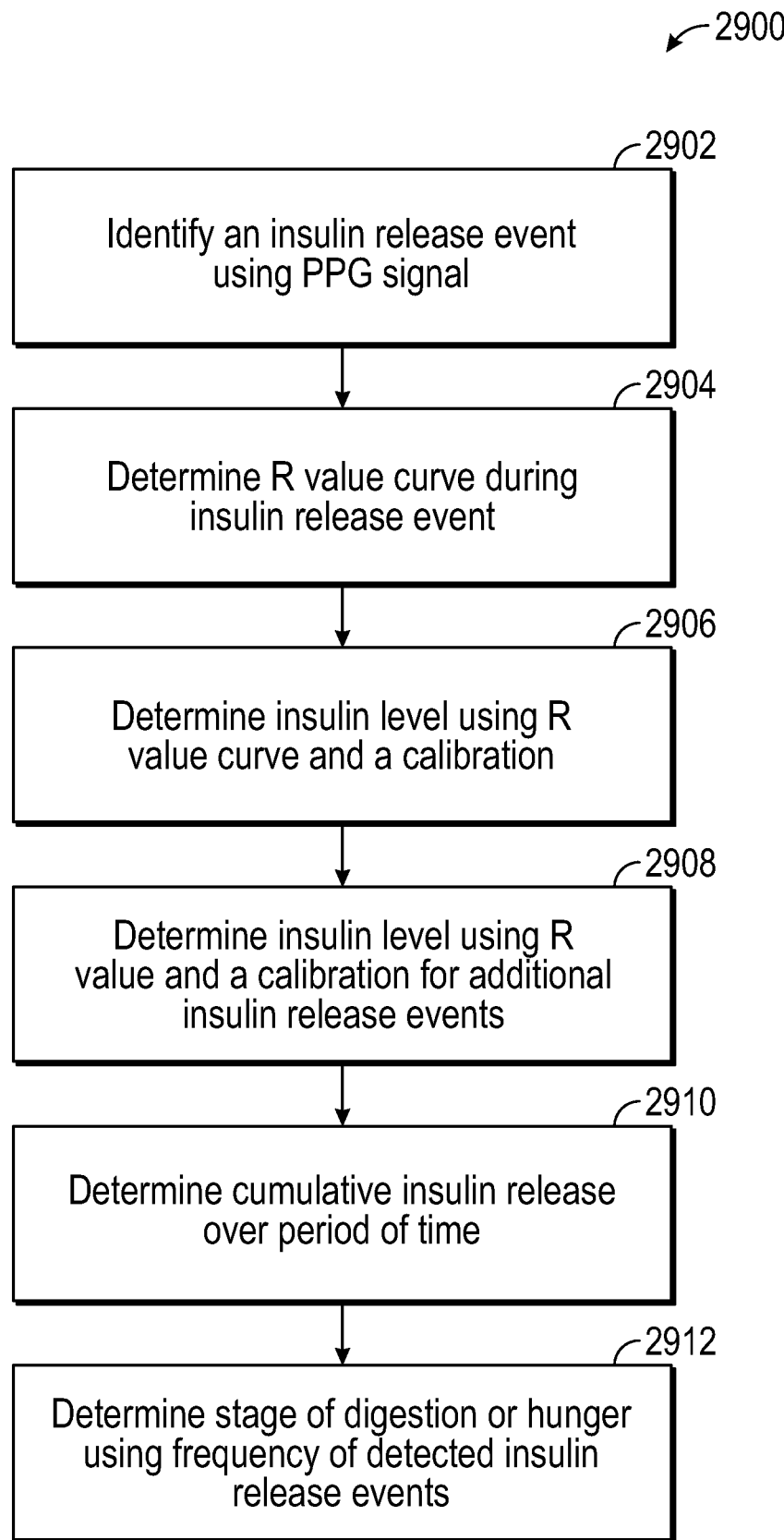
FIG. 29 illustrates a schematic flow diagram of an embodiment of a method 2900 for determining an insulin level in blood flow.

FIG. 29 illustrates a schematic flow diagram of an embodiment of a method 2900 for determining an insulin level in blood flow. The biosensor 100 monitors PPG signals at a plurality of wavelengths reflected from skin tissue over a period of time, such as 5 minutes to 24 hours. Preferably, a first wavelength has a high absorption coefficient for NO and is approximately 395 nm or in a range from 380 to 410. A second wavelength has a lower absorption coefficient for NO and is approximately 530 nm or in a range from 510 nm to 550 nm or is in an IR range such as 940 nm.

The PPG signals are analyzed to identify one or more insulin release events at 2902. For example, after ingestion, insulin is naturally released into the blood stream. The insulin release effects a marked PPG pulse in the first wavelength having a high absorption coefficient for NO. The PPG pulse, e.g., has a longer duration than a PPG pulse of a heart rate. For example, the PPG pulse during an insulin release event has an approximately 5-10 second duration, wherein the change in amplitude of the PPG pulse is at least greater than twice expected from a heart rate pulse. Signal analysis using pattern recognition may be employed with the PPG signals to identify the insulin pulse.

An R value curve is obtained over the period of the insulin release event, using PPG signals having the first and second wavelength, such as an R value of 395 nm/530 nm or 395 nm/940 nm at 2904. The R value curve during the insulin release event is analyzed to determine an insulin level at 2906. For example, an area under the R value curve is determined during the insulin release event. A calibration table or curve is tabulated that associates the area to the insulin level. The calibration may be performed on an individual using a blood test to determine insulin levels during a calibration phase of the biosensor. Alternatively, the calibration may be predetermined from testing of a general population. Though an area under the R value curve is described for the calibration, other parameters obtained from the pulse of the PPG signals during the insulin release event may be used to determine insulin levels, such as an average R value or $I_{AC}$ value.

Insulin is usually secreted in discrete amounts one or more times depending on the stage of digestion. Thus, multiple insulin release events may be detected within a short time period after ingestion. The insulin level may be determined for additional insulin release events using the R value curve and calibration table at 2908. The cumulative insulin released over a time period may then be determined at 2910 by summation of the individual insulin release events during the time period.

The stage of digestion may also be determined using identification of the insulin release events from the PPG signals. For example, the insulin release events are more frequent after ingestion during stage 1 and stage 2 of digestion and are less frequent when hungry. Correspondingly, the frequency of PPG pulses due to insulin release events increases in response to different stages of digestion. In contrast, the frequency of the PPG pulses due to insulin release events decreases in response to fasting or hunger. Thus, by measuring the frequency or time between insulin release events using the PPG signals, a stage of digestion may be identified or a level of fasting or hunger may be identified at 2912.

Measurement of Glucose Levels

As described herein, the biosensor may determine a glucose level by averaging an R value over a short period of time (e.g., around 2-3 minutes) and using a calibration to obtain a glucose level associated with the R value. This method has predictable results for healthy persons with little to no vascular dysfunction. However, for persons with certain diseases, e.g. affecting arterial health, this method may not provide accurate results due to unhealthy vasoconstriction of arterioles near the surface of the skin or tissue. For example, diabetes creates extreme vasoconstriction that affects the R value and results in inaccurate correlations to NO and glucose levels.

Figure 30:
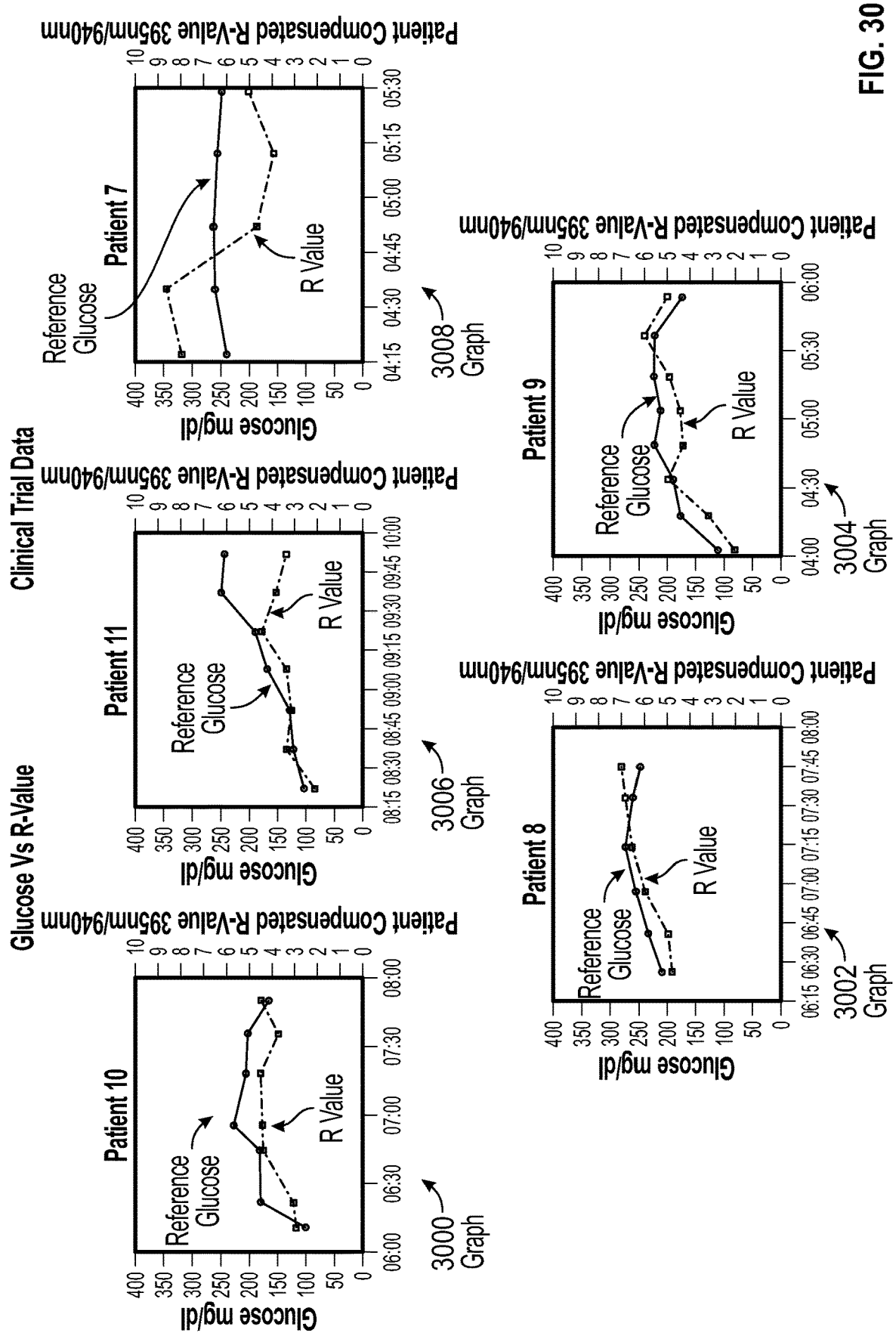
FIG. 30 illustrates schematic diagrams of measurements of glucose levels in a plurality of patients using the biosensor in a clinical trial.

FIG. 30 illustrates schematic diagrams of measurements of glucose levels in a plurality of patients using the biosensor in a clinical trial. In this example, the patients ingested a caloric intake, and then a reference glucose was tested at discrete points using a blood test. In addition, the biosensor 100 detected an R value at 395 nm/940 nm at the discrete points. The patients in graphs 3000, 3002 and 3004 had a seemingly healthy vascular function and NO response. The R value approximately tracked the trend in the reference glucose. Thus, the R value provides a predictable tracking of trends in glucose, and a universal calibration table or curve may be compiled to correlate R values and glucose levels in these patients.

However, the patients in graphs 3006 and 3008 exhibited vascular dysfunction. The R value diverged from the reference glucose at one or more of the discrete points. For example, the vasodilation effect during phase 2 of digestion created unexpected results in the R values. Thus, in patients with atypical vascular responses, individual calibration of glucose levels to R values may need to be performed.

Figure 31:
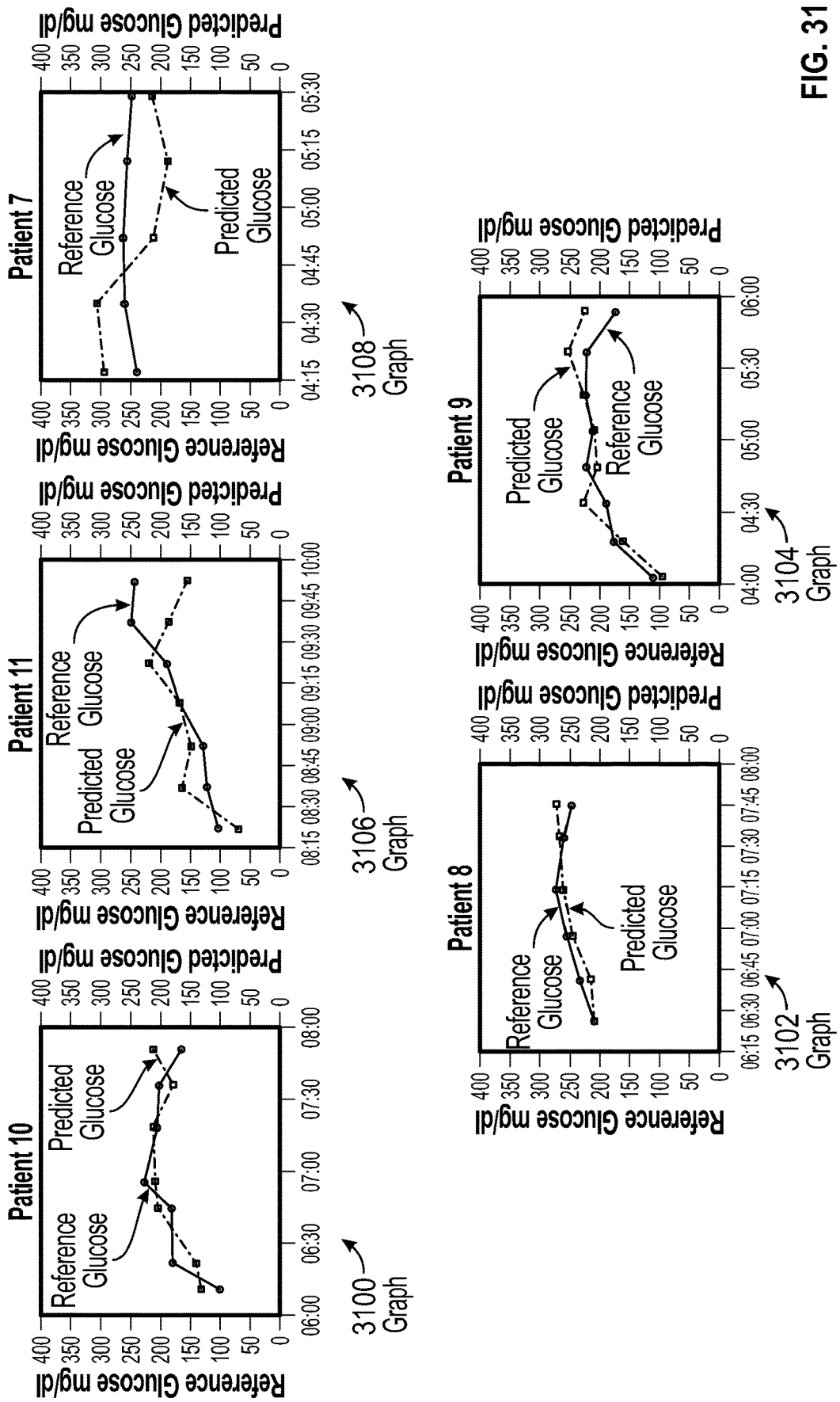
FIG. 31 illustrates schematic diagrams of measurements of glucose levels in a plurality of patients using the biosensor in a clinical trial.

FIG. 31 illustrates schematic diagrams of measurements of glucose levels in a plurality of patients using the biosensor 100 in a clinical trial. In this example, the reference glucose is displayed with a predicted glucose value that is obtained using the $R_{395\ nm/940\ nm}$ values shown in FIG. 30. The R values for patients in graphs 3000, 3002 and 3004 with a seemingly healthy vascular function and NO response were correlated to the predicted glucose values using a universal calibration. The universal calibration correlates R values and glucose values based on a clinical testing from a general sample population of persons with healthy vascular systems. The universal calibration may include a table, equation, factor or curve. Thus, the R value provides a predictable tracking of trends in glucose for patients with a relatively healthy vascular response, and a universal calibration may be compiled to correlate R values and glucose levels in these patients.

However, the R values for patients in graphs 3106 and 3108 are correlated to the predicted glucose values using individual calibrations. For example, the R value is obtained, and an interim glucose value is estimated using the universal calibration. The interim glucose value is then adjusted using an individual calibration. A difference or other correlation between the interim glucose value and the reference glucose is determined at one or more points of time. The difference or other correlation is used as an individual calibration to adjust the interim glucose value to the predicted glucose levels shown in Graphs 3106 and 3108. Thus, for patients with vascular dysfunction, an individual calibration is used to obtain the predicted glucose levels from the R values In another embodiment, the individual calibration directly correlates the R values to the predicted glucose level for patients with vascular dysfunction. The reference glucose at one or more discrete points is compared to the $R_{395\ nm/940\ nm}$ values at the same discrete points, and the individual calibration is obtained.

The individual calibration should be recalculated at least every 2-3 months due to potential change in vascular function. For example, arteriolosclerosis or insulin resistance may further deteriorate the vascular health such that the vessels exhibit increased vasoconstriction. This deterioration may affect the level of vasoconstriction in vessels and the correlation between R values and glucose levels.

Figure 32:
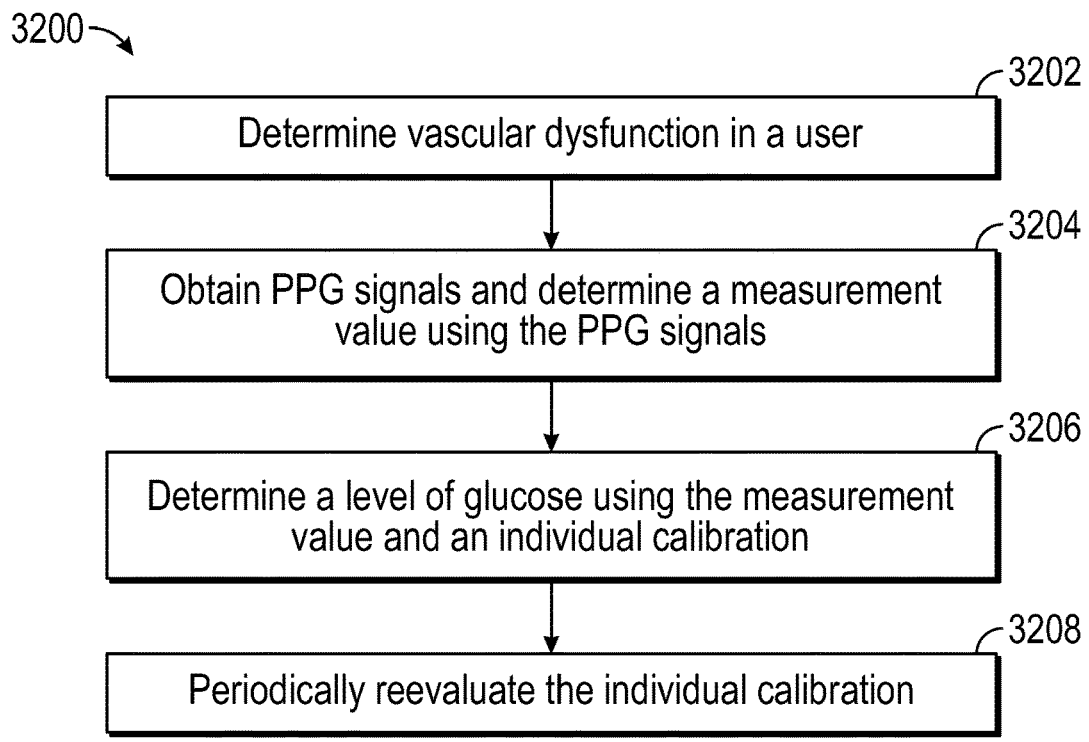
FIG. 32 illustrates a schematic flow diagram of an embodiment of a method for determining glucose levels of a patient with atypical vascular function.

FIG. 32 illustrates a schematic flow diagram of an embodiment of a method 3200 for determining glucose levels of a patient with atypical vascular function. The biosensor 100 determines that a user has vascular dysfunction or a disease that typically leads to vascular dysfunction, such as diabetes, heart disease or arteriolosclerosis, at 3202. The user may input or request individual calibration. The PPG signals are obtained, preferably at a first wavelength with a high absorption coefficient for NO, such as 395 nm or in a range around 380 nm to 410 nm and determining a measurement value using the PPG signals at 3204. The measurement value may include, e.g., an R value at 395/940 or 395/530 wavelength ratios.

The biosensor 100 may then determine a level of glucose using the measurement value and an individual calibration at 3206. For example, the R value is obtained, and an interim glucose value is estimated using the universal calibration. The interim glucose value is then adjusted using an individual calibration. In another embodiment, the individual calibration directly correlates the R values to the predicted glucose level for patients with vascular dysfunction. Thus, for patients with vascular dysfunction, an individual calibration is used to obtain the predicted glucose levels from the R values.

The individual calibration should be re-evaluated periodically at 3208. For example, the individual calibration should be updated at least every 2-3 months due to potential changes in vascular function.

Figure 33:
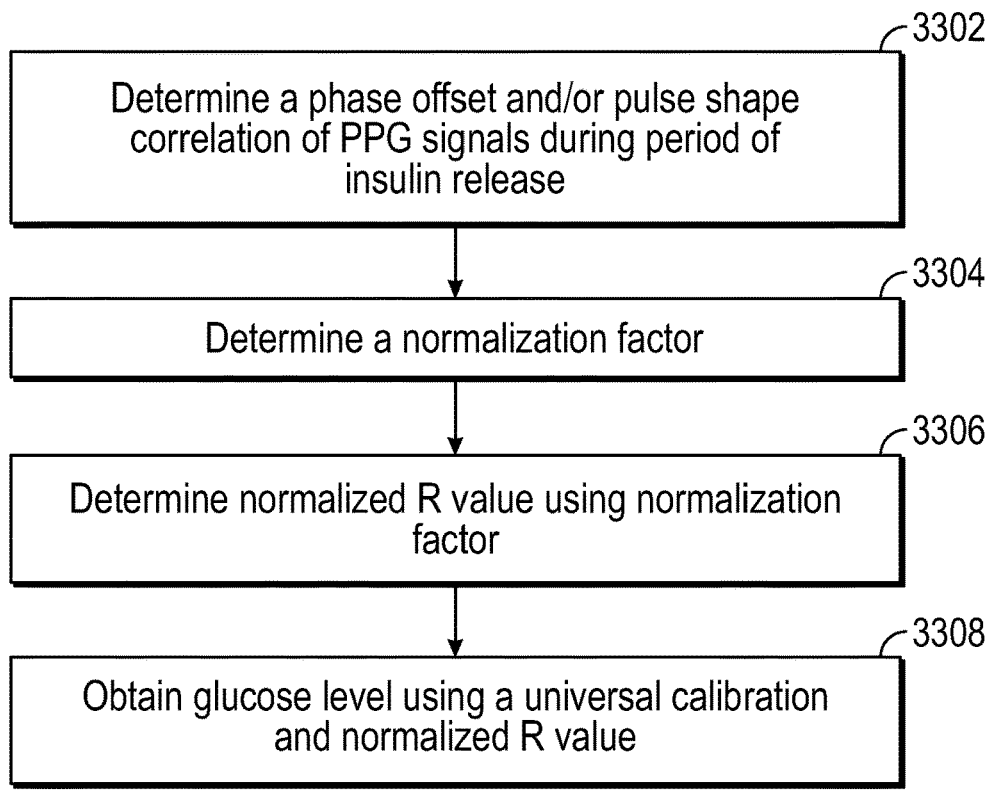
FIG. 33 illustrates a schematic flow diagram of another embodiment of a method for determining glucose levels of a patient with atypical vascular function.

FIG. 33 illustrates a schematic flow diagram of another embodiment of a method 3300 for determining glucose levels of a patient with atypical vascular function. As shown in the example of Graph 1900, the biosensor 100 obtains PPG signals over a time period between around a plurality of wavelengths at 940 nm, 630 nm, 590 nm, 530 nm, 440 nm and 395 nm. The "pulses" in response to discrete release of insulin in the bloodstream are identified in the PPG signals. Then a correlation is computed between the PPG waveform with a low absorption coefficient for NO (e.g., 440 nm, 530 nm or another wavelength in the visible range or in the IR range) and the PPG waveform with a high absorption coefficient for NO (e.g., at 395 nm or in a range of +/−10 nm of 395 nm) during the period of release of insulin to obtain a Pulse Shape Correlation and a Phase Delay at 3302. The PPG signals are processed using, e.g., a cross correlation function or a Hilbert transformation or another algorithm that determines similarities in pulse shape and temporal relationship between the PPG signals.

The phase offset or waveform correlation may then be used to determine a factor to "normalize" an R value to obtain a normalized R value at 3306. Thus, the normalization factor may account for increased vasoconstriction due to vascular dysfunction. For example, the R value may be divided by an averaged phase offset factor or an averaged pulse shape correlation to determine the "normalized" R value. The normalized R value is then correlated to a glucose level using a universal calibration table or curve at 3308. The normalization factor compensates the R value in patients with vascular dysfunction.

In another embodiment, a plurality of calibrations may be implemented, each assigned to one or more different normalization factors. The glucose level is determined using the calibration table associated with the determined normalization factor.

Identification of Deep Inhalation

Figure 34:
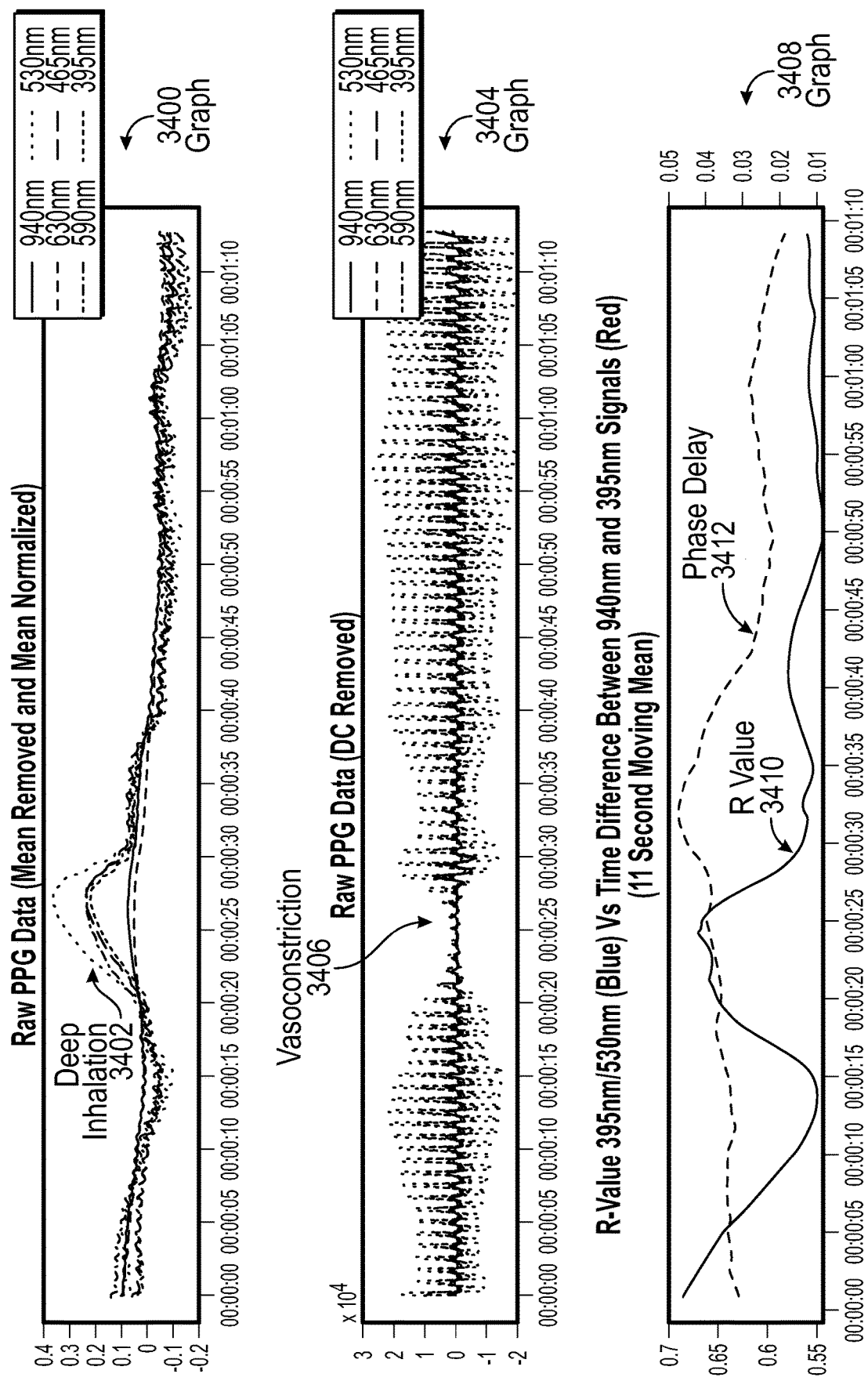
FIG. 34 illustrates a schematic diagram of graphs of PPG signals during deep inhalation.

FIG. 34 illustrates a schematic diagram of graphs of PPG signals during deep inhalation. A rapid, deep inspiration is also known to induce vasoconstriction of skin arterioles. In particular, a deep inhalation may vastly reduce the amplitude of PPG pulse waveforms and also introduce marked low-frequency components as a consequence of vasoconstriction and subsequent vasodilatation. These changes due to deep inspiration may create difficulties in accurately identifying PPG waveform features, such as insulin release periods. This also increases the error when computing physiological measures.

Graph 3400 illustrates PPG signal obtained during a deep inhalation 3402 around a plurality of wavelengths at 940 nm, 630 nm, 590 nm, 530 nm, 465 nm and 395 nm. The deep inhalation caused a decrease in the PPG pulse amplitude along with a characteristic low-frequency trend as seen in Graph 3404. Graph 3404 shows the $I_{AC}$ signal due to pulsatile blood flow. Because of the excessively low amplitude indicative of vasoconstriction 3406, the deep inhalation may be mistaken for an insulin release event.

Graph 3408 illustrates the R value 3410 of 395 nm/530 nm is illustrated. In addition, a correlation is computed between the PPG waveform at 940 nm and the PPG waveform at 395 nm to obtain a Phase Delay 3412. The PPG signals are processed using, e.g., a cross correlation function or a Hilbert transformation or another algorithm that determines similarities in pulse shape and temporal relationship between PPG signals. For example, the time delay between the two signals can also be calculated at each time instant from the phase shift of their wavelet transforms.

The R value 3410 has a low amplitude indicative of vasoconstriction 3406, such as in insulin release or deep inhalation. However, the phase delay 3412 does not indicate an insulin release. As seen in Graph 2404 in FIG. 24, the phase delay 2414 in response to an insulin release has a corresponding pulse with a large amplitude change. The phase delay 3412 in response to the deep inhalation 3402 fails to include such a pulse at a time corresponding to the vasoconstriction 3406. Thus, the vasoconstriction 3406 may be identified as an inhalation or other vasoconstriction causing event and not due to insulin release. Such pattern recognition may be performed to identify insulin release events recorded by the PPG signals.

Detection of Sepsis

Figure 35:
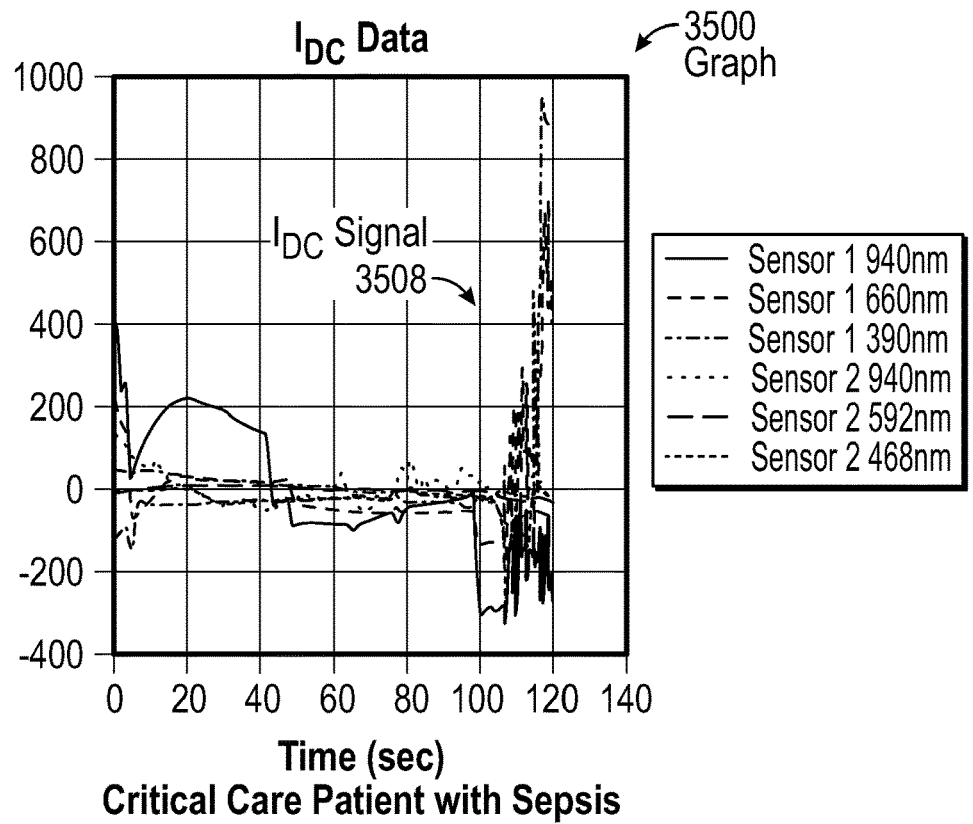
FIG. 35 illustrates a schematic diagram of graphs of PPG signals detected from a critical care patient diagnosed with sepsis.
Figure 35:
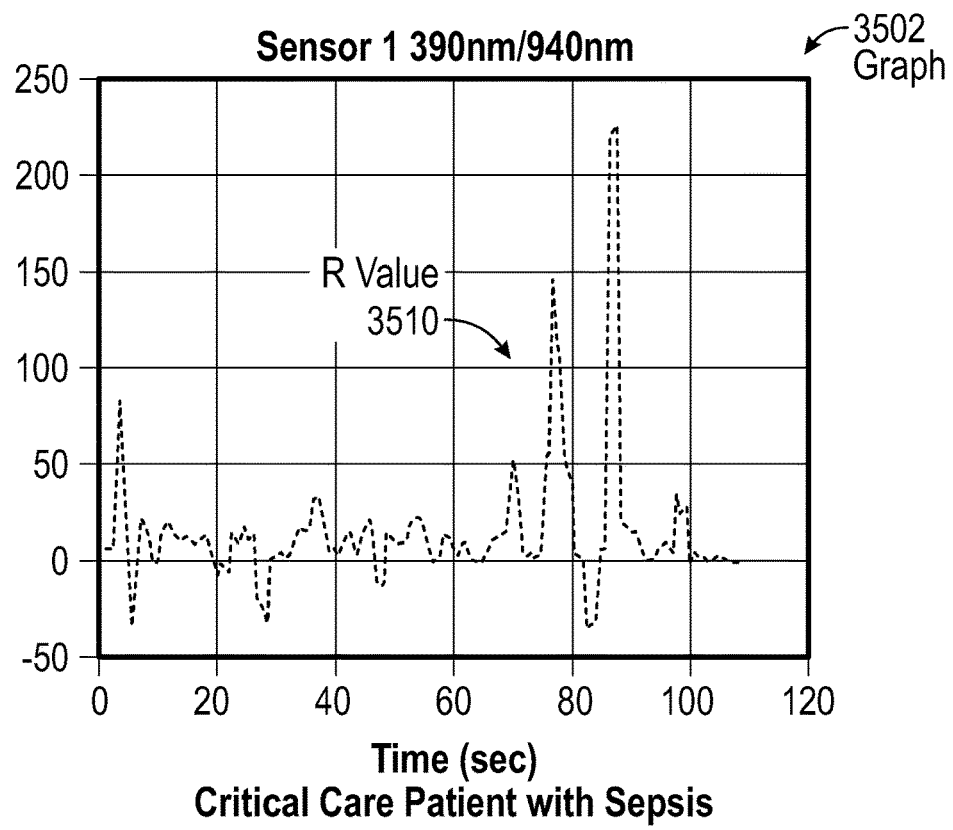

FIG. 35 illustrates a schematic diagram of graphs of PPG signals detected from a critical care patient diagnosed with sepsis. The biosensor 100 obtained PPG signals over a time period of approximately two minutes around a plurality of wavelengths at 940 nm, 630 nm, 590 nm, 530 nm, 440 nm and 390 nm. Graph 3500 illustrates the $I_{DC}$ signal 3508 of low frequency signals with the $I_{AC}$ signal filtered. The $I_{AC}$ signal has erratic frequency pulses with high amplitude peaks, especially at the 390 nm with a high absorption coefficient for NO. Graph 3502 illustrates the R value 3510 obtained for 390 nm/940 nm. The R value 3510 also has an erratic signal that fluctuates between positive and negative values with extremely high amplitude peaks. The R value in this example exceeds 200.

These large peaks in sepsis patients may initially create difficulties in accurately identifying PPG waveform features, such as insulin release periods. However, in patients with sepsis, the PPG responses are erratic in frequency with peaks exceeding amplitudes typically seen in insulin release periods. In addition, the R values for 390 nm/940 nm has abnormally high values exceeding 10 times normal and then may also have negative values.

Detection of Digestion or Hunger

Figure 36:
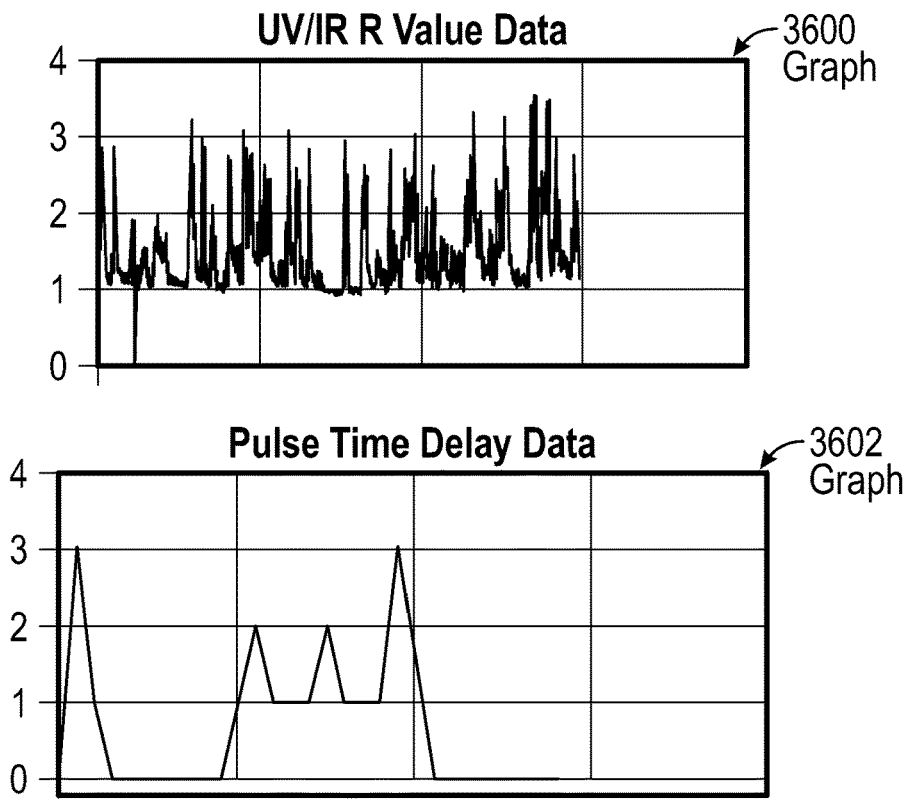
FIG. 36 illustrates a schematic diagram of graphs of PPG signals during periods of ingestion and fasting.

FIG. 36 illustrates a schematic diagram of graphs of PPG signals during periods of ingestion and fasting. Graph 3600 illustrates an R value obtained from PPG signals at 395 nm and 940 nm over an approximate 88 minute time period. The patient ingested food at approximately 19 minutes. The Graph 3600 shows insulin release pulses with a frequency of approximately every 2-3 minutes after ingestion. In contrast, Graph 3602 shows PPG signal response over an approximately 102 minute period. The patient has not ingested caloric intake. The insulin release pulses have a frequency of approximately every 10-20 minutes. Thus, by determining a frequency or average period between insulin release pulses, an ingestion stage or digestion stage may be determined. In addition, a hunger level or time from ingestion may also be determined from the time between insulin release pulses.

The stage of digestion may thus be determined using identification of the insulin release events from the PPG signals. For example, the insulin release events are more frequent after ingestion during stage 1 and stage 2 of digestion and are less frequent in response to fasting or hunger. Thus, by measuring the frequency or time between insulin release events using the PPG signals, a stage of digestion may be identified or a level of fasting or hunger may be identified.

Calibration During Ingestion Periods

During ingestion, a greater frequency of insulin release pulses may affect the PPG signals. The walls of the blood vessels are constricting and harden due to muscle tension and may generate false readings of arterial stiffness or blood flow. The calibration for determining glucose levels may need to be adjusted during such ingestion periods.

In addition, during insulin release, vascular imaging or tests, such as a CT Scan or ultrasound or MRI of the blood flow of the vascular system should be avoided. The walls of the vessels may not exhibit normal behavior during insulin release. By measuring the frequency or time between insulin release events using the PPG signals, a stage of digestion may be identified. Depending on the stage of digestion and frequency of insulin release events, the vascular imaging or tests may be performed or delayed.

Figure 37:
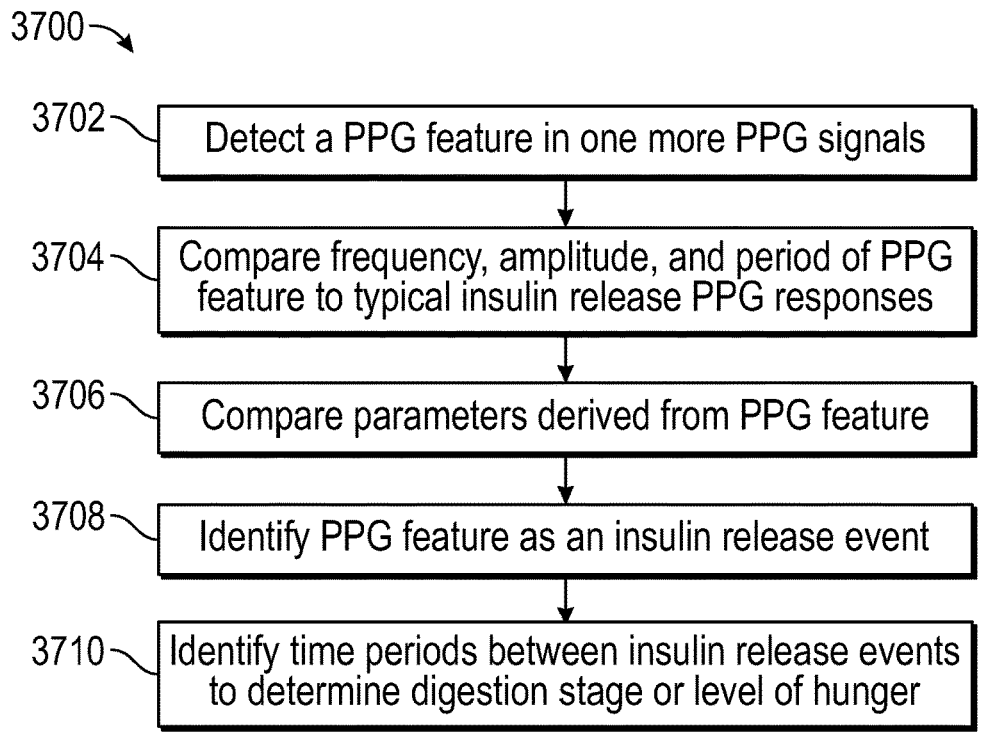
FIG. 37 illustrates a schematic flow diagram of an embodiment of a method for identifying a PPG feature, such as an insulin release pulse or deep inhalation pulse.

FIG. 37 illustrates a schematic flow diagram of an embodiment of a method 3700 for identifying a PPG feature, such as an insulin release event. A pulse or amplitude peak is detected in PPG signals at one or more wavelengths at 3702. The frequency, amplitude and period of the PPG feature are compared to typical or average responses or characteristics of PPG signals during an insulin release event at 3704. For example, PPG pulses due to an insulin release have a much lower frequency than a heart rate. The frequency increases after ingestion and then decreases with hunger. The period of the pulse for an insulin pulse is longer than a typical heartbeat, for example lasting over 4-10 seconds and have an $I_{AC}$ amplitude that is at least 50% less than a heartbeat pulse. Thus, the biosensor 100 may determine a change in amplitude of the PPG signals and compare the change in the amplitude of the PPG signals to a predetermined range of the amplitude of PPG signals during an insulin release event. The predetermined range may include an average or mean of the amplitude or a percentage of change during the insulin release event. The predetermined range of the amplitude may be obtained from testing of a general population with a healthy vascular system.

Additionally, the biosensor 100 may determine a period of the pulse and compare to a predetermined range of periods of PPG pulses during an insulin release event. The predetermined range may include an average or mean of the period of the pulse during an insulin release event. The predetermined range of the period may be obtained from testing of a general population with a healthy vascular system.

Furthermore, a frequency or time between pulses may also be determined and compared to predetermined frequencies or a count of a number of pulses typically found during digestion or hunger. This comparison may be used to determine a stage of digestion or level of hunger or estimated time since ingestion of caloric intake.

The frequency, amplitude and period of the PPG feature may also be compared to typical responses of PPG signals during other events, such as deep inhalation, sepsis or other types of features. Thus, other types of PPG responses may also be identified.

In addition, one or more parameters derived from the PPG signals may be compared to known patterns or characteristics to identify an insulin release pulse at 3706. For example, the $I_{AC}$ signal, an L value curve or an R value curve (such as 390 nm/940 nm) is determined from the PPG signals. These parameters are then compared to predetermined ranges for the corresponding parameter during an insulin release event. For example, an R value for an insulin pulse is much lower than R values in a sepsis patient. In addition, the R value has a similar pulse shape and timing as the PPG signal of $I_{AC}$ for an insulin release event while there is less correlation between the R value and the $I_{AC}$ signal with deep inhalation. Other parameters such as integrals or derivatives or wavelet transforms or correlations between PPG signals may be determined and compared to predetermined normal ranges during insulin release events. The PPG feature is then identified at 3708 as an insulin release event or may be identified as a sepsis condition, deep inhalation or other feature.

When the PPG feature is identified as an insulin release event, the frequency or time between insulin release events may be measured using the PPG signals to determine a stage of digestion or a level of hunger at 3710. A time since ingestion of caloric intake may also be estimated.

Biosensor Configurations

The largest blood vessels are arteries and veins, which have a thick, tough wall of connective tissue and many layers of smooth muscle cells. The wall is lined by an exceedingly thin single sheet of endothelial cells, the endothelium, separated from the surrounding outer layers by a basal lamina. The inner layer (tunica intima) is the thinnest layer, formed from a single continuous layer of endothelial cells and supported by a subendothelial layer of connective tissue and supportive cells.

Farther from the heart, where the surge of blood has dampened, the percentage of elastic fibers in an artery's tunica intima decreases and the amount of smooth muscle in its tunica media increases. The artery at this point is described as a muscular artery. The diameter of muscular arteries typically ranges from 0.1 mm to 10 mm. Their thick tunica media allows muscular arteries to play a leading role in vasoconstriction. In contrast, their decreased quantity of elastic fibers limits their ability to expand.

The radial artery and the proper digital artery to the index finger are muscular arteries with greater smoother muscle cells. Their thick tunica media allows these muscular arteries to play a leading role in vasoconstriction. In contrast, their decreased quantity of elastic fibers limits their ability to expand. The radial artery extends to arterioles and capillaries in the fingertip of the index finger. An arteriole is a small-diameter blood vessel in the microcirculation that extends and branches out from an artery and leads to capillaries. An arteriole is a very small artery that leads to a capillary. Arterioles have the same three tunics as the larger vessels, but the thickness of each is greatly diminished. The critical endothelial lining of the tunica intima is intact. The tunica media is restricted to one or two smooth muscle cell layers in thickness. The tunica externa remains but is very thin. The precise diameter of the lumen of an arteriole at any given moment is determined by neural and chemical controls, and vasoconstriction and vasodilation in the arterioles are the primary mechanisms for distribution of blood flow.

Capillaries consist only of the thin endothelial layer of cells with an associated thin layer of connective tissue. The amounts of connective tissue and smooth muscle in the vessel wall vary according to the vessel's diameter and function, but the endothelial lining is always present. In the finest branches of the vascular tree—the capillaries and sinusoids—the walls consist of nothing but endothelial cells and a basal lamina, together with a few scattered—but functionally important—pericytes. These are cells of the connective-tissue family, related to vascular smooth muscle cells, that wrap themselves round the small vessels. Capillaries consist of a single layer of endothelium and associated connective tissue without smooth muscle cells.

Due to the different vascular structure at different depths, the use of an R value of 395 nm/530 nm wavelengths may be preferred in obtaining results from tissues in a finger or other tissues wherein vessels are closer to the surface. For example, in some instances it may be preferred that wavelengths penetrate the tissue at similar depths due to variations in the vascular profile at different depths. The R value described herein may also be computed using wavelengths with a low absorption coefficient for NO at 440 nm, 530 nm or another wavelength in the visible range or in the IR range) and a wavelength with a high absorption coefficient for NO (e.g., at 395 nm or in a range of +/−10 nm of 395 nm). The use of an R value of 395 nm/530 nm wavelengths may be preferred in obtaining results from tissues in a finger or other tissues wherein vessels are closer to the surface. For example, in some instances it may be preferred that wavelengths penetrate the tissue at similar depths due to variations in the vascular profile at different depths.

In addition, due to the different vascular structure at different tissue sites, the biosensor 100 is preferably calibrated for the type of tissue at a detection site. The same detection site is preferably maintained throughout a measurement period because vascular structure and dynamics varies between different tissue sites. The variation may affect the calibration and relative amplitude of the PPG signals.

Figure 38:
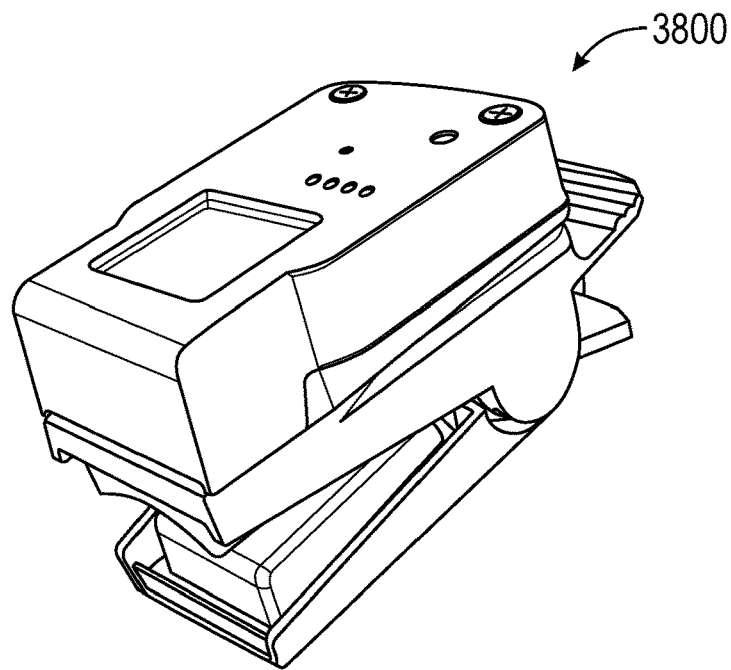
FIG. 38 illustrates an elevational view of a biosensor configured for attachment to an appendage.

FIG. 38 illustrates an elevational view of a biosensor 3800 configured for attachment to a fingertip or toe. The detection site of a fingertip or toe tip is positioned within the two pads. The two pads help prevent disturbance from ambient light. The biosensor 3800 projects the light at the plurality of wavelengths onto the tissue of the fingertip or toe tip to perform the health measurements.

Figure 39:
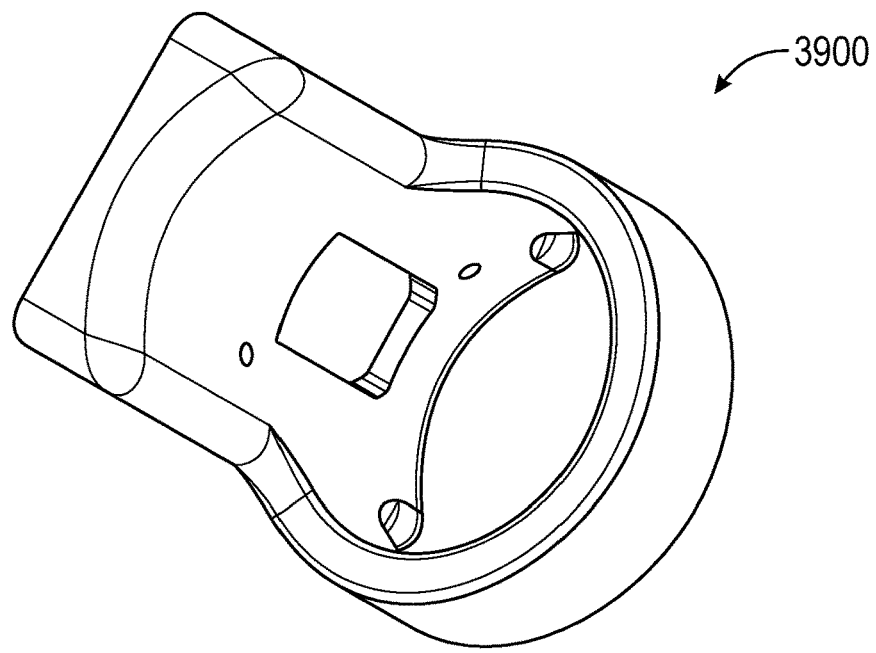
FIG. 39 illustrates an elevational view of a biosensor configured in a ring.

FIG. 39 illustrates an elevational view of a biosensor 3900 configured in a ring. The ring may be positioned around a finger or toe. The biosensor 3900 projects the light at the plurality of wavelengths onto the tissue of the finger or toe under the ring to perform the health measurements.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A device, comprising:
    an optical circuit configured to detect photoplethysmography (PPG) signals, wherein a first PPG signal includes a first spectral response obtained from light reflected around a first wavelength from tissue of a user and a second PPG signal includes a second spectral response obtained from light reflected around a second wavelength from the tissue of the user; and
    a processing device configured to identify an insulin release event using the first PPG signal and the second PPG signal, wherein the insulin release event includes a discrete pulse of insulin in blood flow of the user.

2. The device of claim 1, wherein the processing device is configured to identify the insulin release event using the first PPG signal and the second PPG signal by:
    determining a change in amplitude of the first PPG signal or the second PPG signal; and
    comparing the change in the amplitude of the first PPG signal or the second PPG signal to a predetermined range of amplitude of PPG signals during an insulin release event.

3. The device of claim 1, wherein the processing device is further configured to:
    determine a correlation signal during the insulin release event between the first PPG signal and the second PPG signal, wherein the correlation signal includes a phase delay between the first PPG signal and the second PPG signal or a pulse shape correlation between the first PPG signal and the second PPG signal; and
    determine a measurement of vascular health using the correlation signal.

4. The device of claim 3, wherein the processing device is further configured to determine a level of vasoconstriction using the correlation signal during the insulin release event.

5. The device of claim 4, wherein the processing device is further configured to:
    compare the level of vasoconstriction to a predetermined range of vasoconstriction measured from a general population with healthy vascular systems; and
    determine a balance of efficacy of endothelin (ET-1) and nitric oxide (NO) during the insulin release event.

6. A biosensor, comprising:
    an optical circuit configured to:
        detect a first PPG signal reflected around a first wavelength from skin tissue of a patient and a second PPG signal reflected around a second wavelength from the skin tissue of the patient;
    a processing circuit configured to:
        identify a discrete insulin pulse in the blood flow using the first PPG signal or the second PPG signal;
        determine a level of vasoconstriction during the discrete insulin pulse;
        compare the level of vasoconstriction to a predetermined range of vasoconstriction measured from a general population with healthy vascular systems; and
        determine a balance of efficacy of endothelin (ET-1) and nitric oxide (NO) during the discrete insulin pulse.

7. The biosensor of claim 6, wherein the processing circuit is configured to determine a glucose level in a user with vascular dysfunction by:
    determining an imbalance of efficacy of ET-1 and NO during the discrete insulin pulse;
    determine an R value obtained from a first AC component of the first PPG signal and a second AC component of the second PPG signal;
    access an individual calibration table between predetermined R values and glucose levels; and
    obtain a glucose level using the individual calibration and the R value.

8. The biosensor of claim 6, wherein the processing circuit is configured to:
  determine an imbalance of ET-1 and NO efficacy during the discrete insulin pulse;
  determine an R value obtained from a first AC component of the first PPG signal and a second AC component of the second PPG signal;
  determine a normalization factor using the phase offset and determine a normalized R value using the normalization factor; and
  obtain a glucose level using the normalized R value.

9. The biosensor of claim 6, wherein the processing circuit is configured to determine an imbalance of ET-1 and NO efficacy during the discrete insulin pulse by:
  determining relative change in diameter of vessels using at least on of: the phase delay between the first PPG signal and the second PPG signal or the pulse shape correlation between the first PPG signal and the second PPG signal.

10. The biosensor of claim 6, wherein the processing circuit is further configured to:
  determine an R value curve during the insulin release event using a ratio value obtained from a first AC component of the first PPG signal and a second AC component of the second PPG signal; and
  determine an area of the R value curve during the insulin release event; and
  determine the insulin level using the area of the R value curve and the calibration.

11. The device of claim 6, wherein the processing device is further configured to:
  identify a number of discrete insulin pulses during a time period; and
  determine at least one of: a stage of digestion, an estimated time since caloric intake or a level of hunger.

12. The biosensor of claim 6, wherein the processing device is further configured to identify the discrete insulin pulse using the first PPG signal or the second PPG signal by:
  comparing a frequency, amplitude and period of the first PPG signal and the second PPG signal to typical PPG responses during a discrete insulin pulse; and
  determine an R value curve using a ratio value obtained from a first AC component of the first PPG signal and a second AC component of the second PPG signal; and
  compare the R value curve to typical R value curves during a discrete insulin pulse.

13. The biosensor of claim 6, wherein the first wavelength is in a range from 380 nm to 410 nm and the second wavelength is within the range from 530 nm to 940 nm.

14. A device, comprising:
  a PPG circuit configured to obtain a first PPG signal around a first wavelength reflected from skin tissue of a patient and a second PPG signal around a second wavelength reflected from the skin tissue of the patient; and
  a processing device is configured to:
    identify an insulin release event in blood flow using the first PPG signal or the second PPG signal;
    compare a parameter generated using the first PPG and the second PPG signal during the insulin release event to a predetermined range of responses generated from healthy vascular systems; and
    determine a balance of efficacy of endothelin (ET-1) and nitric oxide (NO) during the insulin release event.

15. The device of claim 14, wherein the processing device is configured to:
  determine a correlation between the first PPG signal and the second PPG signal during the insulin release event, wherein the correlation includes a time difference between the first PPG signal and the second PPG signal or a pulse shape comparison between the first PPG signal and the second PPG signal.

16. The device of claim 14, wherein the processing device is configured to:
  determine a relative change in diameter of vessels during the insulin release event using the correlation; and
  compare the relative change in diameter of the vessels during the insulin release event to a range of responses measured from a general population with healthy vascular systems; and
  determine the balance of efficacy of endothelin (ET-1) and nitric oxide (NO) during the insulin release event using the comparison.

17. The device of claim 14, wherein the processing device is configured to determine an R value using the first PPG signal and the second PPG signal during the insulin release event.

18. The device of claim 17, wherein the processing device is configured to
  compare a parameter generated using the R value to the predetermined range of responses generated from healthy vascular systems; and
  determine the balance of efficacy of endothelin (ET-1) and nitric oxide (NO) during the insulin release event using the comparison.

19. The device of claim 17, wherein the processing device is configured to:
  determine a relative change in diameter of vessels during the insulin release event using the R value; and
  compare the relative change in diameter of the vessels during the insulin release event to a range of responses measured from a general population with healthy vascular systems; and
  determine the balance of efficacy of endothelin (ET-1) and nitric oxide (NO) during the insulin release event using the comparison.

20. The device of claim 14, wherein the processing device is configured to identify the insulin release event using the first PPG signal or the second PPG signal by:
  determining a change in amplitude of the first PPG signal or the second PPG signal; and
  comparing the change in the amplitude of the first PPG signal or the second PPG signal to a predetermined range of changes in amplitude of PPG signals indicating an insulin release event.

* * * * *